US007718787B2

(12) United States Patent
Lee et al.

(10) Patent No.: US 7,718,787 B2
(45) Date of Patent: May 18, 2010

(54) GENE FAMILIES ASSOCIATED WITH CANCERS

(75) Inventors: Soojin Lee, San Diego, CA (US); Sang Seok Koh, San Marcos, CA (US); Bogman Lee, San Diego, CA (US); Hyun-Ho Chung, San Diego, CA (US); Seung-Ho Choo, San Diego, CA (US); Doo Seok Yang, San Diego, CA (US)

(73) Assignee: LG Life Sciences Limited (KR)

( * ) Notice: Subject to any disclaimer, the term of this patent is extended or adjusted under 35 U.S.C. 154(b) by 550 days.

(21) Appl. No.: 10/530,837

(22) PCT Filed: Oct. 16, 2003

(86) PCT No.: PCT/KR03/02161
§ 371 (c)(1),
(2), (4) Date: Dec. 7, 2005

(87) PCT Pub. No.: WO2004/035789
PCT Pub. Date: Apr. 29, 2004

(65) Prior Publication Data
US 2006/0168670 A1    Jul. 27, 2006

(51) Int. Cl.
C07H 21/04    (2006.01)
C12P 21/06    (2006.01)
C12N 15/63    (2006.01)
C12N 5/00     (2006.01)
A61K 31/70    (2006.01)
A01K 67/00    (2006.01)

(52) U.S. Cl. .................... 536/23.5; 435/69.1; 435/455; 435/320.1; 435/325

(58) Field of Classification Search .................. None
See application file for complete search history.

(56) References Cited

U.S. PATENT DOCUMENTS

| | | | | |
|---|---|---|---|---|
| 4,736,866 | A | 4/1988 | Leder et al. | 800/1 |
| 4,908,773 | A | 3/1990 | Pantoliano et al. | 364/496 |
| 5,143,854 | A | 9/1992 | Pirrung et al. | 436/518 |
| 5,331,573 | A | 7/1994 | Balaji et al. | 364/500 |
| 5,399,346 | A | 3/1995 | Anderson et al. | 424/93.21 |
| 5,489,743 | A | 2/1996 | Robinson et al. | 800/2 |
| 5,602,307 | A | 2/1997 | Beaudet et al. | 800/2 |
| 5,720,936 | A | 2/1998 | Wadsworth et al. | 424/9.1 |
| 5,723,719 | A | 3/1998 | Ratty et al. | 800/2 |
| 5,728,915 | A | 3/1998 | Chang et al. | 800/2 |
| 5,731,489 | A | 3/1998 | Ganten et al. | 800/2 |
| 5,731,490 | A | 3/1998 | Mak et al. | 800/2 |
| 5,873,052 | A | 2/1999 | Sharaf | 702/20 |
| 5,884,230 | A | 3/1999 | Srinivasan et al. | 702/22 |
| 5,888,738 | A | 3/1999 | Hendry | 435/6 |
| 6,015,680 | A * | 1/2000 | Tsuji et al. | 435/7.23 |
| 2006/0168670 | A1 * | 7/2006 | Lee et al. | 800/11 |

FOREIGN PATENT DOCUMENTS

| | | | |
|---|---|---|---|
| EP | 0 150 735 | * | 1/1985 |
| WO | WO 90/15070 | | 12/1990 |
| WO | WO 92/10092 | | 6/1992 |
| WO | WO 95/11755 | | 5/1995 |
| WO | WO 02/068579 | * | 9/2002 |

OTHER PUBLICATIONS

"Monitoring gene expression profile changes in ovarian carcinomas using cDNA microarray"; Authors: Kia Wang, et al.; Gene; vol. 229; 1999; pp. 101-108.
"Language Area Localization with Three-Dimensional Functional Magnetic Resonance Imaging Matches Intrasulcal Electrostimulation in Broca's Area"; Authors: G.J.M. Rutten, et al.; Brief Communications; Broca area. Ann Neurol, vol. 46, No. 3; Sep. 1999; pp. 405-408.
"The Hallmarks of Cancer"; Authors: Douglas Hanahan, et al.; Cell; vol. 100; 2000; pp. 57-70.
Insight progress"Cancer genetics"; Author: Bruce A. J. Ponder; Nature; vol. 411; May 2001; pp. 336-341.
"Tumor Suppressor Genes"; Author: Robert A. Weinberg; Science; vol. 254; Nov. 22, 1991; pp. 1138-1146.
"Distinctive gene expression patterns in human mammary epithelial cells and breast cancers"; Charles M. Perou, et al.; Proc. Natl. Acad. Sci. USA; vol. 96; Aug. 1999; pp. 9212-9217.
"Molecular Classification of Cancer: Class Discovery and Class Prediction by Gene Expression Monitoring"; Authors: T.R. Golub, et al.; Science; vol. 286; Oct. 15, 1999; pp. 531-537.
"Distinctive types of diffuse large B-cell lymphoma identified by gene expression profiling"; Authors: Ash a. Alizadeh, et al.; Nature; vol. 403; Feb. 3, 2000; pp. 503-511.
"Broad patterns of gene expression revealed by clustering analysis of tumor and normal colon tissues probed by oligonucleotide arrays"; Authors: U. Alon, et al.; Proc. Natl. Acad. Sci. USA; vol. 96; Jun. 1999, pp. 6745-6750.
"Molecular Classification of Cutaneous Malignant Melanoma by Gene Expression Profiling"; Authors: M. Bittner, et al.; Nature; vol. 406; Aug. 3, 2000; pp. 536-540.
"Molecular portraits of human breast tumours"; Authors: Charles M. Perou, et al.; Nature; vol. 406; Aug. 17, 2000; pp. 747-752.
"The Transcriptional Program in the Response of Human Fibroblasts to Serum"; Authors: Vishwanath R. Iyer, et al.; Science; vol. 283; Jan. 1, 1999; pp. 83-87.
"Gene Expression Profiling of Alveolar Rhabdomyosarcoma with cDNA Microarrays"; Authors; Javed Khan, et al.; Cancer Research; vol. 283, Nov. 15, 1998; pp. 5009-5013.

(Continued)

*Primary Examiner*—Quang Nguyen
(74) *Attorney, Agent, or Firm*—Canton Colburn LLP

(57) ABSTRACT

The invention relates generally to the changes in gene expression in human tissues from cancer patients. The invention relates specifically to human gene families which are differentially expressed in cancer tissues of breast, colon, esophagus, kidney, liver, lung, lymph node, ovary, pancreas, prostate, rectum, and/or stomach compared to corresponding normal tissues.

8 Claims, 10 Drawing Sheets

OTHER PUBLICATIONS

"Gene Expression Profile of Aging and Its Retardation by Caloric Restriction"; Authors: Cheol-Koo Lee, et al.; Science; vol. 285; Aug. 27, 1999; pp. 1390-1393.

"Proliferation, Cell Cycle and Apoptosis in Cancer"; Authors: Gerald I. Evan, et al.; vol. 411; May 17, 2001; pp. 342-348.

"Gapped BLAST and PSI-BLAST: a new generation of protein database search programs"; Authors: Stephen F. Altschul, et al.; Nucleic Acids Research; vol. 25; No. 17; 1997; pp. 3389-3402.

"Methods for Assessing the Statistical Significance of Molecular Sequence Features by Using General Scoring Schemes"; Authors: Samuel Karlin, et al.; Proc. Natl. Acad. Sci. USA; vol. 87; Mar. 1990; pp. 2264-2268.

"Issues in Searching Molecular Sequence Databases"; Authors: Stephen F. Altschul, et al.; Nature Genetics; vol. 6; Feb. 1994, pp. 119-129.

"Amino Acid Substitution Matrices from Protein Blocks"; Authors: Steven Henikoff, et al.; Proc. Natl. Acad. Sci. USA; vol. 89; Nov. 1992; pp. 10915-10919.

"Synthesis of Deoxyoligonucleotides on a Polymer Support"; Authors: M.D. Matteucci, et al.; Journal of American Chemical Society; 1981; pp. 3185-3191.

"Protein Sequence Similarity Searches Using Patterns as Seeds"; Authors: Zheng Zhang, et al.; Nucleic Acids Research; vol. 26; No. 17; 1998; pp. 3986-3990.

"Enhanced Genome Annotation Using Structural Profiles in the Program 3D-PSSM"; Authors: Lawrence A. Kelley, et al.; J. Mol. Biol.; vol. 299; 2000; pp. 499-520.

"Computational EST Database Analysis Identifies a Novel Member of the Neuropoietic Cytokine Family"; Authors: Y. Shi, et al.; Biochemical and Biophysical Research Communications; vol. 262; 1999; pp. 132-138.

"A Family of Candidate Taste Receptors in Human and Mouse"; Authors: Hiroaki Matsunami, et al.; Nature; vol. 404; Apr. 6, 2000; pp. 601-604.

"Transformation of Mammalian Cells to Antibiotic Resistance with a Bacterial Gene Under Control of the SV40 Early Region Promoter"; Authors: P.J. Southern, et al.; Journal of Molecular and Applied Genetics; vol. 1; 1982; pp. 327-341.

"Nonchromosomal Antibiotic Resistance in Bacteria: Genetic Transformation of Escherichia coli by R-Factor DNA"; Authors: Stanley H. Cohen, et al.; Proc. Nat. Acad. Sci. USA; vol. 69; No. 8; Aug. 1972; pp. 2110-2114.

"A New Technique for the Assay of Infectivity of Human Adenovirus 5 DNA"; Authors: F.L. Graham, et al.; Virology; vol. 52; 1973; pp. 456-467.

"DNA-Mediated Transfer of the Adenine Phosphoribosyltransferase Locus into Mammalian Cells"; Authors: Michael Wigler, et al.; Proc. Natl. Acad. Sci. USA: vol. 76; No. 3; Mar. 1979; pp. 1373-1376.

"Detection of Specific Sequences Among DNA Fragments Separated by Gel Electrophoresis"; Author: E.M. Southern; Journal of Molecular Biology; vol. 98; 1975; pp. 503-517.

Comparison of Oligonucleotide and Long DNA Fragments as Probes in DNA and RNA Dot, Southern, Northern, Colony and Plaque Hybridizations; Authors: Susan L. Berent, et al.; Bio Techniques; May/Jun. 1985; pp. 208-220.

"Reporter Genes: Application to the Study of Mammalian Gene Transcription"; Author: Jawed Alam, et al.; Analytical Biochemistry; vol. 188; 1990; pp. 245-254.

"RNase Protection Assay"; Authors: Ying Jun Ma, et al.; Methods: A Companion to Methods in Enzymology; vol. 10; Article 0102; 1996; pp. 273-278.

"Continuous Cultures of Fused Cells Secreting Antibody of Predefined Specificity"; Authors: G. Kohler, et al.; Nature; vol. 256; Aug. 7, 1975; pp. 495-497.

"Peptides and Mimics, Design of Conformationally Constrained"; Authors: Victor J. Hruby, et al.; 1995; pp. 658-664.

Protein Interaction Cloning by Far-Western Screening of -Phage cDNA Expression Libraries; Authors: Shnichi Takayama, et al.; Methods in Molecular Biology; vol. 69; 1997; pp. 171-184.

"Mutational Analysis of the Epstein-Barr Virus Nuclear Antigen 2 by Far-Western Blotting and DNA-Binding Studies"; Authors: Christian Sauder, et al.; Journal of General Virology; vol. 77; 1996; pp. 991-996.

"Data-Directed Drug Design"; Author: John Hodgson; Bio/Technology; vol. 9; Jan. 1991; pp. 19-21.

"New 3-D Search and De Novo Design Techniques Aid Drug Development"; Author: Stu Borman; Science/Technology; C&EN; Aug. 10, 1992; pp. 18-26.

"The Prostate"; Authors: Paul J. Cozzi, et al.; Wiley-Liss, Inc.; vol. 53; 2002; pp. 95-100.

"Effiziente Selektionsmechanismen: Voraussetzung fur erfolgreiche Gentherapie"; Author: Michael Bitzer, et al.; vol. 127; 2002; pp. 31-32.

"The Wnt Family of Developmental Regulators"; Author: Andrew P. McMahon; ElsevierScience Publishers Ltd. (UK); vol. 8; No. 7; Jul. 1992; pp. 236-256.

"Advances in the Development of Non-Human Viral DNA-Vectors for Gene Delivery"; Authors; Peter Loser, et al.; Current Gene Therapy; vol. 2; 2002; pp. 161-171.

"Gene Therapy: Promises and Problems"; Authors: Alexander Pfeiffer, et al.; Annu. Rev. Genomics Hum. Genet.; vol. 2; 2001; pp. 177-211.

"Possibilities of Non-Viral Gene Transfer to Improve Cutaneous Wound Healing"; Authors: M.G. Jeschke, et al.; Current Gene Therapy; vol. 1; 2001; pp. 267-278.

"Receptor-Mediated Gene Delivery and Expression in Vivo"; Authors: George Y. Wu, et al.; The Journal of Biological Chemistry; vol. 263; No. 29; Oct. 15, 1988; pp. 14621-14624.

"Targeting Genes: Delivery and Persistent Expression of a Foreign Gene Driven by Mammalian Regulatory Elements in Vivo"; Authors: Catherine H. Wu, et al.; The Journal of Biological Chemistry; No. 264; No. 29; Oct. 15, 1989; pp. 16985-16987.

"Transgenesis in Nonmurine Species"; Authors: John J. Mullins, et al.; Hypertension; vol. 22; No. 4; Oct. 1993; pp. 630-633.

"Transgenic Technology: An Overview of Approaches Useful in Surgical Research"; Authors: D.R. Brenin, et al.; Surgical Oncology; vol. 6; No. 2; 1997; pp. 99-110.

"Quantitative Genetics of Transgenic Mice: Components of Phenotypic Variation in Body Weights and Weight Gains"; Authors: A.C. Clutter, et al.; Genetics; vol. 143; Aug. 1996; pp. 1753-1760.

"Engineered Mouse Mimics Human Antibody Response"; Author: Michael McCarthy; The Lancet; vol. 349; Feb. 8, 1997; p. 405.

"Development of a Positive Method for Male Stem Cell-Mediated Gene Transfer in Mouse and Pig"; Authors: Jin-Hoi Kim, et al.; Molecular Reproduction and Development; vol. 46; 1997; pp. 515-526.

"The Production of Pharmaceutical Proteins From the Milk of Transgenic Animals"; Author: LM Houdebine; Reprod. Nutr. Dev.; vol. 35; 1995; pp. 609-617.

"Transgenic Livestock as Genetic Models of Human Disease"; Author: Robert M. Petters; Reprod. Fertil. Dev.; vol. 6; 1994; pp. 643-645.

"Human Factor IX Transgenic Sheep Produced by Transfer of Nuclei From Transfected Fetal Fibroblasts"; Authors: Angelika E. Schnieke, et al.; Science; vol. 278; Dec. 19, 1997; pp. 2130-2133.

Neurotractin, a Novel Neurite Outgrowth-Promoting; Ig-Like Protein that Interacts with CEPU-1 and LAMP; Authors: Andreas Marg, et al.; The Journal of Cell Biology; vol. 145; No. 4; May 17, 1999; pp. 865-876.

Expression of the IgLON Cell Adhesion Molecules Kilon and OBCAM in Hypothalamic Magnocellular Neurons; Authors: Seiji Miyata, et al.; The Journal of Comparative Neurology; vol. 424; 2000; p. 74-85.

"Biotechnological Advances in Goat Reproduction"; Authors: E. A. Amoah, et al.; J. Anim. Sci.; 1997; pp. 578-585.

"Genome-Wide Expression Monitoring in Saccharomyces cerevisiae"; Authors: Lisa Wodicka, et al.; Nature BioTechnology; vol. 15; Dec. 1997; pp. 1359-1367.

"A Simple Method for Displaying the Hydropathic Character of a Protein"; Authors: Jack Kyte, et al.; Journal of Molecular Biology; vol. 157; 1982; pp. 105-132.

"Identification of a Human RasGAP-related Protein Containing Calmodulin-binding Motifs"; Authors: Lawrence Weissbach et al.; The Journal of Biological Chemistry; vol. 269; No. 32; Aug. 12, 1994; pp. 20517-20521.

The Ras GTPase-Activating-Protein-Related Human Protein IQGAP2 Harbors a Potential Actin Binding Domain and Interacts with Calmodulin and Rho Family GTPases; Authors: Suzanne Brill, et al.; Molecular and Cellular Biology; Sep. 1996; pp. 4869-4878.

"Characterization of the Association of the Actin-binding Protein, IQGAP, and Activated Cdc42 with Golgi Membranes"; Authors: Sandra J. McCallum, et al.; The Journal of Biological Chemistry; vol. 273; No. 35; Aug. 28, 1998; pp. 22537-22544.

"Gastric Hyperplasia in Mice Lacking the Putative Cdc42 Effector IQGAP1"; Authors: Shihong Li, et al.; Molecular and Cellular Biology; vol. 20; No. 2; Jan. 2000; pp. 697-701.

"Scavenger Receptors in Innate Immunity"; Authors: Leanne Peiser, et al.; Current Opinion in Immunology; vol. 14; 2002; pp. 123-128.

"The SRCR Superfamily: A Family Reminiscent of the Ig Superfamily"; Authors: Resnick, et al.; Frontlines; TIBS 19; Jan. 1994; pp. 5-8.

"The Proton-Linked Monocarboxylate Transporter (MCT) Family: Structure, Function and Regulation"; Authors: Andrew Halestrap, et al.; Biochem J.; vol. 343; 1999; pp. 281-299.

Characterization of a Novel Rate Brain Glycosylphosphatidylinositol-Anchored Protein (Kilon), a Member of the IgLON Cell Adhesion Molecule Family; Authors: Nobuo Funatsu, et al.; The Journal of Biological Chemistry; vol. 274; No. 12; Mar. 19, 1999; pp. 8224-8230.

"Phosphorylation of Nucleosides and Nucleoside Analogs by Mammalian Nucleoside Monophosphate Kinases"; Authors: An R. Van Rompay, et al.; Pharmacology & Therapeutics; vol. 87; 2000; pp. 189-198.

"Sharpin, a Novel Postsynaptic Density Protein that Directly Interacts with the Shank Family of Proteins"; Authors: Sangmi Lim, et al.; Molecular and Cellular Neuroscience; vol. 17; 2001; pp. 385-397.

"The Shank Family of Scaffold Proteins"; Authors: Morgan Sheng, et al.; Journal of Cell Science; vol. 113; 2000; pp. 1851-1856.

"Identification of an Actin Cytoskeletal Complex That Includesf IQGAP and the Cdc42 GTPase"; Authors: Jon W. Erickson, et al.; The Journal of Biological Chemistry; vol. 272; No. 39; 1997; pp. 24443-24447.

"Identification of IQGAP as a Putative Target for the Small GTPases, Cdc42 and Rac1"; Authors: Shinya Kuroda, et al.; The Journal of Biological Chemistry; vol. 271; No. 38; Sep. 20, 1996; pp. 23363-23367.

IQGAP1-Mediated Stimulation of Transcriptional Co-Activation by B-Catenin Is Modulated by Calmodulin; Authors: Michael W. Briggs, et al.; The Journal of Biological Chemistry; vol. 277; No. 9; 2002; pp. 7453-7465.

"A Unique Member of the Thymidylate Kinase Family That Is Induced During Macrophage Activation"; Authors: Caroline G.L. Lee, et al.; The Journal of Immunology; vol. 154; 1995; pp. 6094-6102.

* cited by examiner

SEQUENCE LISTING

<160> NUMBER OF SEQ ID NOS: 56

<210> SEQ ID NO 1
<211> LENGTH: 5293
<212> TYPE: DNA
<213> ORGANISM: Homo sapiens
<220> FEATURE:
<221> NAME/KEY: CDS
<222> LOCATION: (390)..(4880)
<223> OTHER INFORMATION: LBFL109 Clone A

<400> SEQUENCE: 1

```
gtcctgtctg gcggtgccga cggtgagggg cggtggccca acggcgggag attcaaacct    60
ggaagaagga ggaacatgga gaggagagca gcgggcccag gctgggcagc ctctggatcg   120
aggcctgcct gaaggaggag cttccttccc cggtggagct ggaggagagc cttcggaatg   180
gagtgctgct ggccaagctg ggccactgtt ttgcaccctc cgtggttccg ttgaagaaga   240
tctacgatgt ggagcagctg cggtaccagg caactggctt acatttccgt cacacagaca   300
acatcaactt tggctatct gcaatagccc acatcggtct gccttcgacc ttcttcccag   360
agaccacgga catctatgac aaaaagaac atg ccc cgg gta gtc tac tgc atc    413
                                 Met Pro Arg Val Val Tyr Cys Ile
                                  1               5 cat gct ctc agt ctc ttc ctc ttc cgg ctg gga ttg gcc cct cag ata     461
His Ala Leu Ser Leu Phe Leu Phe Arg Leu Gly Leu Ala Pro Gln Ile
 10                  15                  20 cat gat cta tac ggg aaa gtg aaa ttc aca gct gag gaa ctc agc aac     509
His Asp Leu Tyr Gly Lys Val Lys Phe Thr Ala Glu Glu Leu Ser Asn
 25                  30                  35                  40 atg gcg tcc gaa ctg gcc aaa tat ggc ctc cag ctg cct gcc ttc agc     557
Met Ala Ser Glu Leu Ala Lys Tyr Gly Leu Gln Leu Pro Ala Phe Ser
                 45                  50                  55 aag atc ggg ggc atc ttg gcc aat gag ctc tcg gtg gat gag gct gca     605
Lys Ile Gly Gly Ile Leu Ala Asn Glu Leu Ser Val Asp Glu Ala Ala
             60                  65                  70 gtc cat gca gct gtt ctt gcc atc aat gaa gca gtg gag cga ggg gtg     653
Val His Ala Ala Val Leu Ala Ile Asn Glu Ala Val Glu Arg Gly Val
         75                  80                  85 gtg gag gac acc ctg gct gcc ttg cag aat ccc agt gct ctt ctg gag     701
Val Glu Asp Thr Leu Ala Ala Leu Gln Asn Pro Ser Ala Leu Leu Glu
     90                  95                 100 aat ctc cga gag cct ctg gca gcc gtc tac cag gag atg ctg gcc cag     749
Asn Leu Arg Glu Pro Leu Ala Ala Val Tyr Gln Glu Met Leu Ala Gln
105                 110                 115                 120 gcc aag atg gag aag gca gcc aat gcc agg aac cat gat gac aga gaa     797
Ala Lys Met Glu Lys Ala Ala Asn Ala Arg Asn His Asp Asp Arg Glu
                125                 130                 135 agc cag gac atc tat gac cac tac cta act cag gct gaa atc cag ggc     845
Ser Gln Asp Ile Tyr Asp His Tyr Leu Thr Gln Ala Glu Ile Gln Gly
            140                 145                 150 aat atc aac cat gtc aac gtc cat ggg gct cta gaa gtt gtt gat gat     893
Asn Ile Asn His Val Asn Val His Gly Ala Leu Glu Val Val Asp Asp
        155                 160                 165 gcc ctg gaa aga cag agc cct gaa gcc ttg ctc aag gcc ctt caa gac     941
Ala Leu Glu Arg Gln Ser Pro Glu Ala Leu Leu Lys Ala Leu Gln Asp
    170                 175                 180 cct gcc ctg gcc ctg cga ggg gtg agg aga gac ttt gct gac tgg tac     989
Pro Ala Leu Ala Leu Arg Gly Val Arg Arg Asp Phe Ala Asp Trp Tyr
185                 190                 195                 200
```

```
ctg gag cag ctg aac tca gac aga gag cag aag gca cag gag ctg ggc      1037
Leu Glu Gln Leu Asn Ser Asp Arg Glu Gln Lys Ala Gln Glu Leu Gly
            205                 210                 215 ctg gtg gag ctt ctg gaa aag gag gaa gtc cag gct ggt gtg gct gca      1085
Leu Val Glu Leu Leu Glu Lys Glu Glu Val Gln Ala Gly Val Ala Ala
        220                 225                 230 gcc aac aca aag ggt gat cag gaa caa gcc atg ctc cac gct gtg cag      1133
Ala Asn Thr Lys Gly Asp Gln Glu Gln Ala Met Leu His Ala Val Gln
    235                 240                 245 cgg atc aac aaa gcc atc cgg agg gga gtg gcg gct gac act gtg aag      1181
Arg Ile Asn Lys Ala Ile Arg Arg Gly Val Ala Ala Asp Thr Val Lys
250                 255                 260 gag ctg atg tgc cct gag gcc cag ctg cct cca gtg tac cct gtt gca      1229
Glu Leu Met Cys Pro Glu Ala Gln Leu Pro Pro Val Tyr Pro Val Ala
265                 270                 275                 280 tcg tct atg tac cag ctg gag ctg gca gtg ctc cag cag cag cag ggg      1277
Ser Ser Met Tyr Gln Leu Glu Leu Ala Val Leu Gln Gln Gln Gln Gly
            285                 290                 295 gag ctt ggc cag gag gag ctc ttc gtg gct gtg gag atg ctc tca gct      1325
Glu Leu Gly Gln Glu Glu Leu Phe Val Ala Val Glu Met Leu Ser Ala
        300                 305                 310 gtg gtc ctg att aac cgg gcc ctg gag gcc cgg gat gcc agt ggc ttc      1373
Val Val Leu Ile Asn Arg Ala Leu Glu Ala Arg Asp Ala Ser Gly Phe
    315                 320                 325 tgg agc agc ctg gtg aac cct gcc aca ggc ctg gct gag gtg gaa gga      1421
Trp Ser Ser Leu Val Asn Pro Ala Thr Gly Leu Ala Glu Val Glu Gly
330                 335                 340 gaa aat gcc cag cgt tac ttc gat gcc ctg ctg aaa ttg cga cag gag      1469
Glu Asn Ala Gln Arg Tyr Phe Asp Ala Leu Leu Lys Leu Arg Gln Glu
345                 350                 355                 360 cgt ggg atg ggt gag gac ttc ctg agc tgg aat gac ctg cag gcc acc      1517
Arg Gly Met Gly Glu Asp Phe Leu Ser Trp Asn Asp Leu Gln Ala Thr
            365                 370                 375 gtg agc cag gtc aat gca cag acc cag gaa gag act gac cgg gtc ctt      1565
Val Ser Gln Val Asn Ala Gln Thr Gln Glu Glu Thr Asp Arg Val Leu
        380                 385                 390 gca gtc agc ctc atc aat gag gct ctg gac aaa ggc agc cct gag aag      1613
Ala Val Ser Leu Ile Asn Glu Ala Leu Asp Lys Gly Ser Pro Glu Lys
    395                 400                 405 act ctg tct gcc cta ctg ctt cct gca gct ggc cta gat gat gtc agc      1661
Thr Leu Ser Ala Leu Leu Leu Pro Ala Ala Gly Leu Asp Asp Val Ser
410                 415                 420 ctc cct gtc gcc cct cgg tac cat ctc ctc ctt gtg gca gcc aaa agg      1709
Leu Pro Val Ala Pro Arg Tyr His Leu Leu Leu Val Ala Ala Lys Arg
425                 430                 435                 440 cag aag gcc cag gtg aca ggg gat cct gga gct gtg ctg tgg ctt gag      1757
Gln Lys Ala Gln Val Thr Gly Asp Pro Gly Ala Val Leu Trp Leu Glu
            445                 450                 455 gag atc cgc cag gga gtg gtc aga gcc aac cag gac act aat aca gct      1805
Glu Ile Arg Gln Gly Val Val Arg Ala Asn Gln Asp Thr Asn Thr Ala
        460                 465                 470 cag aga atg gct ctt ggt gtg gct gcc atc aat caa gcc atc aag gag      1853
Gln Arg Met Ala Leu Gly Val Ala Ala Ile Asn Gln Ala Ile Lys Glu
    475                 480                 485 ggc aag gca gcc cag act gag cgg gtg ttg agg aac ccc gca gtg gcc      1901
Gly Lys Ala Ala Gln Thr Glu Arg Val Leu Arg Asn Pro Ala Val Ala
490                 495                 500 ctt cga ggg gta gtt ccc gac tgt gcc aac ggc tac cag cga gcc ctg      1949
Leu Arg Gly Val Val Pro Asp Cys Ala Asn Gly Tyr Gln Arg Ala Leu
```

```
                505                 510                 515                 520
gaa agt gcc atg gca aag aaa cag cgt cca gca gac aca gct ttc tgg      1997
Glu Ser Ala Met Ala Lys Lys Gln Arg Pro Ala Asp Thr Ala Phe Trp
            525                 530                 535 gtt caa cat gac atg aag gat ggc act gcc tac tac ttc cat ctg cag      2045
Val Gln His Asp Met Lys Asp Gly Thr Ala Tyr Tyr Phe His Leu Gln
            540                 545                 550 acc ttc cag ggg atc tgg gag caa cct cct ggc tgc ccc ctc aac acc      2093
Thr Phe Gln Gly Ile Trp Glu Gln Pro Pro Gly Cys Pro Leu Asn Thr
            555                 560                 565 tct cac ctg acc cgg gag gag atc cag tca gct gtc acc aag gtc act      2141
Ser His Leu Thr Arg Glu Glu Ile Gln Ser Ala Val Thr Lys Val Thr
            570                 575                 580 gct gcc tat gac cgc caa cag ctc tgg aaa gcc aac gtc ggc ttt gtt      2189
Ala Ala Tyr Asp Arg Gln Gln Leu Trp Lys Ala Asn Val Gly Phe Val
585                 590                 595                 600 atc cag ctc cag gcc cgc ctc cgt ggc ttc cta gtt cgg cag aag ttt      2237
Ile Gln Leu Gln Ala Arg Leu Arg Gly Phe Leu Val Arg Gln Lys Phe
            605                 610                 615 gct gag cat tcc cac ttt ctg agg acc tgg ctc cca gca gtc atc aag      2285
Ala Glu His Ser His Phe Leu Arg Thr Trp Leu Pro Ala Val Ile Lys
            620                 625                 630 atc cag gct cat tgg cgg ggt tat agg cag cgg aag att tac ctg gag      2333
Ile Gln Ala His Trp Arg Gly Tyr Arg Gln Arg Lys Ile Tyr Leu Glu
            635                 640                 645 tgg ttg cag tat ttt aaa gca aac ctg gat gcc ata atc aag atc cag      2381
Trp Leu Gln Tyr Phe Lys Ala Asn Leu Asp Ala Ile Ile Lys Ile Gln
650                 655                 660 gcc tgg gcc cgg atg tgg gca gct cgg agg caa tac ctg agg cgt ctg      2429
Ala Trp Ala Arg Met Trp Ala Ala Arg Arg Gln Tyr Leu Arg Arg Leu
665                 670                 675                 680 cac tac ttc cag aag aat gtt aac tcc att gtg aag atc cag gca ttt      2477
His Tyr Phe Gln Lys Asn Val Asn Ser Ile Val Lys Ile Gln Ala Phe
            685                 690                 695 ttc cga gcc agg aaa gcc caa gat gac tac agg ata tta gtg cat gca      2525
Phe Arg Ala Arg Lys Ala Gln Asp Asp Tyr Arg Ile Leu Val His Ala
            700                 705                 710 ccc cac cct cct ctc agt gtg gta cgc aga ttt gcc cat ctc ttg aat      2573
Pro His Pro Pro Leu Ser Val Val Arg Arg Phe Ala His Leu Leu Asn
            715                 720                 725 caa agc cag caa gac ttc ttg gct gag gca gag ctg ctg aag ctc cag      2621
Gln Ser Gln Gln Asp Phe Leu Ala Glu Ala Glu Leu Leu Lys Leu Gln
            730                 735                 740 gaa gag gta gtt agg aag atc cga tcc aat cag cag ctg gag cag gac      2669
Glu Glu Val Val Arg Lys Ile Arg Ser Asn Gln Gln Leu Glu Gln Asp
745                 750                 755                 760 ctc aac atc atg gac atc aag att ggc ctg ctg gtg aag aac cgg atc      2717
Leu Asn Ile Met Asp Ile Lys Ile Gly Leu Leu Val Lys Asn Arg Ile
            765                 770                 775 act ctg cag gaa gtg gtc tcc cac tgc aag aag ctg acc aag agg aat      2765
Thr Leu Gln Glu Val Val Ser His Cys Lys Lys Leu Thr Lys Arg Asn
            780                 785                 790 aag gaa cag ctg tca gat atg atg gtt ctg gac aag cag aag ggt tta      2813
Lys Glu Gln Leu Ser Asp Met Met Val Leu Asp Lys Gln Lys Gly Leu
            795                 800                 805 aag tcg ctg agc aaa gag aaa cgg cag aaa cta gaa gca tac caa cac      2861
Lys Ser Leu Ser Lys Glu Lys Arg Gln Lys Leu Glu Ala Tyr Gln His
            810                 815                 820 ctc ttc tac ctg ctc cag act cag ccc atc tac ctg gcc aag ctg atc      2909
Leu Phe Tyr Leu Leu Gln Thr Gln Pro Ile Tyr Leu Ala Lys Leu Ile
```

```
Leu Phe Tyr Leu Leu Gln Thr Gln Pro Ile Tyr Leu Ala Lys Leu Ile
825                 830                 835                 840 ttt cag atg cca cag aac aaa acc acc aag ttc atg gag gca gtg att    2957
Phe Gln Met Pro Gln Asn Lys Thr Thr Lys Phe Met Glu Ala Val Ile
                845                 850                 855 ttc agc ctg tac aac tat gcc tcc agc cgc cga gag gcc tat ctc ctg    3005
Phe Ser Leu Tyr Asn Tyr Ala Ser Ser Arg Arg Glu Ala Tyr Leu Leu
            860                 865                 870 ctc cag ctg ttc aag aca gca ctc cag gag gaa atc aag tca aag gtg    3053
Leu Gln Leu Phe Lys Thr Ala Leu Gln Glu Glu Ile Lys Ser Lys Val
        875                 880                 885 gag cag ccc cag gac gtg gtg aca ggc aac cca aca gtg gtg agg ctg    3101
Glu Gln Pro Gln Asp Val Val Thr Gly Asn Pro Thr Val Val Arg Leu
    890                 895                 900 gtg gtg aga ttc tac cgt aat ggg cgg gga cag agt gcc ctg cag gag    3149
Val Val Arg Phe Tyr Arg Asn Gly Arg Gly Gln Ser Ala Leu Gln Glu
905                 910                 915                 920 att ctg ggc aag gtt atc cag gat gtg cta gaa gac aaa gtg ctc agc    3197
Ile Leu Gly Lys Val Ile Gln Asp Val Leu Glu Asp Lys Val Leu Ser
                925                 930                 935 gtc cac aca gac cct gtc cac ctc tat aag aac tgg atc aac cag act    3245
Val His Thr Asp Pro Val His Leu Tyr Lys Asn Trp Ile Asn Gln Thr
            940                 945                 950 gag gcc cag aca ggg cag cgc agc cat ctc cca tat gat gtc acc ccg    3293
Glu Ala Gln Thr Gly Gln Arg Ser His Leu Pro Tyr Asp Val Thr Pro
        955                 960                 965 gag cag gcc ttg agc cac ccc gag gtc cag aga cga ctg gac atc gcc    3341
Glu Gln Ala Leu Ser His Pro Glu Val Gln Arg Arg Leu Asp Ile Ala
    970                 975                 980 cta cgc aac ctc ctc gcc atg act gat aag ttc ctt tta gcc atc acc    3389
Leu Arg Asn Leu Leu Ala Met Thr Asp Lys Phe Leu Leu Ala Ile Thr
985                 990                 995                 1000 tca tct gtg gac caa att ccg tat ggg atg cga tat gtg gcc aaa gtc    3437
Ser Ser Val Asp Gln Ile Pro Tyr Gly Met Arg Tyr Val Ala Lys Val
                1005                1010                1015 ctg aag gca act ctg gca gag aaa ttc cct gac gcc aca gac agc gag    3485
Leu Lys Ala Thr Leu Ala Glu Lys Phe Pro Asp Ala Thr Asp Ser Glu
            1020                1025                1030 gtc tat aag gtg gtc ggg aac ctc ctg tac tac cgc ttc ctg aac cca    3533
Val Tyr Lys Val Val Gly Asn Leu Leu Tyr Tyr Arg Phe Leu Asn Pro
        1035                1040                1045 gct gtg gtg gct cct gac gcc ttc gac att gtg gcc atg gca gct ggt    3581
Ala Val Val Ala Pro Asp Ala Phe Asp Ile Val Ala Met Ala Ala Gly
    1050                1055                1060 gga gcc ctg gct gcc ccc cag cgc cat gcc ctg ggg gct gtg gct cag    3629
Gly Ala Leu Ala Ala Pro Gln Arg His Ala Leu Gly Ala Val Ala Gln
1065                1070                1075                1080 ctc cta cag cac gct gcg gct ggc aag gcc ttc tct ggg cag agc cag    3677
Leu Leu Gln His Ala Ala Ala Gly Lys Ala Phe Ser Gly Gln Ser Gln
                1085                1090                1095 cac cta cgg gtc ctg aat gac tat ctg gag gaa aca cac ctc aag ttc    3725
His Leu Arg Val Leu Asn Asp Tyr Leu Glu Glu Thr His Leu Lys Phe
            1100                1105                1110 agg aag ttc atc cat aga gcc tgc cag gtg cca gag cca gag gag cgt    3773
Arg Lys Phe Ile His Arg Ala Cys Gln Val Pro Glu Pro Glu Glu Arg
        1115                1120                1125 ttt gca gtg gac gag tac tca gac atg gtg gct gtg gcc aaa ccc atg    3821
Phe Ala Val Asp Glu Tyr Ser Asp Met Val Ala Val Ala Lys Pro Met
    1130                1135                1140
```

-continued

| | |
|---|---|
| gtg tac atc acc gtg ggg gag ctg gtc aac acg cac agg ctg ttg ctg<br>Val Tyr Ile Thr Val Gly Glu Leu Val Asn Thr His Arg Leu Leu Leu<br>1145                    1150                    1155                    1160 | 3869 |
| gag cac cag gac tgc att gcc cct gat cac caa gac ccc ctg cat gag<br>Glu His Gln Asp Cys Ile Ala Pro Asp His Gln Asp Pro Leu His Glu<br>                1165                    1170                    1175 | 3917 |
| ctc ctg gag gat ctt ggg gag ctg ccc acc atc cct gac ctt att ggt<br>Leu Leu Glu Asp Leu Gly Glu Leu Pro Thr Ile Pro Asp Leu Ile Gly<br>                    1180                    1185                    1190 | 3965 |
| gag agc atc gct gca gat ggg cac aca gac ctg agc aag cta gaa gtg<br>Glu Ser Ile Ala Ala Asp Gly His Thr Asp Leu Ser Lys Leu Glu Val<br>            1195                    1200                    1205 | 4013 |
| tcc ctg acg ctg acc aac aag ttt gaa gga cta gag gca gat gct gat<br>Ser Leu Thr Leu Thr Asn Lys Phe Glu Gly Leu Glu Ala Asp Ala Asp<br>1210                    1215                    1220 | 4061 |
| gac tcc aac acc cgt agc ctg ctt ctg agc acc aag cag ctg ttg gcc<br>Asp Ser Asn Thr Arg Ser Leu Leu Leu Ser Thr Lys Gln Leu Leu Ala<br>1225                    1230                    1235                    1240 | 4109 |
| gat atc ata cag ttc cat cct ggg gac acc ctc aag gag atc ctg tcc<br>Asp Ile Ile Gln Phe His Pro Gly Asp Thr Leu Lys Glu Ile Leu Ser<br>                    1245                    1250                    1255 | 4157 |
| ctc tcg gct tcc aga gag caa gaa gca gcc cac aag cag ctg atg agc<br>Leu Ser Ala Ser Arg Glu Gln Glu Ala Ala His Lys Gln Leu Met Ser<br>            1260                    1265                    1270 | 4205 |
| cga cgc cag gcc tgt aca gcc cag aca ccg gag cca ctg cga cga cac<br>Arg Arg Gln Ala Cys Thr Ala Gln Thr Pro Glu Pro Leu Arg Arg His<br>                1275                    1280                    1285 | 4253 |
| cgc tca ctg aca gct cac tcc ctc ctg cca ctg gca gag aag cag cgg<br>Arg Ser Leu Thr Ala His Ser Leu Leu Pro Leu Ala Glu Lys Gln Arg<br>    1290                    1295                    1300 | 4301 |
| cgc gtc ctg cgg aac ctg cgc cga ctt gaa gcc ctg ggg ttg gtc agc<br>Arg Val Leu Arg Asn Leu Arg Arg Leu Glu Ala Leu Gly Leu Val Ser<br>1305                    1310                    1315                    1320 | 4349 |
| gcc aga aat ggc tac cag ggg cta gtg gac gag ctg gcc aag gac atc<br>Ala Arg Asn Gly Tyr Gln Gly Leu Val Asp Glu Leu Ala Lys Asp Ile<br>                1325                    1330                    1335 | 4397 |
| cgc aac cag cac aga cac agg cac agg cgg aag gca gag ctg gtg aag<br>Arg Asn Gln His Arg His Arg His Arg Arg Lys Ala Glu Leu Val Lys<br>            1340                    1345                    1350 | 4445 |
| ctg cag gcc aca tta cag ggc ctg agc act aag acc acc ttc tat gag<br>Leu Gln Ala Thr Leu Gln Gly Leu Ser Thr Lys Thr Thr Phe Tyr Glu<br>        1355                    1360                    1365 | 4493 |
| gag cag ggt gac tac tac agc cag tac atc cgg gcc tgc ctg gac cac<br>Glu Gln Gly Asp Tyr Tyr Ser Gln Tyr Ile Arg Ala Cys Leu Asp His<br>1370                      1375                    1380 | 4541 |
| ctg gcc ccc gac tcc aag agt tct ggg aag ggg aag aag cag cct tct<br>Leu Ala Pro Asp Ser Lys Ser Ser Gly Lys Gly Lys Lys Gln Pro Ser<br>1385                    1390                    1395                    1400 | 4589 |
| ctt cat tac act gct gct cag ctc ctg gaa aag ggt gtc ttg gtg gaa<br>Leu His Tyr Thr Ala Ala Gln Leu Leu Glu Lys Gly Val Leu Val Glu<br>                1405                    1410                    1415 | 4637 |
| att gaa gat ctt ccc gcc tct cac ttc aga aac gtc atc ttt gac atc<br>Ile Glu Asp Leu Pro Ala Ser His Phe Arg Asn Val Ile Phe Asp Ile<br>            1420                    1425                    1430 | 4685 |
| acg ccg gga gat gag gca gga aag ttt gaa gta aat gcc aag ttc ctg<br>Thr Pro Gly Asp Glu Ala Gly Lys Phe Glu Val Asn Ala Lys Phe Leu<br>        1435                    1440                    1445 | 4733 |
| ggt gtg gac atg gag cga ttt cag ctt cac tat cag gat ctc ctg cag<br>Gly Val Asp Met Glu Arg Phe Gln Leu His Tyr Gln Asp Leu Leu Gln<br>1450                    1455                    1460 | 4781 |

-continued

```
ctc cag tat gag ggt gtg gct gtc atg aaa ctc ttc aac aag gcc aaa      4829
Leu Gln Tyr Glu Gly Val Ala Val Met Lys Leu Phe Asn Lys Ala Lys
1465                1470                1475                1480 gtc aat gtc aac ctt ctc atc ttc ctc ctc aac aag aag ttt ttg cgg      4877
Val Asn Val Asn Leu Leu Ile Phe Leu Leu Asn Lys Lys Phe Leu Arg
                1485                1490                1495 aag     tgacagaggc aaagggtgct acccaagccc ctcttacctc tctggatgct       4930
Lys ttctttaaca ctaactcacc actgtgcttc cctgcagaca cccagagctc aggactgggc    4990
aaggcccagg gattctcacc ccttccccag ctgggaggag cttgcctgcc tggccacaga    5050
cagtgtatct tctaattggc taaagtgggc cttgcccaga gtccagctgt gtggctttta   5110
tcatgcatga caaacccctg gctttcctgc cagatggatt ctcatccctt acagctgact   5170
cttccaggca atttccatag atctgcagtc ctgcctctgc cacagtctct ctgttgtccc   5230
cacatctacc caacttcctg tactgttgcc cttctgatgt taataaaagc agctgttact   5290
ccc                                                                  5293
```

<210> SEQ ID NO 2
<211> LENGTH: 1497
<212> TYPE: PRT
<213> ORGANISM: Homo sapiens

<400> SEQUENCE: 2

```
Met Pro Arg Val Val Tyr Cys Ile His Ala Leu Ser Leu Phe Leu Phe
1               5                   10                  15

Arg Leu Gly Leu Ala Pro Gln Ile His Asp Leu Tyr Gly Lys Val Lys
                20                  25                  30

Phe Thr Ala Glu Glu Leu Ser Asn Met Ala Ser Glu Leu Ala Lys Tyr
            35                  40                  45

Gly Leu Gln Leu Pro Ala Phe Ser Lys Ile Gly Gly Ile Leu Ala Asn
        50                  55                  60

Glu Leu Ser Val Asp Glu Ala Ala Val His Ala Val Leu Ala Ile
65                  70                  75                  80

Asn Glu Ala Val Glu Arg Gly Val Val Glu Asp Thr Leu Ala Ala Leu
                85                  90                  95

Gln Asn Pro Ser Ala Leu Leu Glu Asn Leu Arg Glu Pro Leu Ala Ala
            100                 105                 110

Val Tyr Gln Glu Met Leu Ala Gln Ala Lys Met Glu Lys Ala Ala Asn
        115                 120                 125

Ala Arg Asn His Asp Asp Arg Glu Ser Gln Asp Ile Tyr Asp His Tyr
    130                 135                 140

Leu Thr Gln Ala Glu Ile Gln Gly Asn Ile Asn His Val Asn Val His
145                 150                 155                 160

Gly Ala Leu Glu Val Val Asp Asp Ala Leu Glu Arg Gln Ser Pro Glu
                165                 170                 175

Ala Leu Leu Lys Ala Leu Gln Asp Pro Ala Leu Ala Leu Arg Gly Val
            180                 185                 190

Arg Arg Asp Phe Ala Asp Trp Tyr Leu Glu Gln Leu Asn Ser Asp Arg
        195                 200                 205

Glu Gln Lys Ala Gln Glu Gly Leu Val Glu Leu Glu Lys
    210                 215                 220

Glu Val Gln Ala Gly Val Ala Ala Asn Thr Lys Gly Asp Gln Glu
225                 230                 235                 240
```

```
Gln Ala Met Leu His Ala Val Gln Arg Ile Asn Lys Ala Ile Arg Arg
            245                 250                 255
Gly Val Ala Ala Asp Thr Val Lys Glu Leu Met Cys Pro Glu Ala Gln
        260                 265                 270
Leu Pro Pro Val Tyr Pro Val Ala Ser Ser Met Tyr Gln Leu Glu Leu
        275                 280                 285
Ala Val Leu Gln Gln Gln Gly Glu Leu Gly Gln Glu Leu Phe
        290                 295                 300
Val Ala Val Glu Met Leu Ser Ala Val Val Leu Ile Asn Arg Ala Leu
305                 310                 315                 320
Glu Ala Arg Asp Ala Ser Gly Phe Trp Ser Ser Leu Val Asn Pro Ala
                325                 330                 335
Thr Gly Leu Ala Glu Val Glu Gly Glu Asn Ala Gln Arg Tyr Phe Asp
            340                 345                 350
Ala Leu Leu Lys Leu Arg Gln Glu Arg Gly Met Gly Glu Asp Phe Leu
        355                 360                 365
Ser Trp Asn Asp Leu Gln Ala Thr Val Ser Gln Val Asn Ala Gln Thr
        370                 375                 380
Gln Glu Glu Thr Asp Arg Val Leu Ala Val Ser Leu Ile Asn Glu Ala
385                 390                 395                 400
Leu Asp Lys Gly Ser Pro Glu Lys Thr Leu Ser Ala Leu Leu Leu Pro
                405                 410                 415
Ala Ala Gly Leu Asp Asp Val Ser Leu Pro Val Ala Pro Arg Tyr His
            420                 425                 430
Leu Leu Leu Val Ala Ala Lys Arg Gln Lys Ala Gln Val Thr Gly Asp
        435                 440                 445
Pro Gly Ala Val Leu Trp Leu Glu Glu Ile Arg Gln Gly Val Val Arg
        450                 455                 460
Ala Asn Gln Asp Thr Asn Thr Ala Gln Arg Met Ala Leu Gly Val Ala
465                 470                 475                 480
Ala Ile Asn Gln Ala Ile Lys Glu Gly Lys Ala Ala Gln Thr Glu Arg
                485                 490                 495
Val Leu Arg Asn Pro Ala Val Ala Leu Arg Gly Val Val Pro Asp Cys
            500                 505                 510
Ala Asn Gly Tyr Gln Arg Ala Leu Glu Ser Ala Met Ala Lys Lys Gln
        515                 520                 525
Arg Pro Ala Asp Thr Ala Phe Trp Val Gln His Asp Met Lys Asp Gly
        530                 535                 540
Thr Ala Tyr Tyr Phe His Leu Gln Thr Phe Gln Gly Ile Trp Glu Gln
545                 550                 555                 560
Pro Pro Gly Cys Pro Leu Asn Thr Ser His Leu Thr Arg Glu Glu Ile
                565                 570                 575
Gln Ser Ala Val Thr Lys Val Thr Ala Ala Tyr Asp Arg Gln Gln Leu
            580                 585                 590
Trp Lys Ala Asn Val Gly Phe Val Ile Gln Leu Gln Ala Arg Leu Arg
        595                 600                 605
Gly Phe Leu Val Arg Gln Lys Phe Ala Glu His Ser His Phe Leu Arg
        610                 615                 620
Thr Trp Leu Pro Ala Val Ile Lys Ile Gln Ala His Trp Arg Gly Tyr
625                 630                 635                 640
Arg Gln Arg Lys Ile Tyr Leu Glu Trp Leu Gln Tyr Phe Lys Ala Asn
                645                 650                 655
Leu Asp Ala Ile Ile Lys Ile Gln Ala Trp Ala Arg Met Trp Ala Ala
```

-continued

```
              660                 665                 670
Arg Arg Gln Tyr Leu Arg Arg Leu His Tyr Phe Gln Lys Asn Val Asn
              675                 680                 685

Ser Ile Val Lys Ile Gln Ala Phe Phe Arg Ala Arg Lys Ala Gln Asp
              690                 695                 700

Asp Tyr Arg Ile Leu Val His Ala Pro His Pro Pro Leu Ser Val Val
705                 710                 715                 720

Arg Arg Phe Ala His Leu Leu Asn Gln Ser Gln Gln Asp Phe Leu Ala
              725                 730                 735

Glu Ala Glu Leu Leu Lys Leu Gln Glu Glu Val Val Arg Lys Ile Arg
              740                 745                 750

Ser Asn Gln Gln Leu Glu Gln Asp Leu Asn Ile Met Asp Ile Lys Ile
              755                 760                 765

Gly Leu Leu Val Lys Asn Arg Ile Thr Leu Gln Glu Val Val Ser His
              770                 775                 780

Cys Lys Lys Leu Thr Lys Arg Asn Lys Glu Gln Leu Ser Asp Met Met
785                 790                 795                 800

Val Leu Asp Lys Gln Lys Gly Leu Lys Ser Leu Ser Lys Glu Lys Arg
              805                 810                 815

Gln Lys Leu Glu Ala Tyr Gln His Leu Phe Tyr Leu Leu Gln Thr Gln
              820                 825                 830

Pro Ile Tyr Leu Ala Lys Leu Ile Phe Gln Met Pro Gln Asn Lys Thr
              835                 840                 845

Thr Lys Phe Met Glu Ala Val Ile Phe Ser Leu Tyr Asn Tyr Ala Ser
              850                 855                 860

Ser Arg Arg Glu Ala Tyr Leu Leu Gln Leu Phe Lys Thr Ala Leu
865                 870                 875                 880

Gln Glu Glu Ile Lys Ser Lys Val Glu Gln Pro Gln Asp Val Val Thr
              885                 890                 895

Gly Asn Pro Thr Val Val Arg Leu Val Val Arg Phe Tyr Arg Asn Gly
              900                 905                 910

Arg Gly Gln Ser Ala Leu Gln Glu Ile Leu Gly Lys Val Ile Gln Asp
              915                 920                 925

Val Leu Glu Asp Lys Val Leu Ser Val His Thr Asp Pro Val His Leu
930                 935                 940

Tyr Lys Asn Trp Ile Asn Gln Thr Glu Ala Gln Thr Gly Gln Arg Ser
945                 950                 955                 960

His Leu Pro Tyr Asp Val Thr Pro Glu Gln Ala Leu Ser His Pro Glu
              965                 970                 975

Val Gln Arg Arg Leu Asp Ile Ala Leu Arg Asn Leu Leu Ala Met Thr
              980                 985                 990

Asp Lys Phe Leu Leu Ala Ile Thr Ser Ser Val Asp Gln Ile Pro Tyr
              995                 1000                1005

Gly Met Arg Tyr Val Ala Lys Val Leu Lys Ala Thr Leu Ala Glu Lys
              1010                1015                1020

Phe Pro Asp Ala Thr Asp Ser Glu Val Tyr Lys Val Val Gly Asn Leu
1025                1030                1035                1040

Leu Tyr Tyr Arg Phe Leu Asn Pro Ala Val Val Ala Pro Asp Ala Phe
              1045                1050                1055

Asp Ile Val Ala Met Ala Ala Gly Gly Ala Leu Ala Ala Pro Gln Arg
              1060                1065                1070

His Ala Leu Gly Ala Val Ala Gln Leu Leu Gln His Ala Ala Ala Gly
              1075                1080                1085
```

```
Lys Ala Phe Ser Gly Gln Ser Gln His Leu Arg Val Leu Asn Asp Tyr
    1090                1095                1100

Leu Glu Glu Thr His Leu Lys Phe Arg Lys Phe Ile His Arg Ala Cys
1105                1110                1115                1120

Gln Val Pro Glu Pro Glu Arg Phe Ala Val Asp Glu Tyr Ser Asp
            1125                1130                1135

Met Val Ala Val Ala Lys Pro Met Val Tyr Ile Thr Val Gly Glu Leu
        1140                1145                1150

Val Asn Thr His Arg Leu Leu Leu Glu His Gln Asp Cys Ile Ala Pro
    1155                1160                1165

Asp His Gln Asp Pro Leu His Glu Leu Leu Glu Asp Leu Gly Glu Leu
    1170                1175                1180

Pro Thr Ile Pro Asp Leu Ile Gly Glu Ser Ile Ala Ala Asp Gly His
1185                1190                1195                1200

Thr Asp Leu Ser Lys Leu Glu Val Ser Leu Thr Leu Thr Asn Lys Phe
                1205                1210                1215

Glu Gly Leu Glu Ala Asp Ala Asp Asp Ser Asn Thr Arg Ser Leu Leu
            1220                1225                1230

Leu Ser Thr Lys Gln Leu Leu Ala Asp Ile Ile Gln Phe His Pro Gly
        1235                1240                1245

Asp Thr Leu Lys Glu Ile Leu Ser Leu Ser Ala Ser Arg Glu Gln Glu
    1250                1255                1260

Ala Ala His Lys Gln Leu Met Ser Arg Arg Gln Ala Cys Thr Ala Gln
1265                1270                1275                1280

Thr Pro Glu Pro Leu Arg Arg His Arg Ser Leu Thr Ala His Ser Leu
                1285                1290                1295

Leu Pro Leu Ala Glu Lys Gln Arg Arg Val Leu Arg Asn Leu Arg Arg
            1300                1305                1310

Leu Glu Ala Leu Gly Leu Val Ser Ala Arg Asn Gly Tyr Gln Gly Leu
        1315                1320                1325

Val Asp Glu Leu Ala Lys Asp Ile Arg Asn Gln His Arg His Arg His
    1330                1335                1340

Arg Arg Lys Ala Glu Leu Val Lys Leu Gln Ala Thr Leu Gln Gly Leu
1345                1350                1355                1360

Ser Thr Lys Thr Thr Phe Tyr Glu Glu Gln Gly Asp Tyr Tyr Ser Gln
                1365                1370                1375

Tyr Ile Arg Ala Cys Leu Asp His Leu Ala Pro Asp Ser Lys Ser Ser
            1380                1385                1390

Gly Lys Gly Lys Lys Gln Pro Ser Leu His Tyr Thr Ala Ala Gln Leu
        1395                1400                1405

Leu Glu Lys Gly Val Leu Val Glu Ile Glu Asp Leu Pro Ala Ser His
    1410                1415                1420

Phe Arg Asn Val Ile Phe Asp Ile Thr Pro Gly Asp Glu Ala Gly Lys
1425                1430                1435                1440

Phe Glu Val Asn Ala Lys Phe Leu Gly Val Asp Met Glu Arg Phe Gln
                1445                1450                1455

Leu His Tyr Gln Asp Leu Leu Gln Leu Gln Tyr Glu Gly Val Ala Val
            1460                1465                1470

Met Lys Leu Phe Asn Lys Ala Lys Val Asn Val Asn Leu Leu Ile Phe
        1475                1480                1485

Leu Leu Asn Lys Lys Phe Leu Arg Lys
    1490                1495
```

```
<210> SEQ ID NO 3
<211> LENGTH: 5317
<212> TYPE: DNA
<213> ORGANISM: Homo sapiens
<220> FEATURE:
<221> NAME/KEY: CDS
<222> LOCATION: (12)..(4904)
<223> OTHER INFORMATION: LBFL109 Clone B

<400> SEQUENCE: 3
gaaggaggaa c     atg gag agg aga gca gcg ggc cca ggc tgg gca            44
                 Met Glu Arg Arg Ala Ala Gly Pro Gly Trp Ala
                 1               5                   10 gcc tat gaa cgc ctc aca gct gag gag atg gat gag cag agg cgg cag         92
Ala Tyr Glu Arg Leu Thr Ala Glu Glu Met Asp Glu Gln Arg Arg Gln
                15                  20                  25 aat gtt gcc tat cag tac ctg tgc cgg ctg gag gag gcc aag cgc tgg        140
Asn Val Ala Tyr Gln Tyr Leu Cys Arg Leu Glu Glu Ala Lys Arg Trp
        30                  35                  40 atg gag gcc tgc ctg aag gag gag ctt cct tcc ccg gtg gag ctg gag        188
Met Glu Ala Cys Leu Lys Glu Glu Leu Pro Ser Pro Val Glu Leu Glu
45                  50                  55 gag agc ctt cgg aat gga gtg ctg ctg gcc aag ctg ggc cac tgt ttt        236
Glu Ser Leu Arg Asn Gly Val Leu Leu Ala Lys Leu Gly His Cys Phe
            60                  65                  70                  75 gca ccc tcc gtg gtt ccg ttg aag aag atc tac gat gtg gag cag ctg        284
Ala Pro Ser Val Val Pro Leu Lys Lys Ile Tyr Asp Val Glu Gln Leu
                80                  85                  90 cgg tac cag gca act ggc tta cat ttc cgt cac aca gac aac atc aac        332
Arg Tyr Gln Ala Thr Gly Leu His Phe Arg His Thr Asp Asn Ile Asn
            95                  100                 105 ttt tgg cta tct gca ata gcc cac atc ggt ctg cct tcg acc ttc ttc        380
Phe Trp Leu Ser Ala Ile Ala His Ile Gly Leu Pro Ser Thr Phe Phe
        110                 115                 120 cca gag acc acg gac atc tat gac aaa aag aac atg ccc cgg gta gtc        428
Pro Glu Thr Thr Asp Ile Tyr Asp Lys Lys Asn Met Pro Arg Val Val
    125                 130                 135 tac tgc atc cat gct ctc agt ctc ttc ctc ttc cgg ctg gga ttg gcc        476
Tyr Cys Ile His Ala Leu Ser Leu Phe Leu Phe Arg Leu Gly Leu Ala
140                 145                 150                 155 cct cag ata cat gat cta tac ggg aaa gtg aaa ttc aca gct gag gaa        524
Pro Gln Ile His Asp Leu Tyr Gly Lys Val Lys Phe Thr Ala Glu Glu
                160                 165                 170 ctc agc aac atg gcg tcc gaa ctg gcc aaa tat ggc ctc cag ctg cct        572
Leu Ser Asn Met Ala Ser Glu Leu Ala Lys Tyr Gly Leu Gln Leu Pro
            175                 180                 185 gcc ttc agc aag atc ggg ggc atc ttg gcc aat gag ctc tcg gtg gat        620
Ala Phe Ser Lys Ile Gly Gly Ile Leu Ala Asn Glu Leu Ser Val Asp
        190                 195                 200 gag gct gca gtc cat gca gct gtt ctt gcc atc aat gaa gca gtg gag        668
Glu Ala Ala Val His Ala Ala Val Leu Ala Ile Asn Glu Ala Val Glu
    205                 210                 215 cga ggg gtg gtg gag gac acc ctg gct gcc ttg cag aat ccc agt gct        716
Arg Gly Val Val Glu Asp Thr Leu Ala Ala Leu Gln Asn Pro Ser Ala
220                 225                 230                 235 ctt ctg gag aat ctc cga gag cct ctg gca gcc gtc tac cag gag atg        764
Leu Leu Glu Asn Leu Arg Glu Pro Leu Ala Ala Val Tyr Gln Glu Met
                240                 245                 250 ctg gcc cag gcc aag atg gag aag gca gcc aat gcc agg aac cat gat        812
Leu Ala Gln Ala Lys Met Glu Lys Ala Ala Asn Ala Arg Asn His Asp
            255                 260                 265
```

-continued

| | | |
|---|---|---|
| gac aga gaa agc cag gac atc tat gac cac tac cta act cag gct gaa<br>Asp Arg Glu Ser Gln Asp Ile Tyr Asp His Tyr Leu Thr Gln Ala Glu<br>270 275 280 | 860 |
| atc cag ggc aat atc aac cat gtc aac gtc cat ggg gct cta gaa gtt<br>Ile Gln Gly Asn Ile Asn His Val Asn Val His Gly Ala Leu Glu Val<br>285 290 295 | 908 |
| gtt gat gat gcc ctg gaa aga cag agc cct gaa gcc ttg ctc aag gcc<br>Val Asp Asp Ala Leu Glu Arg Gln Ser Pro Glu Ala Leu Leu Lys Ala<br>300 305 310 315 | 956 |
| ctt caa gac cct gcc ctg gcc ctg cga ggg gtg agg aga gac ttt gct<br>Leu Gln Asp Pro Ala Leu Ala Leu Arg Gly Val Arg Arg Asp Phe Ala<br>320 325 330 | 1004 |
| gac tgg tac ctg gag cag ctg aac tca gac aga gag cag aag gca cag<br>Asp Trp Tyr Leu Glu Gln Leu Asn Ser Asp Arg Glu Gln Lys Ala Gln<br>335 340 345 | 1052 |
| gag ctg ggc ctg gtg gag ctt ctg gaa aag gag gaa gtc cag gct ggt<br>Glu Leu Gly Leu Val Glu Leu Leu Glu Lys Glu Glu Val Gln Ala Gly<br>350 355 360 | 1100 |
| gtg gct gca gcc aac aca aag ggt gat cag gaa caa gcc atg ctc cac<br>Val Ala Ala Ala Asn Thr Lys Gly Asp Gln Glu Gln Ala Met Leu His<br>365 370 375 | 1148 |
| gct gtg cag cgg atc aac aaa gcc atc cgg agg gga gtg gcg gct gac<br>Ala Val Gln Arg Ile Asn Lys Ala Ile Arg Arg Gly Val Ala Ala Asp<br>380 385 390 395 | 1196 |
| act gtg aag gag ctg atg tgc cct gag gcc cag ctg cct cca gtg tac<br>Thr Val Lys Glu Leu Met Cys Pro Glu Ala Gln Leu Pro Pro Val Tyr<br>400 405 410 | 1244 |
| cct gtt gca tcg tct atg tac cag ctg gag ctg gca gtg ctc cag cag<br>Pro Val Ala Ser Ser Met Tyr Gln Leu Glu Leu Ala Val Leu Gln Gln<br>415 420 425 | 1292 |
| cag cag ggg gag ctt ggc cag gag gag ctc ttc gtg gct gtg gag atg<br>Gln Gln Gly Glu Leu Gly Gln Glu Glu Leu Phe Val Ala Val Glu Met<br>430 435 440 | 1340 |
| ctc tca gct gtg gtc ctg att aac cgg gcc ctg gag gcc cgg gat gcc<br>Leu Ser Ala Val Val Leu Ile Asn Arg Ala Leu Glu Ala Arg Asp Ala<br>445 450 455 | 1388 |
| agt ggc ttc tgg agc agc ctg gtg aac cct gcc aca ggc ctg gct gag<br>Ser Gly Phe Trp Ser Ser Leu Val Asn Pro Ala Thr Gly Leu Ala Glu<br>460 465 470 475 | 1436 |
| gtg gaa gga gaa aat gcc cag cgt tac ttc gat gcc ctg ctg aaa ttg<br>Val Glu Gly Glu Asn Ala Gln Arg Tyr Phe Asp Ala Leu Leu Lys Leu<br>480 485 490 | 1484 |
| cga cag gag cgt ggg atg ggt gag gac ttc ctg agc tgg aat gac ctg<br>Arg Gln Glu Arg Gly Met Gly Glu Asp Phe Leu Ser Trp Asn Asp Leu<br>495 500 505 | 1532 |
| cag gcc acc gtg agc cag gtc aat gca cag acc cag gaa gag act gac<br>Gln Ala Thr Val Ser Gln Val Asn Ala Gln Thr Gln Glu Glu Thr Asp<br>510 515 520 | 1580 |
| cgg gtc ctt gca gtc agc ctc atc aat gag gct ctg gac aaa ggc agc<br>Arg Val Leu Ala Val Ser Leu Ile Asn Glu Ala Leu Asp Lys Gly Ser<br>525 530 535 | 1628 |
| cct gag aag act ctg tct gcc cta ctg ctt cct gca gct ggc cta gat<br>Pro Glu Lys Thr Leu Ser Ala Leu Leu Leu Pro Ala Ala Gly Leu Asp<br>540 545 550 555 | 1676 |
| gat gtc agc ctc cct gtc gcc cct cgg tac cat ctc ctc ctt gtg gca<br>Asp Val Ser Leu Pro Val Ala Pro Arg Tyr His Leu Leu Leu Val Ala<br>560 565 570 | 1724 |
| gcc aaa agg cag aag gcc cag gtg aca ggg gat cct gga gct gtg ctg<br>Ala Lys Arg Gln Lys Ala Gln Val Thr Gly Asp Pro Gly Ala Val Leu | 1772 |

-continued

| | | | | | | | | | | | | | | | | |
|---|---|---|---|---|---|---|---|---|---|---|---|---|---|---|---|---|
| | | | 575 | | | | 580 | | | | | 585 | | | | |
| tgg | ctt | gag | gag | atc | cgc | cag | gga | gtg | gtc | aga | gcc | aac | cag | gac | act | 1820 |
| Trp | Leu | Glu | Glu | Ile | Arg | Gln | Gly | Val | Val | Arg | Ala | Asn | Gln | Asp | Thr | |
| | | 590 | | | | | 595 | | | | | 600 | | | | |
| aat | aca | gct | cag | aga | atg | gct | ctt | ggt | gtg | gct | gcc | atc | aat | caa | gcc | 1868 |
| Asn | Thr | Ala | Gln | Arg | Met | Ala | Leu | Gly | Val | Ala | Ala | Ile | Asn | Gln | Ala | |
| | | 605 | | | | | 610 | | | | | 615 | | | | |
| atc | aag | gag | ggc | aag | gca | gcc | cag | act | gag | cgg | gtg | ttg | agg | aac | ccc | 1916 |
| Ile | Lys | Glu | Gly | Lys | Ala | Ala | Gln | Thr | Glu | Arg | Val | Leu | Arg | Asn | Pro | |
| 620 | | | | | 625 | | | | | 630 | | | | | 635 | |
| gca | gtg | gcc | ctt | cga | ggg | gta | gtt | ccc | gac | tgt | gcc | aac | ggc | tac | cag | 1964 |
| Ala | Val | Ala | Leu | Arg | Gly | Val | Val | Pro | Asp | Cys | Ala | Asn | Gly | Tyr | Gln | |
| | | | | 640 | | | | | 645 | | | | | 650 | | |
| cga | gcc | ctg | gaa | agt | gcc | atg | gca | aag | aaa | cag | cgt | cca | gca | gac | aca | 2012 |
| Arg | Ala | Leu | Glu | Ser | Ala | Met | Ala | Lys | Lys | Gln | Arg | Pro | Ala | Asp | Thr | |
| | | | 655 | | | | | 660 | | | | | 665 | | | |
| gct | ttc | tgg | gtt | caa | cat | gac | atg | aag | gat | ggc | act | gcc | tac | tac | ttc | 2060 |
| Ala | Phe | Trp | Val | Gln | His | Asp | Met | Lys | Asp | Gly | Thr | Ala | Tyr | Tyr | Phe | |
| | | 670 | | | | | 675 | | | | | 680 | | | | |
| cat | ctg | cag | acc | ttc | cag | ggg | atc | tgg | gag | caa | cct | cct | ggc | tgc | ccc | 2108 |
| His | Leu | Gln | Thr | Phe | Gln | Gly | Ile | Trp | Glu | Gln | Pro | Pro | Gly | Cys | Pro | |
| 685 | | | | | 690 | | | | | 695 | | | | | | |
| ctc | aac | acc | tct | cac | ctg | acc | cgg | gag | gag | atc | cag | tca | gct | gtc | acc | 2156 |
| Leu | Asn | Thr | Ser | His | Leu | Thr | Arg | Glu | Glu | Ile | Gln | Ser | Ala | Val | Thr | |
| 700 | | | | 705 | | | | | 710 | | | | | 715 | | |
| aag | gtc | act | gct | gcc | tat | gac | cgc | caa | cag | ctc | tgg | aaa | gcc | aac | gtc | 2204 |
| Lys | Val | Thr | Ala | Ala | Tyr | Asp | Arg | Gln | Gln | Leu | Trp | Lys | Ala | Asn | Val | |
| | | | | 720 | | | | | 725 | | | | | 730 | | |
| ggc | ttt | gtt | atc | cag | ctc | cag | gcc | cgc | ctc | cgt | ggc | ttc | cta | gtt | cgg | 2252 |
| Gly | Phe | Val | Ile | Gln | Leu | Gln | Ala | Arg | Leu | Arg | Gly | Phe | Leu | Val | Arg | |
| | | | 735 | | | | | 740 | | | | | 745 | | | |
| cag | aag | ttt | gct | gag | cat | tcc | cac | ttt | ctg | agg | acc | tgg | ctc | cca | gca | 2300 |
| Gln | Lys | Phe | Ala | Glu | His | Ser | His | Phe | Leu | Arg | Thr | Trp | Leu | Pro | Ala | |
| | | 750 | | | | | 755 | | | | | 760 | | | | |
| gtc | atc | aag | atc | cag | gct | cat | tgg | cgg | ggt | tat | agg | cag | cgg | aag | att | 2348 |
| Val | Ile | Lys | Ile | Gln | Ala | His | Trp | Arg | Gly | Tyr | Arg | Gln | Arg | Lys | Ile | |
| 765 | | | | | 770 | | | | | 775 | | | | | | |
| tac | ctg | gag | tgg | ttg | cag | tat | ttt | aaa | gca | aac | ctg | gat | gcc | ata | atc | 2396 |
| Tyr | Leu | Glu | Trp | Leu | Gln | Tyr | Phe | Lys | Ala | Asn | Leu | Asp | Ala | Ile | Ile | |
| 780 | | | | 785 | | | | | 790 | | | | | 795 | | |
| aag | atc | cag | gcc | tgg | gcc | cgg | atg | tgg | gca | gct | cgg | agg | caa | tac | ctg | 2444 |
| Lys | Ile | Gln | Ala | Trp | Ala | Arg | Met | Trp | Ala | Ala | Arg | Arg | Gln | Tyr | Leu | |
| | | | | 800 | | | | | 805 | | | | | 810 | | |
| agg | cgt | ctg | cac | tac | ttc | cag | aag | aat | gtt | aac | tcc | att | gtg | aag | atc | 2492 |
| Arg | Arg | Leu | His | Tyr | Phe | Gln | Lys | Asn | Val | Asn | Ser | Ile | Val | Lys | Ile | |
| | | | 815 | | | | | 820 | | | | | 825 | | | |
| cag | gca | ttt | ttc | cga | gcc | agg | aaa | gcc | caa | gat | gac | tac | agg | ata | tta | 2540 |
| Gln | Ala | Phe | Phe | Arg | Ala | Arg | Lys | Ala | Gln | Asp | Asp | Tyr | Arg | Ile | Leu | |
| | | 830 | | | | | 835 | | | | | 840 | | | | |
| gtg | cat | gca | ccc | cac | cct | cct | ctc | agt | gtg | gta | cgc | aga | ttt | gcc | cat | 2588 |
| Val | His | Ala | Pro | His | Pro | Pro | Leu | Ser | Val | Val | Arg | Arg | Phe | Ala | His | |
| | | 845 | | | | | 850 | | | | | 855 | | | | |
| ctc | ttg | aat | caa | agc | cag | caa | gac | ttc | ttg | gct | gag | gca | gag | ctg | ctg | 2636 |
| Leu | Leu | Asn | Gln | Ser | Gln | Gln | Asp | Phe | Leu | Ala | Glu | Ala | Glu | Leu | Leu | |
| 860 | | | | | 865 | | | | | 870 | | | | | 875 | |
| aag | ctc | cag | gaa | gag | gta | gtt | agg | aag | atc | cga | tcc | aat | cag | cag | ctg | 2684 |
| Lys | Leu | Gln | Glu | Glu | Val | Val | Arg | Lys | Ile | Arg | Ser | Asn | Gln | Gln | Leu | |
| | | | | 880 | | | | | 885 | | | | | 890 | | |
| gag | cag | gac | ctc | aac | atc | atg | gac | atc | aag | att | ggc | ctg | ctg | gtg | aag | 2732 |

```
Glu Gln Asp Leu Asn Ile Met Asp Ile Lys Ile Gly Leu Leu Val Lys
            895                 900                 905 aac cgg atc act ctg cag gaa gtg gtc tcc cac tgc aag aag ctg acc     2780
Asn Arg Ile Thr Leu Gln Glu Val Val Ser His Cys Lys Lys Leu Thr
        910                 915                 920 aag agg aat aag gaa cag ctg tca gat atg atg gtt ctg gac aag cag     2828
Lys Arg Asn Lys Glu Gln Leu Ser Asp Met Met Val Leu Asp Lys Gln
925                 930                 935 aag ggt tta aag tcg ctg agc aaa gag aaa cgg cag aaa cta gaa gca     2876
Lys Gly Leu Lys Ser Leu Ser Lys Glu Lys Arg Gln Lys Leu Glu Ala
940                 945                 950                 955 tac caa cac ctc ttc tac ctg ctc cag act cag ccc atc tac ctg gcc     2924
Tyr Gln His Leu Phe Tyr Leu Leu Gln Thr Gln Pro Ile Tyr Leu Ala
            960                 965                 970 aag ctg atc ttt cag atg cca cag aac aaa acc acc aag ttc atg gag     2972
Lys Leu Ile Phe Gln Met Pro Gln Asn Lys Thr Thr Lys Phe Met Glu
        975                 980                 985 gca gtg att ttc agc ctg tac aac tat gcc tcc agc cgc cga gag gcc     3020
Ala Val Ile Phe Ser Leu Tyr Asn Tyr Ala Ser Ser Arg Arg Glu Ala
990                 995                 1000 tat ctc ctg ctc cag ctg ttc aag aca gca ctc cag gag gaa atc aag     3068
Tyr Leu Leu Leu Gln Leu Phe Lys Thr Ala Leu Gln Glu Glu Ile Lys
    1005                1010                1015 tca aag gtg gag cag ccc cag gac gtg gtg aca ggc aac cca aca gtg     3116
Ser Lys Val Glu Gln Pro Gln Asp Val Val Thr Gly Asn Pro Thr Val
1020                1025                1030                1035 gtg agg ctg gtg gtg aga ttc tac cgt aat ggg cgg gga cag agt gcc     3164
Val Arg Leu Val Val Arg Phe Tyr Arg Asn Gly Arg Gly Gln Ser Ala
            1040                1045                1050 ctg cag gag att ctg ggc aag gtt atc cag gat gtg cta gaa gac aaa     3212
Leu Gln Glu Ile Leu Gly Lys Val Ile Gln Asp Val Leu Glu Asp Lys
        1055                1060                1065 gtg ctc agc gtc cac aca gac cct gtc cac ctc tat aag aac tgg atc     3260
Val Leu Ser Val His Thr Asp Pro Val His Leu Tyr Lys Asn Trp Ile
    1070                1075                1080 aac cag act gag gcc cag aca ggg cag cgc agc cat ctc cca tat gat     3308
Asn Gln Thr Glu Ala Gln Thr Gly Gln Arg Ser His Leu Pro Tyr Asp
    1085                1090                1095 gtc acc ccg gag cag gcc ttg agc cac ccc gag gtc cag aga cga ctg     3356
Val Thr Pro Glu Gln Ala Leu Ser His Pro Glu Val Gln Arg Arg Leu
1100                1105                1110                1115 gac atc gcc cta cgc aac ctc ctc gcc atg act gat aag ttc ctt tta     3404
Asp Ile Ala Leu Arg Asn Leu Leu Ala Met Thr Asp Lys Phe Leu Leu
            1120                1125                1130 gcc atc acc tca tct gtg gac caa att ccg tat ggg atg cga tat gtg     3452
Ala Ile Thr Ser Ser Val Asp Gln Ile Pro Tyr Gly Met Arg Tyr Val
        1135                1140                1145 gcc aaa gtc ctg aag gca act ctg gca gag aaa ttc cct gac gcc aca     3500
Ala Lys Val Leu Lys Ala Thr Leu Ala Glu Lys Phe Pro Asp Ala Thr
    1150                1155                1160 gac agc gag gtc tat aag gtg gtc ggg aac ctc ctg tac tac cgc ttc     3548
Asp Ser Glu Val Tyr Lys Val Val Gly Asn Leu Leu Tyr Tyr Arg Phe
1165                1170                1175 ctg aac cca gct gtg gtg gct cct gac gcc ttc gac att gtg gcc atg     3596
Leu Asn Pro Ala Val Val Ala Pro Asp Ala Phe Asp Ile Val Ala Met
1180                1185                1190                1195 gca gct ggt gga gcc ctg gct gcc ccc agc gcc atg gcc ctg ggg gct     3644
Ala Ala Gly Gly Ala Leu Ala Ala Pro Gln Arg His Ala Leu Gly Ala
            1200                1205                1210
```

-continued

| | |
|---|---|
| gtg gct cag ctc cta cag cac gct gcg gct ggc aag gcc ttc tct ggg<br>Val Ala Gln Leu Leu Gln His Ala Ala Ala Gly Lys Ala Phe Ser Gly<br>     1215              1220              1225 | 3692 |
| cag agc cag cac cta cgg gtc ctg aat gac tat ctg gag gaa aca cac<br>Gln Ser Gln His Leu Arg Val Leu Asn Asp Tyr Leu Glu Glu Thr His<br>1230              1235              1240 | 3740 |
| ctc aag ttc agg aag ttc atc cat aga gcc tgc cag gtg cca gag cca<br>Leu Lys Phe Arg Lys Phe Ile His Arg Ala Cys Gln Val Pro Glu Pro<br>1245              1250              1255 | 3788 |
| gag gag cgt ttt gca gtg gac gag tac tca gac atg gtg gct gtg gcc<br>Glu Glu Arg Phe Ala Val Asp Glu Tyr Ser Asp Met Val Ala Val Ala<br>1260              1265              1270              1275 | 3836 |
| aaa ccc atg gtg tac atc acc gtg ggg gag ctg gtc aac acg cac agg<br>Lys Pro Met Val Tyr Ile Thr Val Gly Glu Leu Val Asn Thr His Arg<br>     1280              1285              1290 | 3884 |
| ctg ttg ctg gag cac cag gac tgc att gcc cct gat cac caa gac ccc<br>Leu Leu Leu Glu His Gln Asp Cys Ile Ala Pro Asp His Gln Asp Pro<br>1295              1300              1305 | 3932 |
| ctg cat gag ctc ctg gag gat ctt ggg gag ctg ccc acc atc cct gac<br>Leu His Glu Leu Leu Glu Asp Leu Gly Glu Leu Pro Thr Ile Pro Asp<br>1310              1315              1320 | 3980 |
| ctt att ggt gag agc atc gct gca gat ggg cac aca gac ctg agc aag<br>Leu Ile Gly Glu Ser Ile Ala Ala Asp Gly His Thr Asp Leu Ser Lys<br>     1325              1330              1335 | 4028 |
| cta gaa gtg tcc ctg acg ctg acc aac aag ttt gaa gga cta gag gca<br>Leu Glu Val Ser Leu Thr Leu Thr Asn Lys Phe Glu Gly Leu Glu Ala<br>1340              1345              1350              1355 | 4076 |
| gat gct gat gac tcc aac acc cgt agc ctg ctt ctg agc acc aag cag<br>Asp Ala Asp Asp Ser Asn Thr Arg Ser Leu Leu Leu Ser Thr Lys Gln<br>              1360              1365              1370 | 4124 |
| ctg ttg gcc gat atc ata cag ttc cat cct ggg gac acc ctc aag gag<br>Leu Leu Ala Asp Ile Ile Gln Phe His Pro Gly Asp Thr Leu Lys Glu<br>     1375              1380              1385 | 4172 |
| atc ctg tcc ctc tcg gct tcc aga gag caa gaa gca gcc cac aag cag<br>Ile Leu Ser Leu Ser Ala Ser Arg Glu Gln Glu Ala Ala His Lys Gln<br>1390              1395              1400 | 4220 |
| ctg atg agc cga cgc cag gcc tgt aca gcc cag aca ccg gag cca ctg<br>Leu Met Ser Arg Arg Gln Ala Cys Thr Ala Gln Thr Pro Glu Pro Leu<br>1405              1410              1415 | 4268 |
| cga cga cac cgc tca ctg aca gct cac tcc ctc ctg cca ctg gca gag<br>Arg Arg His Arg Ser Leu Thr Ala His Ser Leu Leu Pro Leu Ala Glu<br>1420              1425              1430              1435 | 4316 |
| aag cag cgg cgc gtc ctg cgg aac ctg cgc cga ctt gaa gcc ctg ggg<br>Lys Gln Arg Arg Val Leu Arg Asn Leu Arg Arg Leu Glu Ala Leu Gly<br>              1440              1445              1450 | 4364 |
| ttg gtc agc gcc aga aat ggc tac cag ggg cta gtg gac gag ctg gcc<br>Leu Val Ser Ala Arg Asn Gly Tyr Gln Gly Leu Val Asp Glu Leu Ala<br>     1455              1460              1465 | 4412 |
| aag gac atc cgc aac cag cac aga cac agg cac agg cgg aag gca gag<br>Lys Asp Ile Arg Asn Gln His Arg His Arg His Arg Arg Lys Ala Glu<br>1470              1475              1480 | 4460 |
| ctg gtg aag ctg cag gcc aca tta cag ggc ctg agc act aag acc acc<br>Leu Val Lys Leu Gln Ala Thr Leu Gln Gly Leu Ser Thr Lys Thr Thr<br>1485              1490              1495 | 4508 |
| ttc tat gag gag cag ggt gac tac tac agc cag tac atc cgg gcc tgc<br>Phe Tyr Glu Glu Gln Gly Asp Tyr Tyr Ser Gln Tyr Ile Arg Ala Cys<br>1500              1505              1510              1515 | 4556 |
| ctg gac cac ctg gcc ccc gac tcc aag agt tct ggg aag ggg aag aag<br>Leu Asp His Leu Ala Pro Asp Ser Lys Ser Ser Gly Lys Gly Lys Lys<br>              1520              1525              1530 | 4604 |

-continued

```
cag cct tct ctt cat tac act gct gct cag ctc ctg gaa aag ggt gtc     4652
Gln Pro Ser Leu His Tyr Thr Ala Ala Gln Leu Leu Glu Lys Gly Val
        1535                1540                1545 ttg gtg gaa att gaa gat ctt ccc gcc tct cac ttc aga aac gtc atc     4700
Leu Val Glu Ile Glu Asp Leu Pro Ala Ser His Phe Arg Asn Val Ile
    1550                1555                1560 ttt gac atc acg ccg gga gat gag gca gga aag ttt gaa gta aat gcc     4748
Phe Asp Ile Thr Pro Gly Asp Glu Ala Gly Lys Phe Glu Val Asn Ala
1565                1570                1575 aag ttc ctg ggt gtg gac atg gag cga ttt cag ctt cac tat cag gat     4796
Lys Phe Leu Gly Val Asp Met Glu Arg Phe Gln Leu His Tyr Gln Asp
1580                1585                1590                1595 ctc ctg cag ctc cag tat gag ggt gtg gct gtc atg aaa ctc ttc aac     4844
Leu Leu Gln Leu Gln Tyr Glu Gly Val Ala Val Met Lys Leu Phe Asn
            1600                1605                1610 aag gcc aaa gtc aat gtc aac ctt ctc atc ttc ctc ctc aac aag aag     4892
Lys Ala Lys Val Asn Val Asn Leu Leu Ile Phe Leu Leu Asn Lys Lys
        1615                1620                1625 ttt ttg cgg aag           tgacag aggcaaaggg tgctacccaa gcccctctta   4940
Phe Leu Arg Lys
    1630 cctctctgga tgctttcttt aacactaact caccactgtg cttccctgca gacacccaga   5000 gctcaggact gggcaaggcc cagggattct caccccttcc ccagctggga ggagcttgcc   5060 tgcctggcca cagacagtgt atcttctaat tggctaaagt gggccttgcc cagagtccag   5120 ctgtgtggct tttatcatgc atgacaaacc cctggctttc ctgccagatg gattctcatc   5180 ccttacagct gactcttcca ggcaatttcc atagatctgc agtcctgcct ctgccacagt   5240 ctctctgttg tccccacatc tacccaactt cctgtactgt tgcccttctg atgttaataa   5300 aagcagctgt tactccc                                                  5317
```

<210> SEQ ID NO 4
<211> LENGTH: 1631
<212> TYPE: PRT
<213> ORGANISM: Homo sapiens

<400> SEQUENCE: 4

```
Met Glu Arg Arg Ala Ala Gly Pro Gly Trp Ala Ala Tyr Glu Arg Leu
 1               5                  10                  15

Thr Ala Glu Glu Met Asp Glu Gln Arg Arg Gln Asn Val Ala Tyr Gln
            20                  25                  30

Tyr Leu Cys Arg Leu Glu Glu Ala Lys Arg Trp Met Glu Ala Cys Leu
        35                  40                  45

Lys Glu Glu Leu Pro Ser Pro Val Glu Leu Glu Ser Leu Arg Asn
    50                  55                  60

Gly Val Leu Leu Ala Lys Leu Gly His Cys Phe Ala Pro Ser Val Val
65                  70                  75                  80

Pro Leu Lys Lys Ile Tyr Asp Val Glu Gln Leu Arg Tyr Gln Ala Thr
                85                  90                  95

Gly Leu His Phe Arg His Thr Asp Asn Ile Asn Phe Trp Leu Ser Ala
            100                 105                 110

Ile Ala His Ile Gly Leu Pro Ser Thr Phe Phe Pro Glu Thr Thr Asp
        115                 120                 125

Ile Tyr Asp Lys Lys Asn Met Pro Arg Val Val Tyr Cys Ile His Ala
    130                 135                 140

Leu Ser Leu Phe Leu Phe Arg Leu Gly Leu Ala Pro Gln Ile His Asp
```

```
            145                 150                 155                 160
Leu Tyr Gly Lys Val Lys Phe Thr Ala Glu Glu Leu Ser Asn Met Ala
                165                 170                 175
Ser Glu Leu Ala Lys Tyr Gly Leu Gln Leu Pro Ala Phe Ser Lys Ile
            180                 185                 190
Gly Gly Ile Leu Ala Asn Glu Leu Ser Val Asp Glu Ala Ala Val His
        195                 200                 205
Ala Ala Val Leu Ala Ile Asn Glu Ala Val Glu Arg Gly Val Val Glu
    210                 215                 220
Asp Thr Leu Ala Ala Leu Gln Asn Pro Ser Ala Leu Leu Glu Asn Leu
225                 230                 235                 240
Arg Glu Pro Leu Ala Ala Val Tyr Gln Glu Met Leu Ala Gln Ala Lys
                245                 250                 255
Met Glu Lys Ala Ala Asn Ala Arg Asn His Asp Asp Arg Glu Ser Gln
            260                 265                 270
Asp Ile Tyr Asp His Tyr Leu Thr Gln Ala Glu Ile Gln Gly Asn Ile
        275                 280                 285
Asn His Val Asn Val His Gly Ala Leu Glu Val Val Asp Asp Ala Leu
    290                 295                 300
Glu Arg Gln Ser Pro Glu Ala Leu Leu Lys Ala Leu Gln Asp Pro Ala
305                 310                 315                 320
Leu Ala Leu Arg Gly Val Arg Arg Asp Phe Ala Asp Trp Tyr Leu Glu
                325                 330                 335
Gln Leu Asn Ser Asp Arg Glu Gln Lys Ala Gln Glu Leu Gly Leu Val
            340                 345                 350
Glu Leu Leu Glu Lys Glu Glu Val Gln Ala Gly Val Ala Ala Ala Asn
        355                 360                 365
Thr Lys Gly Asp Gln Glu Gln Ala Met Leu His Ala Val Gln Arg Ile
    370                 375                 380
Asn Lys Ala Ile Arg Arg Gly Val Ala Ala Asp Thr Val Lys Glu Leu
385                 390                 395                 400
Met Cys Pro Glu Ala Gln Leu Pro Pro Val Tyr Pro Val Ala Ser Ser
                405                 410                 415
Met Tyr Gln Leu Glu Leu Ala Val Leu Gln Gln Gln Gly Glu Leu
            420                 425                 430
Gly Gln Glu Glu Leu Phe Val Ala Val Glu Met Leu Ser Ala Val Val
        435                 440                 445
Leu Ile Asn Arg Ala Leu Glu Ala Arg Asp Ala Ser Gly Phe Trp Ser
    450                 455                 460
Ser Leu Val Asn Pro Ala Thr Gly Leu Ala Glu Val Glu Gly Glu Asn
465                 470                 475                 480
Ala Gln Arg Tyr Phe Asp Ala Leu Leu Lys Leu Arg Gln Glu Arg Gly
                485                 490                 495
Met Gly Glu Asp Phe Leu Ser Trp Asn Asp Leu Gln Ala Thr Val Ser
            500                 505                 510
Gln Val Asn Ala Gln Thr Gln Glu Thr Asp Arg Val Leu Ala Val
        515                 520                 525
Ser Leu Ile Asn Glu Ala Leu Asp Lys Gly Ser Pro Glu Lys Thr Leu
    530                 535                 540
Ser Ala Leu Leu Leu Pro Ala Ala Gly Leu Asp Asp Val Ser Leu Pro
545                 550                 555                 560
Val Ala Pro Arg Tyr His Leu Leu Leu Val Ala Ala Lys Arg Gln Lys
                565                 570                 575
```

-continued

```
Ala Gln Val Thr Gly Asp Pro Gly Ala Val Leu Trp Leu Glu Glu Ile
            580                 585                 590
Arg Gln Gly Val Val Arg Ala Asn Gln Asp Thr Asn Thr Ala Gln Arg
        595                 600                 605
Met Ala Leu Gly Val Ala Ala Ile Asn Gln Ala Ile Lys Glu Gly Lys
610                 615                 620
Ala Ala Gln Thr Glu Arg Val Leu Arg Asn Pro Ala Val Ala Leu Arg
625                 630                 635                 640
Gly Val Val Pro Asp Cys Ala Asn Gly Tyr Gln Arg Ala Leu Glu Ser
                645                 650                 655
Ala Met Ala Lys Lys Gln Arg Pro Ala Asp Thr Ala Phe Trp Val Gln
            660                 665                 670
His Asp Met Lys Asp Gly Thr Ala Tyr Tyr Phe His Leu Gln Thr Phe
        675                 680                 685
Gln Gly Ile Trp Glu Gln Pro Pro Gly Cys Pro Leu Asn Thr Ser His
    690                 695                 700
Leu Thr Arg Glu Glu Ile Gln Ser Ala Val Thr Lys Val Thr Ala Ala
705                 710                 715                 720
Tyr Asp Arg Gln Gln Leu Trp Lys Ala Asn Val Gly Phe Val Ile Gln
                725                 730                 735
Leu Gln Ala Arg Leu Arg Gly Phe Leu Val Arg Gln Lys Phe Ala Glu
            740                 745                 750
His Ser His Phe Leu Arg Thr Trp Leu Pro Ala Val Ile Lys Ile Gln
        755                 760                 765
Ala His Trp Arg Gly Tyr Arg Gln Arg Lys Ile Tyr Leu Glu Trp Leu
    770                 775                 780
Gln Tyr Phe Lys Ala Asn Leu Asp Ala Ile Ile Lys Ile Gln Ala Trp
785                 790                 795                 800
Ala Arg Met Trp Ala Ala Arg Arg Gln Tyr Leu Arg Arg Leu His Tyr
                805                 810                 815
Phe Gln Lys Asn Val Asn Ser Ile Val Lys Ile Gln Ala Phe Phe Arg
            820                 825                 830
Ala Arg Lys Ala Gln Asp Asp Tyr Arg Ile Leu Val His Ala Pro His
        835                 840                 845
Pro Pro Leu Ser Val Val Arg Arg Phe Ala His Leu Leu Asn Gln Ser
    850                 855                 860
Gln Gln Asp Phe Leu Ala Glu Ala Glu Leu Leu Lys Leu Gln Glu Glu
865                 870                 875                 880
Val Val Arg Lys Ile Arg Ser Asn Gln Gln Leu Glu Gln Asp Leu Asn
                885                 890                 895
Ile Met Asp Ile Lys Ile Gly Leu Leu Val Lys Asn Arg Ile Thr Leu
            900                 905                 910
Gln Glu Val Val Ser His Cys Lys Lys Leu Thr Lys Arg Asn Lys Glu
        915                 920                 925
Gln Leu Ser Asp Met Met Val Leu Asp Lys Gln Lys Gly Leu Lys Ser
    930                 935                 940
Leu Ser Lys Glu Lys Arg Gln Lys Leu Glu Ala Tyr Gln His Leu Phe
945                 950                 955                 960
Tyr Leu Leu Gln Thr Gln Pro Ile Tyr Leu Ala Lys Leu Ile Phe Gln
                965                 970                 975
Met Pro Gln Asn Lys Thr Thr Lys Phe Met Glu Ala Val Ile Phe Ser
            980                 985                 990
```

```
Leu Tyr Asn Tyr Ala Ser Ser Arg Arg Glu Ala Tyr Leu Leu Leu Gln
        995                 1000                1005

Leu Phe Lys Thr Ala Leu Gln Glu Glu Ile Lys Ser Lys Val Glu Gln
   1010                1015                1020

Pro Gln Asp Val Val Thr Gly Asn Pro Thr Val Val Arg Leu Val Val
1025                1030                1035                1040

Arg Phe Tyr Arg Asn Gly Arg Gly Gln Ser Ala Leu Gln Glu Ile Leu
           1045                1050                1055

Gly Lys Val Ile Gln Asp Val Leu Glu Asp Lys Val Leu Ser Val His
       1060                1065                1070

Thr Asp Pro Val His Leu Tyr Lys Asn Trp Ile Asn Gln Thr Glu Ala
   1075                1080                1085

Gln Thr Gly Gln Arg Ser His Leu Pro Tyr Asp Val Thr Pro Glu Gln
   1090                1095                1100

Ala Leu Ser His Pro Glu Val Gln Arg Arg Leu Asp Ile Ala Leu Arg
1105                1110                1115                1120

Asn Leu Leu Ala Met Thr Asp Lys Phe Leu Leu Ala Ile Thr Ser Ser
           1125                1130                1135

Val Asp Gln Ile Pro Tyr Gly Met Arg Tyr Val Ala Lys Val Leu Lys
       1140                1145                1150

Ala Thr Leu Ala Glu Lys Phe Pro Asp Ala Thr Asp Ser Glu Val Tyr
   1155                1160                1165

Lys Val Val Gly Asn Leu Leu Tyr Tyr Arg Phe Leu Asn Pro Ala Val
       1170                1175                1180

Val Ala Pro Asp Ala Phe Asp Ile Val Ala Met Ala Ala Gly Gly Ala
1185                1190                1195                1200

Leu Ala Ala Pro Gln Arg His Ala Leu Gly Ala Val Ala Gln Leu Leu
           1205                1210                1215

Gln His Ala Ala Ala Gly Lys Ala Phe Ser Gly Gln Ser Gln His Leu
       1220                1225                1230

Arg Val Leu Asn Asp Tyr Leu Glu Glu Thr His Leu Lys Phe Arg Lys
   1235                1240                1245

Phe Ile His Arg Ala Cys Gln Val Pro Glu Pro Glu Glu Arg Phe Ala
   1250                1255                1260

Val Asp Glu Tyr Ser Asp Met Val Ala Val Ala Lys Pro Met Val Tyr
1265                1270                1275                1280

Ile Thr Val Gly Glu Leu Val Asn Thr His Arg Leu Leu Leu Glu His
           1285                1290                1295

Gln Asp Cys Ile Ala Pro Asp His Gln Asp Pro Leu His Glu Leu Leu
       1300                1305                1310

Glu Asp Leu Gly Glu Leu Pro Thr Ile Pro Asp Leu Ile Gly Glu Ser
   1315                1320                1325

Ile Ala Ala Asp Gly His Thr Asp Leu Ser Lys Leu Glu Val Ser Leu
   1330                1335                1340

Thr Leu Thr Asn Lys Phe Glu Gly Leu Glu Ala Asp Ala Asp Asp Ser
1345                1350                1355                1360

Asn Thr Arg Ser Leu Leu Leu Ser Thr Lys Gln Leu Leu Ala Asp Ile
           1365                1370                1375

Ile Gln Phe His Pro Gly Asp Thr Leu Lys Glu Ile Leu Ser Leu Ser
           1380                1385                1390

Ala Ser Arg Glu Gln Glu Ala Ala His Lys Gln Leu Met Ser Arg Arg
       1395                1400                1405

Gln Ala Cys Thr Ala Gln Thr Pro Glu Pro Leu Arg Arg His Arg Ser
```

```
                1410               1415               1420
Leu Thr Ala His Ser Leu Leu Pro Leu Ala Glu Lys Gln Arg Arg Val
1425               1430               1435               1440

Leu Arg Asn Leu Arg Arg Leu Glu Ala Leu Gly Leu Val Ser Ala Arg
                1445               1450               1455

Asn Gly Tyr Gln Gly Leu Val Asp Glu Leu Ala Lys Asp Ile Arg Asn
                1460               1465               1470

Gln His Arg His Arg His Arg Arg Lys Ala Glu Leu Val Lys Leu Gln
       1475               1480               1485

Ala Thr Leu Gln Gly Leu Ser Thr Lys Thr Thr Phe Tyr Glu Glu Gln
       1490               1495               1500

Gly Asp Tyr Tyr Ser Gln Tyr Ile Arg Ala Cys Leu Asp His Leu Ala
1505               1510               1515               1520

Pro Asp Ser Lys Ser Ser Gly Lys Gly Lys Lys Gln Pro Ser Leu His
                1525               1530               1535

Tyr Thr Ala Ala Gln Leu Leu Glu Lys Gly Val Leu Val Glu Ile Glu
            1540               1545               1550

Asp Leu Pro Ala Ser His Phe Arg Asn Val Ile Phe Asp Ile Thr Pro
       1555               1560               1565

Gly Asp Glu Ala Gly Lys Phe Glu Val Asn Ala Lys Phe Leu Gly Val
            1570               1575               1580

Asp Met Glu Arg Phe Gln Leu His Tyr Gln Asp Leu Leu Gln Leu Gln
1585               1590               1595               1600

Tyr Glu Gly Val Ala Val Met Lys Leu Phe Asn Lys Ala Lys Val Asn
                1605               1610               1615

Val Asn Leu Leu Ile Phe Leu Leu Asn Lys Lys Phe Leu Arg Lys
            1620               1625               1630

<210> SEQ ID NO 5
<211> LENGTH: 3608
<212> TYPE: DNA
<213> ORGANISM: Homo sapiens
<220> FEATURE:
<221> NAME/KEY: CDS
<222> LOCATION: (424)..(1908)
<223> OTHER INFORMATION: Clone LBFL110

<400> SEQUENCE: 5
ggcggcgaga gcagctgcag ctcgcatctc aggcagtacc tagaggagct gccggtgcct      60
cctcagaaca tctcctgatc gctacccagg accaggcacc aaggacaggg agtcccaggc     120
gcacaccccc cattctgggt cccccaggcc cagaccccca ctctgccaca ggttgcatct     180
tgacctggtc ctcctgcaga gtggcccct gtggtcctgc tctgagactc gtccctgggc      240
gcccctgcag cccctttcta tgactccatc tggatttggc tggctgtggg gacgcggtcc     300
gaggggcggc ctggctctca gcgtggtggc agccagctct ctggccacca tgcaaatgc      360 tgagatctga ggggacaagg ctctacagcc tcagccaggg gcactcagct gttgcagggt     420 gtg       atg gag aac aaa gct atg tac cta cac acc gtc agc gac tgt     465
          Met Glu Asn Lys Ala Met Tyr Leu His Thr Val Ser Asp Cys
           1               5                  10 gac acc agc tcc atc tgt gag gat tcc ttt gat ggc agg agc ctg tcc      513
Asp Thr Ser Ser Ile Cys Glu Asp Ser Phe Asp Gly Arg Ser Leu Ser
 15                  20                  25                  30 aag ctg aac ctg tgt gag gat ggt cca tgt cac aaa cgg cgg gca agc      561
Lys Leu Asn Leu Cys Glu Asp Gly Pro Cys His Lys Arg Arg Ala Ser
                 35                  40                  45
```

-continued

| | | |
|---|---|---|
| atc tgc tgt acc cag ctg ggg tcc ctg tcg gcc ctg aag cat gct gtc<br>Ile Cys Cys Thr Gln Leu Gly Ser Leu Ser Ala Leu Lys His Ala Val<br>　　　　　　　　50　　　　　　　　　　55　　　　　　　　　　60 | | 609 |
| ctg ggg ctc tac ctg ctg gtc ttc ctg att ctt gtg ggc atc ttc atc<br>Leu Gly Leu Tyr Leu Leu Val Phe Leu Ile Leu Val Gly Ile Phe Ile<br>　　　65　　　　　　　　　　70　　　　　　　　　　75 | | 657 |
| tta gca gtg tcc agg ccg cgc agc tcc cct gac gac ctg aag gcc ctg<br>Leu Ala Val Ser Arg Pro Arg Ser Ser Pro Asp Asp Leu Lys Ala Leu<br>80　　　　　　　　　　85　　　　　　　　　　90 | | 705 |
| act cgc aat gtg aac cgg ctg aat gag agc ttc cgg gac ttg cag ctg<br>Thr Arg Asn Val Asn Arg Leu Asn Glu Ser Phe Arg Asp Leu Gln Leu<br>95　　　　　　　　　　100　　　　　　　　　　105　　　　　　　　　　110 | | 753 |
| cgg ctg ctg cag gct ccg ctg caa gcg gac ctg acg gag cag gtg tgg<br>Arg Leu Leu Gln Ala Pro Leu Gln Ala Asp Leu Thr Glu Gln Val Trp<br>　　　　　　　　　115　　　　　　　　　　120　　　　　　　　　　125 | | 801 |
| aag gtg cag gac gcg ctg cag aac cag tca gac tcg ttg ctg gcg ctg<br>Lys Val Gln Asp Ala Leu Gln Asn Gln Ser Asp Ser Leu Leu Ala Leu<br>　　　　　　　　　130　　　　　　　　　　135　　　　　　　　　　140 | | 849 |
| gcg ggc gca gtg cag cgg ctg gag ggc gcg ctg tgg ggg ctg cag gcg<br>Ala Gly Ala Val Gln Arg Leu Glu Gly Ala Leu Trp Gly Leu Gln Ala<br>　　　　145　　　　　　　　　　150　　　　　　　　　　155 | | 897 |
| cag gcg gtg cag acc gag cag gcg gtg gcc ctg ctg cgg gac cgc acg<br>Gln Ala Val Gln Thr Glu Gln Ala Val Ala Leu Leu Arg Asp Arg Thr<br>160　　　　　　　　　　165　　　　　　　　　　170 | | 945 |
| ggc cag cag agc gac acg gcg cag ctg gag ctc tac cag ctg cag gtg<br>Gly Gln Gln Ser Asp Thr Ala Gln Leu Glu Leu Tyr Gln Leu Gln Val<br>175　　　　　　　　　　180　　　　　　　　　　185　　　　　　　　　　190 | | 993 |
| gag agc aac agt agc cag ctg ctg ctg agg cgc cac gcg ggc ctg ctg<br>Glu Ser Asn Ser Ser Gln Leu Leu Leu Arg Arg His Ala Gly Leu Leu<br>　　　　　　　　　195　　　　　　　　　　200　　　　　　　　　　205 | | 1041 |
| gac ggg ctg gcg cgc agg gtg ggc atc ctg ggc gag gag ctg gcc gac<br>Asp Gly Leu Ala Arg Arg Val Gly Ile Leu Gly Glu Glu Leu Ala Asp<br>　　　　　210　　　　　　　　　　215　　　　　　　　　　220 | | 1089 |
| gtg ggc ggc gtg ctg cgc ggc ctc aac cac agc ctg tcc tac gac gtg<br>Val Gly Gly Val Leu Arg Gly Leu Asn His Ser Leu Ser Tyr Asp Val<br>　　　　　225　　　　　　　　　　230　　　　　　　　　　235 | | 1137 |
| gcc ctc cac cgc acg cgg ctg cag gac ctg cgg gtg ctg gtg agc aac<br>Ala Leu His Arg Thr Arg Leu Gln Asp Leu Arg Val Leu Val Ser Asn<br>　240　　　　　　　　　　245　　　　　　　　　　250 | | 1185 |
| gcc agc gag gac acg cgc cgc ctg cgc ctg gcg cac gta ggc atg gag<br>Ala Ser Glu Asp Thr Arg Arg Leu Arg Leu Ala His Val Gly Met Glu<br>255　　　　　　　　　　260　　　　　　　　　　265　　　　　　　　　　270 | | 1233 |
| ctg cag ctg aag cag gag ctg gcc atg ctc aac gcg gtc acc gag gac<br>Leu Gln Leu Lys Gln Glu Leu Ala Met Leu Asn Ala Val Thr Glu Asp<br>　　　　　　　　　275　　　　　　　　　　280　　　　　　　　　　285 | | 1281 |
| ctg cgc ctc aag gac tgg gag cac tcc atc gca ctg cgg aac atc tcc<br>Leu Arg Leu Lys Asp Trp Glu His Ser Ile Ala Leu Arg Asn Ile Ser<br>　　　　　290　　　　　　　　　　295　　　　　　　　　　300 | | 1329 |
| ctc gcg aaa ggg cca ccg gga ccc aaa ggt gat cag ggg cat gaa gga<br>Leu Ala Lys Gly Pro Pro Gly Pro Lys Gly Asp Gln Gly His Glu Gly<br>　　　　　　　305　　　　　　　　　　310　　　　　　　　　　315 | | 1377 |
| aag gaa ggc agg cct ggc atc cct gga ttg cct gga ctt cga ggt ctg<br>Lys Glu Gly Arg Pro Gly Ile Pro Gly Leu Pro Gly Leu Arg Gly Leu<br>320　　　　　　　　　　325　　　　　　　　　　330 | | 1425 |
| ccc ggg gag aga ggt acc cca gga ttg ccc ggg ccc aag ggc gat gat<br>Pro Gly Glu Arg Gly Thr Pro Gly Leu Pro Gly Pro Lys Gly Asp Asp<br>335　　　　　　　　　　340　　　　　　　　　　345　　　　　　　　　　350 | | 1473 |
| ggg aag ctg ggg gcc aca gga cca atg ggc atg cgt ggg ttc aaa ggt<br>Gly Lys Leu Gly Ala Thr Gly Pro Met Gly Met Arg Gly Phe Lys Gly<br>　　　　　　　　　355　　　　　　　　　　360　　　　　　　　　　365 | | 1521 |

-continued

| | |
|---|---|
| gac cga ggc cca aaa gga gag aaa gga gag aaa gga gac aga gct ggg<br>Asp Arg Gly Pro Lys Gly Glu Lys Gly Glu Lys Gly Asp Arg Ala Gly<br>370                                   375                       380 | 1569 |
| gat gcc agt ggc gtg gag gcc ccg atg atg atc cgc ctg gtg aat ggc<br>Asp Ala Ser Gly Val Glu Ala Pro Met Met Ile Arg Leu Val Asn Gly<br>         385                          390 | 1617 |
| tca ggt ccg cac gag ggc cgc gtg gaa gtg tac cac gac cgg gtt tgg<br>Ser Gly Pro His Glu Gly Arg Val Glu Val Tyr His Asp Arg Arg Trp<br>400                                 405                      410 | 1665 |
| ggc acc gtg tgt gac gac ggc tgg gac aag aag gac gga gac gtg gtg<br>Gly Thr Val Cys Asp Asp Gly Trp Asp Lys Lys Asp Gly Asp Val Val<br>415                    420                     425                            430 | 1713 |
| tgc cgc atg ctc ggc ttc cgc ggt gtg gag gag gtg tac cgc aca gct<br>Cys Arg Met Leu Gly Phe Arg Gly Val Glu Glu Val Tyr Arg Thr Ala<br>                     435                     440                           445 | 1761 |
| cga ttc ggg caa ggc act ggg agg atc tgg atg gat gac gtt gcc tgc<br>Arg Phe Gly Gln Gly Thr Gly Arg Ile Trp Met Asp Asp Val Ala Cys<br>                  450                     455                        460 | 1809 |
| aag ggc aca gag gaa acc atc ttc cgc tgc agc ttc tcc aaa tgg ggg<br>Lys Gly Thr Glu Glu Thr Ile Phe Arg Cys Ser Phe Ser Lys Trp Gly<br>465                    470                     475 | 1857 |
| gtg aca aac tgt gga cat gcc gaa gat gcc agc gtg aca tgc aac aga<br>Val Thr Asn Cys Gly His Ala Glu Asp Ala Ser Val Thr Cys Asn Arg<br>         480                          485                       490 | 1905 |
| cac    tg aaagtgggca gagcccaagt tcggggtcct gcacagagca cccttcctgc<br>His<br>495 | 1960 |
| atccctgggg tggggcacag ctcggggcca ccctgaccat gcctcgacca cacccccgtcc | 2020 |
| agcattctca gtcctcacac ctgcatccca ggaccgtggg ggccggtcgt catttccctc | 2080 |
| ttgaacatgt gctccgaagt ataactctgg gacctactgc ccgtctctct cttccaccag | 2140 |
| gttcctgcat gaggagccct gatcaactgg atcaccactt tgcccagcct ctgaacacca | 2200 |
| tgcaccaggc ctcaatatcc cagttcccctt tggcctttta gttacaggtg aatgctgaga | 2260 |
| atgtgtcaga gacaagtgca gcagcagcga tggttggtag tatagatcat ttactcttca | 2320 |
| gacaattccc aaacctccat tagtccaaga gtttctacat cttcctcccc agcaagaggc | 2380 |
| aacgtcaagt gatgaatttc ccccctttac tctgcctctg ctccccattt gctagtttga | 2440 |
| ggaagtgaca tagaggagaa gccagctgta ggggcaagag ggaaatgcaa gtcacctgca | 2500 |
| ggaatccagc tagatttgga gaagggaatg aaactaacat tgaatgacta ccatggcacg | 2560 |
| ctaaatagta tcttgggtgc caaattcatg tatccactta gctgcattgg tccagggcat | 2620 |
| gtcagtctgg atacagcctt acctccaggt agcacttaac tggtccattc acctagactg | 2680 |
| caagtaagaa gacaaaatga ctgagaccgt gtgcccacct gaacttattg tctttacttg | 2740 |
| gcctgagcta aaagcttggg tgcaggacct gtgtaactag aaagttgcct acttcagaac | 2800 |
| ctccagggcg tgagtgcaag gtcaaacatg actggcttcc aggccgacca tcaatgtagg | 2860 |
| aggagagctg atgtggaggg tgacatgggg gctgcccatg ttaaacctga gtccagtgct | 2920 |
| ctggcattgg gcagtcacgg ttaaagccaa gtcatgtgtg tctcagctgt ttggaggtga | 2980 |
| tgattttgca tcttccaagc ctcttcaggt gtgaatctgt ggtcaggaaa acacaagtcc | 3040 |
| taatggaacc cttagggggg aaggaaatga agattcccta taacctctgg gggtggggag | 3100 |
| taggaataag gggcttgggc ctccataaat ctgcaatctg caccctcctc ctagagacag | 3160 |
| ggagatcgtg ttctgctttt tacatgagga gcagaactgg gccatacaca tgttcaagaa | 3220 |

-continued

```
ctaggggagc tacctggtag caagtgagtg cagacccacc tcaccttggg ggaatctcaa    3280
actcataggc ctcagataca cgatcacctg tcatatcagg tgagcactgg cctgcttggg    3340
gagagacctg gcccctcca ggtgtaggaa cagcaacact cctggctgac aactaagcca    3400
atatggcct aggtcattct tgcttccaat atgcttgcca ctccttaaat gtcctaatga     3460
tgagaaactc tctttctgac caattgctat gtttacataa cacgcatgta ctcatgcatc    3520
ccttgccaga gcccatatat gtatgcatat ataaacatag cacttttttac tacatagctc   3580
agcacattgc aaggtttgca tttaagtt                                        3608
```

<210> SEQ ID NO 6
<211> LENGTH: 495
<212> TYPE: PRT
<213> ORGANISM: Homo sapiens

<400> SEQUENCE: 6

Met Glu Asn Lys Ala Met Tyr Leu His Thr Val Ser Asp Cys Asp Thr
1               5                   10                  15

Ser Ser Ile Cys Glu Asp Ser Phe Asp Gly Arg Ser Leu Ser Lys Leu
            20                  25                  30

Asn Leu Cys Glu Asp Gly Pro Cys His Lys Arg Arg Ala Ser Ile Cys
        35                  40                  45

Cys Thr Gln Leu Gly Ser Leu Ser Ala Leu Lys His Ala Val Leu Gly
    50                  55                  60

Leu Tyr Leu Leu Val Phe Leu Ile Leu Val Gly Ile Phe Ile Leu Ala
65                  70                  75                  80

Val Ser Arg Pro Arg Ser Ser Pro Asp Asp Leu Lys Ala Leu Thr Arg
                85                  90                  95

Asn Val Asn Arg Leu Asn Glu Ser Phe Arg Asp Leu Gln Leu Arg Leu
            100                 105                 110

Leu Gln Ala Pro Leu Gln Ala Asp Leu Thr Glu Gln Val Trp Lys Val
        115                 120                 125

Gln Asp Ala Leu Gln Asn Gln Ser Asp Ser Leu Leu Ala Leu Ala Gly
    130                 135                 140

Ala Val Gln Arg Leu Glu Gly Ala Leu Trp Gly Leu Gln Ala Gln Ala
145                 150                 155                 160

Val Gln Thr Glu Gln Ala Val Ala Leu Leu Arg Asp Arg Thr Gly Gln
                165                 170                 175

Gln Ser Asp Thr Ala Gln Leu Glu Leu Tyr Gln Leu Gln Val Glu Ser
            180                 185                 190

Asn Ser Ser Gln Leu Leu Leu Arg Arg His Ala Gly Leu Leu Asp Gly
        195                 200                 205

Leu Ala Arg Arg Val Gly Ile Leu Gly Glu Glu Leu Ala Asp Val Gly
    210                 215                 220

Gly Val Leu Arg Gly Leu Asn His Ser Leu Ser Tyr Asp Val Ala Leu
225                 230                 235                 240

His Arg Thr Arg Leu Gln Asp Leu Arg Val Leu Val Ser Asn Ala Ser
                245                 250                 255

Glu Asp Thr Arg Arg Leu Arg Leu Ala His Val Gly Met Glu Leu Gln
            260                 265                 270

Leu Lys Gln Glu Leu Ala Met Leu Asn Ala Val Thr Glu Asp Leu Arg
        275                 280                 285

Leu Lys Asp Trp Glu His Ser Ile Ala Leu Arg Asn Ile Ser Leu Ala
    290                 295                 300

-continued

```
Lys Gly Pro Pro Gly Pro Lys Gly Asp Gln Gly His Glu Lys Glu
305                 310                 315                 320

Gly Arg Pro Gly Ile Pro Gly Leu Pro Gly Leu Arg Gly Leu Pro Gly
            325                 330                 335

Glu Arg Gly Thr Pro Gly Leu Pro Gly Pro Lys Gly Asp Asp Gly Lys
            340                 345                 350

Leu Gly Ala Thr Gly Pro Met Gly Met Arg Gly Phe Lys Gly Asp Arg
            355                 360                 365

Gly Pro Lys Gly Glu Lys Gly Glu Lys Gly Asp Arg Ala Gly Asp Ala
        370                 375                 380

Ser Gly Val Glu Ala Pro Met Met Ile Arg Leu Val Asn Gly Ser Gly
385                 390                 395                 400

Pro His Glu Gly Arg Val Glu Val Tyr His Asp Arg Arg Trp Gly Thr
                405                 410                 415

Val Cys Asp Asp Gly Trp Asp Lys Lys Asp Gly Asp Val Val Cys Arg
            420                 425                 430

Met Leu Gly Phe Arg Gly Val Glu Glu Val Tyr Arg Thr Ala Arg Phe
        435                 440                 445

Gly Gln Gly Thr Gly Arg Ile Trp Met Asp Asp Val Ala Cys Lys Gly
        450                 455                 460

Thr Glu Glu Thr Ile Phe Arg Cys Ser Phe Ser Lys Trp Gly Val Thr
465                 470                 475                 480

Asn Cys Gly His Ala Glu Asp Ala Ser Val Thr Cys Asn Arg His
                485                 490                 495

<210> SEQ ID NO 7
<211> LENGTH: 3162
<212> TYPE: DNA
<213> ORGANISM: Homo sapiens
<220> FEATURE:
<221> NAME/KEY: CDS
<222> LOCATION: (405)..(1835)
<223> OTHER INFORMATION: Clone LBFL123

<400> SEQUENCE: 7
tggccggggt gccccgcaaa gagagacaag ggagaaaaag acagcaggga aaacccgggg      60
gaggagaagg cgaaagagaa ggtggagctc agagaagggg gccggctccc cagctccatg     120
tggccgccgc cgctgcgggt ctgtgggggc agagggcggc ggctcccagg gcagcgcgta     180
gcgggaccga ttgcctaata ctccggcagg ggccggggcc gcagctggct cggataaata     240
gccgcccggc tggcccggag ctgcagggga gagcggcggc cgcgatcccc accacaccac     300
cagcccggcc gcacggggca ctgagccggg tgctgagcac cggaggcccc gccgaggccg     360
ggactcagga cctgcagaga aacgcctcct gattttgtct taca      atg gaa ctt     413
                                                 Met Glu Leu
                                                   1 aaa aag tcg cct gac ggt gga tgg ggc tgg gtg att gtg ttt gtc tcc        461
Lys Lys Ser Pro Asp Gly Gly Trp Gly Trp Val Ile Val Phe Val Ser
  5                  10                  15 ttc ctt act cag ttt ttg tgt tac gga tcc cca cta gct gtt gga gtc        509
Phe Leu Thr Gln Phe Leu Cys Tyr Gly Ser Pro Leu Ala Val Gly Val
 20                  25                  30                  35 ctg tac ata gaa tgg ctg gat gcc ttt ggt gaa gga aaa gga aaa aca        557
Leu Tyr Ile Glu Trp Leu Asp Ala Phe Gly Glu Gly Lys Gly Lys Thr
             40                  45                  50 gcc tgg gtt gga tcc ctg gca agt gga gtt ggc ttg ctt gca agt cct        605
Ala Trp Val Gly Ser Leu Ala Ser Gly Val Gly Leu Leu Ala Ser Pro
         55                  60                  65
```

-continued

| | | |
|---|---|---|
| gtc tgc agt ctc tgt gtc tca tct ttt gga gca aga cct gtc aca atc<br>Val Cys Ser Leu Cys Val Ser Ser Phe Gly Ala Arg Pro Val Thr Ile<br>       70                       75                    80 | 653 |
| ttc agt ggc ttc atg gtg gct gga ggc ctg atg ttg agc agt ttt gct<br>Phe Ser Gly Phe Met Val Ala Gly Gly Leu Met Leu Ser Ser Phe Ala<br>85                        90                       95 | 701 |
| ccc aat atc tac ttt ctg ttt ttt tcc tat ggc att gtt gta ggt tca<br>Pro Asn Ile Tyr Phe Leu Phe Phe Ser Tyr Gly Ile Val Val Gly Ser<br>100                      105                 110                115 | 749 |
| agc gtt ggc ctt ttc ata tat gct gct ctg cag agg atg ctg gtt gag<br>Ser Val Gly Leu Phe Ile Tyr Ala Ala Leu Gln Arg Met Leu Val Glu<br>                  120                 125                130 | 797 |
| ttc tat gga ctg gat gga tgc ttg ctg att gtg ggt gct tta gct tta<br>Phe Tyr Gly Leu Asp Gly Cys Leu Leu Ile Val Gly Ala Leu Ala Leu<br>                  135                 140                145 | 845 |
| aat ata tta gcc tgt ggc agt ctg atg aga ccc ctc caa tct tct gat<br>Asn Ile Leu Ala Cys Gly Ser Leu Met Arg Pro Leu Gln Ser Ser Asp<br>150                      155                 160 | 893 |
| tgt cct ttg cct aaa aaa ata gct cca gaa gat cta cca gat aaa tac<br>Cys Pro Leu Pro Lys Lys Ile Ala Pro Glu Asp Leu Pro Asp Lys Tyr<br>    165                    170                 175 | 941 |
| tcc att tac aat gaa aaa gga aag aat ctg gaa gaa aac ata aac att<br>Ser Ile Tyr Asn Glu Lys Gly Lys Asn Leu Glu Glu Asn Ile Asn Ile<br>180                      185                 190                195 | 989 |
| ctt gac aag agc tac agt agt gag gaa aaa tgc agg atc acg tta gcc<br>Leu Asp Lys Ser Tyr Ser Ser Glu Glu Lys Cys Arg Ile Thr Leu Ala<br>                  200                 205                210 | 1037 |
| aat ggt gac tgg aaa caa gac agc cta ctt cat aaa aac ccc aca gtg<br>Asn Gly Asp Trp Lys Gln Asp Ser Leu Leu His Lys Asn Pro Thr Val<br>215                      220                 225 | 1085 |
| aca cac aca aaa gag cct gaa acg tac aaa aag aaa gtt gca gaa cag<br>Thr His Thr Lys Glu Pro Glu Thr Tyr Lys Lys Lys Val Ala Glu Gln<br>                  230                 235                240 | 1133 |
| aca tat ttt tgc aaa cag ctt gcc aag agg aag tgg cag tta tat aaa<br>Thr Tyr Phe Cys Lys Gln Leu Ala Lys Arg Lys Trp Gln Leu Tyr Lys<br>245                      250                 255 | 1181 |
| aac tac tgt ggt gaa act gtg gct ctt ttt aaa aac aaa gta ttt tca<br>Asn Tyr Cys Gly Glu Thr Val Ala Leu Phe Lys Asn Lys Val Phe Ser<br>260                      265                 270                275 | 1229 |
| gcc ctt ttc att gct atc tta ctc ttt gac atc gga ggg ttt cca cct<br>Ala Leu Phe Ile Ala Ile Leu Leu Phe Asp Ile Gly Gly Phe Pro Pro<br>                  280                 285                290 | 1277 |
| tca tta ctt atg gaa gat gta gca aga agt tca aac gtg aaa gaa gaa<br>Ser Leu Leu Met Glu Asp Val Ala Arg Ser Ser Asn Val Lys Glu Glu<br>295                      300                 305 | 1325 |
| gag ttt att atg cca ctt att tcc att ata ggc att atg aca gca gtt<br>Glu Phe Ile Met Pro Leu Ile Ser Ile Ile Gly Ile Met Thr Ala Val<br>                  310                 315                320 | 1373 |
| ggt aaa ctg ctt tta ggg ata ctg gct gac ttc aag tgg att aat acc<br>Gly Lys Leu Leu Leu Gly Ile Leu Ala Asp Phe Lys Trp Ile Asn Thr<br>325                      330                 335 | 1421 |
| ttg tat ctt tat gtt gct acc tta atc atc atg ggc cta gcc ttg tgt<br>Leu Tyr Leu Tyr Val Ala Thr Leu Ile Ile Met Gly Leu Ala Leu Cys<br>340                      345                 350                355 | 1469 |
| gca att cca ttt gcc aaa agc tat gtc aca ttg gcg ttg ctt tct ggg<br>Ala Ile Pro Phe Ala Lys Ser Tyr Val Thr Leu Ala Leu Leu Ser Gly<br>                  360                 365                370 | 1517 |
| atc cta ggg ttt ctt act ggt aat tgg tcc atc ttt cca tat gtg acc<br>Ile Leu Gly Phe Leu Thr Gly Asn Trp Ser Ile Phe Pro Tyr Val Thr | 1565 |

-continued

```
                    375                 380                 385
acg aag act gtg gga att gaa aaa tta gcc cat gcc tat ggg ata tta      1613
Thr Lys Thr Val Gly Ile Glu Lys Leu Ala His Ala Tyr Gly Ile Leu
            390                 395                 400 atg ttc ttt gct gga ctt gga aat agc cta gga cca ccc atc gtt ggt      1661
Met Phe Phe Ala Gly Leu Gly Asn Ser Leu Gly Pro Pro Ile Val Gly
    405                 410                 415 tgg ttt tat gac tgg acc cag acc tat gat att gca ttt tat ttt agt      1709
Trp Phe Tyr Asp Trp Thr Gln Thr Tyr Asp Ile Ala Phe Tyr Phe Ser
420                 425                 430                 435 ggc ttc tgc gtc ctg ctg gga ggt ttt att ctg ctg ctg gca gcc ttg      1757
Gly Phe Cys Val Leu Leu Gly Gly Phe Ile Leu Leu Leu Ala Ala Leu
                440                 445                 450 ccc tct tgg gat aca tgc aac aag caa ctc ccc aag cca gct cca aca      1805
Pro Ser Trp Asp Thr Cys Asn Lys Gln Leu Pro Lys Pro Ala Pro Thr
            455                 460                 465 act ttc ttg tac aaa gtt gcc tct aat gtt      tagaa gaatattgga        1850
Thr Phe Leu Tyr Lys Val Ala Ser Asn Val
    470                 475 agacactatt tttgctattt tataccatat agcaacgata ttttaacaga tctcaagcaa    1910
attttctaga gtcaagacta ttttctcata gcaaaatttc acaatgactg actctgaatg   1970
aattattttt ttttttttat atatcctatt ttttatgtag tgtatgcgta gcctctatct   2030
cgtatttttt tctatttctc ctcccacac catcaatggg actattctgt tttgctgtta    2090
ttcactagtt cttaacattg taaaaagttt gaccagcctc agaaggcttt ctctgtgtaa   2150
agaagtataa tttctctgct gactccattt aatccactgc aaggcaccta gagagactgc   2210
tcctatttta aaagtgatgc aagcatcatg ataagatatg tgtgaagccc actaggaaat   2270
aaatcattct cttctctatg tttgacttgc tagtaaacag aagacttcaa gccagccagg   2330
aaattaaagt ggcgactaaa acagccttaa gaattgcagt ggagcaaatt ggtcattttt   2390
taaaaaaata tattttaacc tacagtcacc agttttcatt attctattta cctcactgaa   2450
gtactcgcat gttgtttggt acccactgag caactgtttc agttcctaag gtatttgctg   2510
agatgtgggt gaactccaaa tggagaagta gtcactgtag actttcttca tggttgacca   2570
ctccaacctt gctcactttt gcttcttggc catccactca gctgatgttt cctgggaagt   2630
gctaatttta cctgtttcca aattggaaac acatttctca atcattccgt tctggcaaat   2690
gggaaacatc catttgcttt gggcacagtg gggatgggct gcaagttctt gcatatcctc   2750
ccagtgaagc atttatttgc tactatcaga ttttaccact atcaaatata attcaagggc   2810
agaattaaac gtgagtgtgt gtgtgtgtgt gtgtgtgt gctatgcatg ctctaagtct     2870
gcatgggata tgggaatgga aagggcaat aagaaattaa tacccttatg cagttgcatt    2930
taaccttaag aaaaatgtcc ttgggataaa ctccaatgtt taatacattg attttttttc   2990
taaagaaatg ggttttaaac tttggtatgc atcagaattc cctatagatc ttttgaaaa    3050
tataggtacc tgggtatcac acatagaact tttaattctg ctggtgtagg ctgttgccca   3110
aacatctata attttactga gctcttcaag tgattctgat aacacagcct gg           3162
```

<210> SEQ ID NO 8
<211> LENGTH: 477
<212> TYPE: PRT
<213> ORGANISM: Homo sapiens

<400> SEQUENCE: 8

Met Glu Leu Lys Lys Ser Pro Asp Gly Gly Trp Gly Trp Val Ile Val

-continued

```
  1               5              10              15
Phe Val Ser Phe Leu Thr Gln Phe Leu Cys Tyr Gly Ser Pro Leu Ala
             20              25              30
Val Gly Val Leu Tyr Ile Glu Trp Leu Asp Ala Phe Gly Glu Gly Lys
             35              40              45
Gly Lys Thr Ala Trp Val Gly Ser Leu Ala Ser Gly Val Gly Leu Leu
             50              55              60
Ala Ser Pro Val Cys Ser Leu Cys Val Ser Ser Phe Gly Ala Arg Pro
 65              70              75              80
Val Thr Ile Phe Ser Gly Phe Met Val Ala Gly Gly Leu Met Leu Ser
             85              90              95
Ser Phe Ala Pro Asn Ile Tyr Phe Leu Phe Phe Ser Tyr Gly Ile Val
            100             105             110
Val Gly Ser Ser Val Gly Leu Phe Ile Tyr Ala Ala Leu Gln Arg Met
            115             120             125
Leu Val Glu Phe Tyr Gly Leu Asp Gly Cys Leu Leu Ile Val Gly Ala
            130             135             140
Leu Ala Leu Asn Ile Leu Ala Cys Gly Ser Leu Met Arg Pro Leu Gln
145             150             155             160
Ser Ser Asp Cys Pro Leu Pro Lys Lys Ile Ala Pro Glu Asp Leu Pro
            165             170             175
Asp Lys Tyr Ser Ile Tyr Asn Glu Lys Gly Lys Asn Leu Glu Glu Asn
            180             185             190
Ile Asn Ile Leu Asp Lys Ser Tyr Ser Glu Glu Lys Cys Arg Ile
            195             200             205
Thr Leu Ala Asn Gly Asp Trp Lys Gln Asp Ser Leu Leu His Lys Asn
            210             215             220
Pro Thr Val Thr His Thr Lys Glu Pro Glu Thr Tyr Lys Lys Val
225             230             235             240
Ala Glu Gln Thr Tyr Phe Cys Lys Gln Leu Ala Lys Arg Lys Trp Gln
            245             250             255
Leu Tyr Lys Asn Tyr Cys Gly Glu Thr Val Ala Leu Phe Lys Asn Lys
            260             265             270
Val Phe Ser Ala Leu Phe Ile Ala Ile Leu Leu Phe Asp Ile Gly Gly
            275             280             285
Phe Pro Pro Ser Leu Leu Met Glu Asp Val Ala Arg Ser Ser Asn Val
            290             295             300
Lys Glu Glu Glu Phe Ile Met Pro Leu Ile Ser Ile Ile Gly Ile Met
305             310             315             320
Thr Ala Val Gly Lys Leu Leu Leu Gly Ile Leu Ala Asp Phe Lys Trp
            325             330             335
Ile Asn Thr Leu Tyr Leu Tyr Val Ala Thr Leu Ile Ile Met Gly Leu
            340             345             350
Ala Leu Cys Ala Ile Pro Phe Ala Lys Ser Tyr Val Thr Leu Ala Leu
            355             360             365
Leu Ser Gly Ile Leu Gly Phe Leu Thr Gly Asn Trp Ser Ile Phe Pro
            370             375             380
Tyr Val Thr Thr Lys Thr Val Gly Ile Glu Lys Leu Ala His Ala Tyr
385             390             395             400
Gly Ile Leu Met Phe Phe Ala Gly Leu Gly Asn Ser Leu Gly Pro Pro
            405             410             415
Ile Val Gly Trp Phe Tyr Asp Thr Gln Thr Tyr Asp Ile Ala Phe
            420             425             430
```

-continued

```
Tyr Phe Ser Gly Phe Cys Val Leu Leu Gly Gly Phe Ile Leu Leu Leu
        435                 440                 445

Ala Ala Leu Pro Ser Trp Asp Thr Cys Asn Lys Gln Leu Pro Lys Pro
    450                 455                 460

Ala Pro Thr Thr Phe Leu Tyr Lys Val Ala Ser Asn Val
465                 470                 475

<210> SEQ ID NO 9
<211> LENGTH: 4891
<212> TYPE: DNA
<213> ORGANISM: Homo sapiens
<220> FEATURE:
<221> NAME/KEY: CDS
<222> LOCATION: (89)..(1150)
<223> OTHER INFORMATION: Clone LBFL131

<400> SEQUENCE: 9
acgcctggtt cccgggaaga ctcgccagca ccaggggggtg ggggagtgcg agctgaaagc        60
tgctggagag tgagcagccc tagcaggg atg gac atg atg ctg ttg gtg cag       112
                                Met Asp Met Met Leu Leu Val Gln
                                  1               5 ggt gct tgt tgc tcg aac cag tgg ctg gcg gcg gtg ctc ctc agc ctg       160
Gly Ala Cys Cys Ser Asn Gln Trp Leu Ala Ala Val Leu Leu Ser Leu
            10                  15                  20 tgc tgc ctg cta ccc tcc tgc ctc ccg gct gga cag agt gtg gac ttc       208
Cys Cys Leu Leu Pro Ser Cys Leu Pro Ala Gly Gln Ser Val Asp Phe
 25                  30                  35                  40 ccc tgg gcg gcc gtg gac aac atg atg gtc aga aaa ggg gac acg gcg       256
Pro Trp Ala Ala Val Asp Asn Met Met Val Arg Lys Gly Asp Thr Ala
                45                  50                  55 gtg ctt agg tgt tat ttg gaa gat gga gct tca aag ggt gcc tgg ctg       304
Val Leu Arg Cys Tyr Leu Glu Asp Gly Ala Ser Lys Gly Ala Trp Leu
            60                  65                  70 aac cgg tca agt att att ttt gcg gga ggt gat aag tgg tca gtg gat       352
Asn Arg Ser Ser Ile Ile Phe Ala Gly Gly Asp Lys Trp Ser Val Asp
        75                  80                  85 cct cga gtt tca att tca aca ttg aat aaa agg gac tac agc ctc cag       400
Pro Arg Val Ser Ile Ser Thr Leu Asn Lys Arg Asp Tyr Ser Leu Gln
     90                  95                 100 ata cag aat gta gat gtg aca gat gat ggc cca tac acg tgt tct gtt       448
Ile Gln Asn Val Asp Val Thr Asp Asp Gly Pro Tyr Thr Cys Ser Val
105                 110                 115                 120 cag act caa cat aca ccc aga aca atg cag gtg cat cta act gtg caa       496
Gln Thr Gln His Thr Pro Arg Thr Met Gln Val His Leu Thr Val Gln
                125                 130                 135 gtt cct cct aag ata tat gac atc tca aat gat atg acc gtc aat gaa       544
Val Pro Pro Lys Ile Tyr Asp Ile Ser Asn Asp Met Thr Val Asn Glu
            140                 145                 150 gga acc aac gtc act ctt act tgt ttg gcc act ggg aaa cca gag cct       592
Gly Thr Asn Val Thr Leu Thr Cys Leu Ala Thr Gly Lys Pro Glu Pro
        155                 160                 165 tcc att tct tgg cga cac atc tcc cca tca gcg aaa cca ttt gaa aat       640
Ser Ile Ser Trp Arg His Ile Ser Pro Ser Ala Lys Pro Phe Glu Asn
    170                 175                 180 gga caa tat ttg gac att tat gga att aca agg gac cag gct ggg gaa       688
Gly Gln Tyr Leu Asp Ile Tyr Gly Ile Thr Arg Asp Gln Ala Gly Glu
185                 190                 195                 200 tat gaa tgc agt gcg gaa aat gat gtg tca ttc cca gat gtg agg aaa       736
Tyr Glu Cys Ser Ala Glu Asn Asp Val Ser Phe Pro Asp Val Arg Lys
                205                 210                 215
```

|  |  |
|---|---:|
| gta aaa gtt gtt gtc aac ttt gct cct act att cag gaa att aaa tct<br>Val Lys Val Val Val Asn Phe Ala Pro Thr Ile Gln Glu Ile Lys Ser<br>220                          225                     230 | 784 |
| ggc acc gtg acc ccc gga cgc agt ggc ctg ata aga tgt gaa ggt gca<br>Gly Thr Val Thr Pro Gly Arg Ser Gly Leu Ile Arg Cys Glu Gly Ala<br>235                         240                   245 | 832 |
| ggt gtg ccg cct cca gcc ttt gaa tgg tac aaa gga gag aag aag ctc<br>Gly Val Pro Pro Pro Ala Phe Glu Trp Tyr Lys Gly Glu Lys Lys Leu<br>250                         255                   260 | 880 |
| ttc aat ggc caa caa gga att att att caa aat ttt agc aca aga tcc<br>Phe Asn Gly Gln Gln Gly Ile Ile Ile Gln Asn Phe Ser Thr Arg Ser<br>265                       270                   275                  280 | 928 |
| att ctc act gtt acc aac gtg aca cag gag cac ttc ggc aat tat act<br>Ile Leu Thr Val Thr Asn Val Thr Gln Glu His Phe Gly Asn Tyr Thr<br>285                         290                   295 | 976 |
| tgt gtg gct gcc aac aag cta ggc aca acc aat gcg agc ctg cct ctt<br>Cys Val Ala Ala Asn Lys Leu Gly Thr Thr Asn Ala Ser Leu Pro Leu<br>300                       305                   310 | 1024 |
| aac cct cca agt aca gcc cag tat gga att acc ggg agc gct gat gtt<br>Asn Pro Pro Ser Thr Ala Gln Tyr Gly Ile Thr Gly Ser Ala Asp Val<br>315                     320                   325 | 1072 |
| ctt ttc tcc tgc tgg tac ctt gtg ttg aca ctg tcc tct ttc acc agc<br>Leu Phe Ser Cys Trp Tyr Leu Val Leu Thr Leu Ser Ser Phe Thr Ser<br>330                       335                   340 | 1120 |
| ata ttc tac ctg aag aat gcc att cta caa       taaattcaaa gacccataaa<br>Ile Phe Tyr Leu Lys Asn Ala Ile Leu Gln<br>345                   350 | 1170 |
| aggcttttaa ggattctctg aaagtgctga tggctggatc caatctggta cagtttgtta | 1230 |
| aaagcagcgt gggatataat cagcagtgct acatggggga tgatcgcctt ctgtagaatt | 1290 |
| gctcattatg taaatacttt aattctactc tttttgatt agctacatta ccttgtgaag | 1350 |
| cagtacacat tgtcctttt ttaagacgtg aaagctctga aattacttt agaggatatt | 1410 |
| aattgtgatt tcatgtttgt aatctacaac ttttcaaaag cattcagtca tggtctgcta | 1470 |
| ggttgcaggc tgtagtttac aaaaacgaat attgcagtga atatgtgatt ctttaaggct | 1530 |
| gcaatacaag cattcagttc cctgtttcaa taagagtcaa tccacattta caaagatgca | 1590 |
| ttttttttctt ttttgataaa aaagcaaata atattgcctt cagattattt cttcaaaata | 1650 |
| taacacatat ctagattttt ctgctcgcat gatattcagg tttcaggaat gagccttgta | 1710 |
| atataactgg ctgtgcagct ctgcttctct ttcctgtaag ttcagcatgg gtgtgccttc | 1770 |
| atacaataat attttctct ttgtctccaa ctaatataaa atgttttgct aaatcttaca | 1830 |
| atttgaaagt aaaataaac cagagtgatc aagttaaacc atacactatc tctaagtaac | 1890 |
| gaaggagcta ttggactgta aaaatctctt cctgcactga caatggggtt tgagaatttt | 1950 |
| gccccacact aactcagttc ttgtgatgag agacaattta ataacagtat agtaaatata | 2010 |
| ccatatgatt tctttagttg tagctaaatg ttagatccac cgtgggaaat tattcccttt | 2070 |
| aaaatgacag cacagtccac tcaaaggatt gcctagcaat acagcatctt ttccttcac | 2130 |
| tagtccaagc caaaaatttt aagatgattt gtcagaaagg gcacaaagtc ctatcaccta | 2190 |
| atattcaag agttggtaag cgctcatcat taatttatt ttgtggcagc taagttagta | 2250 |
| tgacagaggc agtgctcctg tggacaggag cattttgcat attttccatc tgaaagtatc | 2310 |
| actcagttga tagtctggaa tgcatgttat atattttaaa acttccaaaa tatattataa | 2370 |
| caaacattct atatcggtat gtagcagacc aatctctaaa atagctaatt cttcaataaa | 2430 |

```
atctttctat atagccattt cagtgcaaac aagtaaaatc aaaaaagacc atcctttatt    2490
tttccttaca tgatatatgt aagatgcgat caaataaaga caaaacacca gtgatgagaa    2550
tatcttaaga taagtaatta tcaaattatt gtgaatgtta aattatttct actataaaga    2610
agcaaaacta cattttttgaa ggaaaatgct gttactctaa cattaattta caggaatagt    2670
ttgatggttt cactctttac taaagaaagg ccatcaccct gaaagccatt ttacaggttt    2730
gatgaagtta ccaatttcag tacacctaaa tttctacaaa tagtccccct ttacaagttg    2790
taacaacaaa gaccctataa taaaattaga tacaagaaat tttgcagtgg ttatacatat    2850
ttgagatatc tagtatgttg ccctagcagg gatggcttaa aaactgtgat ttttttttctt    2910 caagtaaaac ttagtcccaa agtacatcat aaatcaattt taactagaaa atgaatctt    2970 aaatgagggg acataagtat actctttcca caaaatggca ataataaggc ataaagctag    3030
taaatctact aactgtaata aatgtatgac attattttga ttgatacatt aaaaaagagt    3090
ttttagaaca aatatggcat ttaactttat tatttatttg cttttaagaa atattctttg    3150
tggaattgtt gaataaacta taaaatatta ttttgtattg cagctttaaa gtggcacact    3210
ccataataat ctacctacta gaaatagtgg tgctaccaca aaaaatgtta accatcagta    3270
ccattgtttg ggagaaagaa acaggtcaag aatgcatatt attcagtgac cgctttccta    3330
gagttaaaat acctcctctt tgtaaggttt gtaggtaaat tgaggtataa actatggatg    3390
aaccaaataa ttagttcaaa gtgttgtcat gattccaaat ttgtggagtc tggtgttttt    3450
accatagaat gtgacagaag tacagtcata gctcagtagc tatatgtatt tgcctttatg    3510
ttagaagaga cttttcttgag tgacattttt aaatagagga ggtattcact atgtttttct    3570
gtatcacagc agcattccta gtccttaggc cctcggacag agtgaaatca tgagtattta    3630
tgagttcaat attgtcaaat aaggctacag tatttgcttt tttgtgtgaa tgtattgcat    3690
ataatgttca agtagatgat tttacattta tggacatata aaacgtctga ttaccccatt    3750
ttatcagtcc tgactgtaca agattgttgc aatttcagaa tagcagtttt ataaattgat    3810
ttatctttta atctataaca atttgtgtta gctgttcatt tcaggattat attttctaca    3870
agttccactt gtgggactcc ttttgttgcc cctattttt tttaaagaag gaagaaagaa    3930
aaatgagtag cagtttaaaa atgagaatgg agagaaaaga aaaagaatga aaaggaaagg    3990
cagtaaagag ggaaaaaaaa ggaaggatgg aaggaatgaa ggaaggaagg gaggaagggg    4050
agaaggtagg aagaaagaaa ggatgagagg gaaggaagaa tcagagtatt agggtagtta    4110
acttacacat ttgcattctt agttatactg caagtggtgt aactatgttt ttcaatgatc    4170
gcatttgaaa cataagtcct attataccat taagttccta ttatgcagca attatataat    4230
aaaaagtact gcccaagtta tagtaatgtg ggtgtttttg agacactaaa agatttgaga    4290
gggagaattt caaacttaaa gccacttttg gggggtttat aacttaactg aaaaattaat    4350
gcttcatcat aacatttaag ctatatctag aaagtagact ggagaactga gaaaattacc    4410
caggtaattc agggaaaaaa aaaaaatata tatatatata aatacccccta catttgaagt    4470 cagaaaactc tgaaaaactg aattatcaaa gtcaatcatc tataatgatc aaatttactg    4530
aacaattgtt aatttatcca ttgtgcttag ctttgtgaca cagccaaaag ttacctattt    4590
aatcttttca ataaaaattg ttttttgaaa tccagaaatg atttaaaaag aggtcaggtt    4650
tttaactatt tattgaagta tgtggatgtc cagtatttca atagatatga atatgaataa    4710
atggtatgcc ttaagattct ttgaatatgt atttacttta aagactggaa aaagctcttc    4770
ctgtctttta gtaaacatcc atatttcata acctgatgta aaatatgttg tactgtttcc    4830
```

```
aatagggaa tataaactca gtttatcaat taaaaaaaaa aaaaaaaaaa aaaaaaaaaa        4890
a                                                                       4891
```

<210> SEQ ID NO 10
<211> LENGTH: 354
<212> TYPE: PRT
<213> ORGANISM: Homo sapiens

<400> SEQUENCE: 10

```
Met Asp Met Met Leu Leu Val Gln Gly Ala Cys Cys Ser Asn Gln Trp
 1               5                  10                  15

Leu Ala Ala Val Leu Leu Ser Leu Cys Cys Leu Leu Pro Ser Cys Leu
            20                  25                  30

Pro Ala Gly Gln Ser Val Asp Phe Pro Trp Ala Ala Val Asp Asn Met
        35                  40                  45

Met Val Arg Lys Gly Asp Thr Ala Val Leu Arg Cys Tyr Leu Glu Asp
    50                  55                  60

Gly Ala Ser Lys Gly Ala Trp Leu Asn Arg Ser Ser Ile Ile Phe Ala
65                  70                  75                  80

Gly Gly Asp Lys Trp Ser Val Asp Pro Arg Val Ser Ile Ser Thr Leu
                85                  90                  95

Asn Lys Arg Asp Tyr Ser Leu Gln Ile Gln Asn Val Asp Val Thr Asp
           100                 105                 110

Asp Gly Pro Tyr Thr Cys Ser Val Gln Thr Gln His Thr Pro Arg Thr
        115                 120                 125

Met Gln Val His Leu Thr Val Gln Val Pro Pro Lys Ile Tyr Asp Ile
    130                 135                 140

Ser Asn Asp Met Thr Val Asn Glu Gly Thr Asn Val Thr Leu Thr Cys
145                 150                 155                 160

Leu Ala Thr Gly Lys Pro Glu Pro Ser Ile Ser Trp Arg His Ile Ser
                165                 170                 175

Pro Ser Ala Lys Pro Phe Glu Asn Gly Gln Tyr Leu Asp Ile Tyr Gly
            180                 185                 190

Ile Thr Arg Asp Gln Ala Gly Glu Tyr Glu Cys Ser Ala Glu Asn Asp
        195                 200                 205

Val Ser Phe Pro Asp Val Arg Lys Val Lys Val Val Asn Phe Ala
    210                 215                 220

Pro Thr Ile Gln Glu Ile Lys Ser Gly Thr Val Thr Pro Gly Arg Ser
225                 230                 235                 240

Gly Leu Ile Arg Cys Glu Gly Ala Gly Val Pro Pro Pro Ala Phe Glu
                245                 250                 255

Trp Tyr Lys Gly Glu Lys Lys Leu Phe Asn Gly Gln Gln Gly Ile Ile
            260                 265                 270

Ile Gln Asn Phe Ser Thr Arg Ser Ile Leu Thr Val Thr Asn Val Thr
        275                 280                 285

Gln Glu His Phe Gly Asn Tyr Thr Cys Val Ala Ala Asn Lys Leu Gly
    290                 295                 300

Thr Thr Asn Ala Ser Leu Pro Leu Asn Pro Pro Ser Thr Ala Gln Tyr
305                 310                 315                 320

Gly Ile Thr Gly Ser Ala Asp Val Leu Phe Ser Cys Trp Tyr Leu Val
                325                 330                 335

Leu Thr Leu Ser Ser Phe Thr Ser Ile Phe Tyr Leu Lys Asn Ala Ile
            340                 345                 350
```

-continued

Leu Gln

<210> SEQ ID NO 11
<211> LENGTH: 3098
<212> TYPE: DNA
<213> ORGANISM: Homo sapiens
<220> FEATURE:
<221> NAME/KEY: CDS
<222> LOCATION: (223)..(1569)
<223> OTHER INFORMATION: LBFL164

<400> SEQUENCE: 11
```
gtttatcgcg cacatctcgc ggcgaggagg agaggccgga agggcgcccc agccccaagg      60
ctcctgcccc gcctgggcct ccggctttcg tttccccgca acgcttcgct ttcgtttccc     120
gctggcgcct ggctccctcc gggtttcgtt tcccgccggc gcctggctcc cgccaggttt     180
cgtttccgag gcggggccga gggcggcgtc gctgaggcgc cc         atg gcc ttc   231
                                                       Met Ala Phe
                                                         1
gcc cgc cgg ctc ctg cgc ggg cca ctg tcg ggg ccg ctg ctc ggg cgg      279
Ala Arg Arg Leu Leu Arg Gly Pro Leu Ser Gly Pro Leu Leu Gly Arg
      5                  10                  15
cgc ggg gtc tgc gct ggg gcc atg gct ccg ccg cgc cgc ttc gtc ctg      327
Arg Gly Val Cys Ala Gly Ala Met Ala Pro Pro Arg Arg Phe Val Leu
 20                  25                  30                  35
gag ctt ccc gac tgc acc ctg gct cac ttc gcc cta ggc gcc gac gcc      375
Glu Leu Pro Asp Cys Thr Leu Ala His Phe Ala Leu Gly Ala Asp Ala
                 40                  45                  50
ccc ggc gac gca gac gcc ccc gac ccc cgc ctg gcg gcg ctg ctg ggg      423
Pro Gly Asp Ala Asp Ala Pro Asp Pro Arg Leu Ala Ala Leu Leu Gly
             55                  60                  65
ccc ccg gag cgc agc tac tcg ctg tgc gtg ccc gtg acc ccg gac gcc      471
Pro Pro Glu Arg Ser Tyr Ser Leu Cys Val Pro Val Thr Pro Asp Ala
         70                  75                  80
ggc tgc ggg gcc cgg gtc cgg gcg gcg cgg ctg cac cag cgc ctg ctg      519
Gly Cys Gly Ala Arg Val Arg Ala Ala Arg Leu His Gln Arg Leu Leu
     85                  90                  95
cac cag ctg cgc cgc ggc ccc ttc cag cgg tgc cag ctg ctc agg ctg      567
His Gln Leu Arg Arg Gly Pro Phe Gln Arg Cys Gln Leu Leu Arg Leu
100                 105                 110                 115
ctc tgc tac tgc ccg ggc ggc cag gcc ggc ggc gca cag caa ggc ttc      615
Leu Cys Tyr Cys Pro Gly Gly Gln Ala Gly Gly Ala Gln Gln Gly Phe
                120                 125                 130
ctg ctg cgc gac ccc ctg gat gac cct gac acc cgg caa gcg ctg ctc      663
Leu Leu Arg Asp Pro Leu Asp Asp Pro Asp Thr Arg Gln Ala Leu Leu
            135                 140                 145
gag ctg ctg ggc gcc tgc cag gag gca cca cgc ccg cac ttg ggc gag      711
Glu Leu Leu Gly Ala Cys Gln Glu Ala Pro Arg Pro His Leu Gly Glu
        150                 155                 160
ttc gag gcc gac ccg cgc ggc cag ctg tgg cag cgc ctc tgg gag gtg      759
Phe Glu Ala Asp Pro Arg Gly Gln Leu Trp Gln Arg Leu Trp Glu Val
    165                 170                 175
caa gac ggc agg cgg ctg cag gtg ggc tgc gca cag gtc gtg ccc gtc      807
Gln Asp Gly Arg Arg Leu Gln Val Gly Cys Ala Gln Val Val Pro Val
180                 185                 190                 195
ccg gag ccc ccg ctg cac ccg gtg gtg cca gac ttg ccc agt tcc gtg      855
Pro Glu Pro Pro Leu His Pro Val Val Pro Asp Leu Pro Ser Ser Val
                200                 205                 210
gtc ttc ccg gac cgg gaa gcc gcc cgg gcc gtt ttg gag gag tgt acc      903
Val Phe Pro Asp Arg Glu Ala Ala Arg Ala Val Leu Glu Glu Cys Thr
            215                 220                 225
```

```
tcc ttt att cct gaa gcc cgg gca gtg ctt gac ctg gtc gac cag tgc      951
Ser Phe Ile Pro Glu Ala Arg Ala Val Leu Asp Leu Val Asp Gln Cys
            230                 235                 240 cca aaa cag atc cag aaa gga aag ttc cag gtt gtt gcc atc gaa gga      999
Pro Lys Gln Ile Gln Lys Gly Lys Phe Gln Val Val Ala Ile Glu Gly
        245                 250                 255 ctg gat gcc acg ggt aaa acc acg gtg acc cag tca gtg gca gat tca     1047
Leu Asp Ala Thr Gly Lys Thr Thr Val Thr Gln Ser Val Ala Asp Ser
260                 265                 270                 275 ctt aag gct gtc ctc tta aag tca cca ccc tct tgc att ggc cag tgg     1095
Leu Lys Ala Val Leu Leu Lys Ser Pro Pro Ser Cys Ile Gly Gln Trp
                280                 285                 290 agg aag atc ttt gat gat gaa cca act atc att aga aga gct ttt tac     1143
Arg Lys Ile Phe Asp Asp Glu Pro Thr Ile Ile Arg Arg Ala Phe Tyr
            295                 300                 305 tct ttg ggc aat tat att gtg gcc tcc gaa ata gct aaa gaa tct gcc     1191
Ser Leu Gly Asn Tyr Ile Val Ala Ser Glu Ile Ala Lys Glu Ser Ala
        310                 315                 320 aaa tct cct gtg att gta gac agg tac tgg cac agc acg gcc acc tat     1239
Lys Ser Pro Val Ile Val Asp Arg Tyr Trp His Ser Thr Ala Thr Tyr
325                 330                 335 gct ata gcc act gag gtg agt ggg ggt ctc cag cac ctg ccc cca gcc     1287
Ala Ile Ala Thr Glu Val Ser Gly Gly Leu Gln His Leu Pro Pro Ala
340                 345                 350                 355 cat cac cct gtg tac cag tgg cca gag gac ctg ctc aaa cct gac ctt     1335
His His Pro Val Tyr Gln Trp Pro Glu Asp Leu Leu Lys Pro Asp Leu
                360                 365                 370 atc ctg ctg ctc act gtg agt cct gag gag agg ttg cag agg ctg cag     1383
Ile Leu Leu Leu Thr Val Ser Pro Glu Glu Arg Leu Gln Arg Leu Gln
            375                 380                 385 ggc cgg ggc atg gag aag acc agg gaa gaa gca gaa ctt gag gcc aac     1431
Gly Arg Gly Met Glu Lys Thr Arg Glu Glu Ala Glu Leu Glu Ala Asn
        390                 395                 400 agt gtg ttt cgt caa aag gta gaa atg tcc tac cag cgg atg gag aat     1479
Ser Val Phe Arg Gln Lys Val Glu Met Ser Tyr Gln Arg Met Glu Asn
405                 410                 415 cct ggc tgc cat gtg gtt gat gcc agc ccc tcc aga gaa agg gtc ctg     1527
Pro Gly Cys His Val Val Asp Ala Ser Pro Ser Arg Glu Arg Val Leu
420                 425                 430                 435 cag acg gta tta agc cta atc cag aat agt ttt agt gaa ccg        t    1570
Gln Thr Val Leu Ser Leu Ile Gln Asn Ser Phe Ser Glu Pro
                440                 445 agttactctg gccaggtgcc acgtctaact agattagatg ttgtttgaaa catctacatc   1630
caccatttgt tatgcagtgt tcccaaattt ctgttctaca agcatgttgt gtggcagaaa   1690
actggagacc aggcatctta attttacttc agccatcgta ccctcttctg actgatggac   1750
ccgtcatcac aaaggtccct ctcatcatgt tccagtgaga ggccagcgat tgctttcttc   1810
ctggcatagt aaacattttc ttggaacata tgtttcactt aatcactacc aaatatctgg   1870
aagacctgtc ttactcagac agcaccaggt gtacagaagc agcagacaag atcttccaga   1930
tcagcaggga gaccccggag cctctgcttc tcctacactg gcatgctgat gagatcgtga   1990
catgcccaca ttggcttctt ccacatctgg ttgcactcgt catgatgggc tcgctgcatc   2050
tccctcagtc ccaaattcta gagccaagtg ttcctgcaga ggctgtctat gtgtcctggc   2110
tgcccaagga cactcctgca gagccatttt gggtaagga acacttacaa agaaggcatt   2170
gatcttgtgt ctgaggctca gagcccttttt gataggcttc tgagtcatat ataaagacat   2230
```

-continued

```
tcaagccaag atgctccaac tgcaaatata ccaaccttct ctgaattata ttttgcttat    2290
ttatatttct tttctttttt tctaaagtat ggctctgaat agaatgcaca ttttccattg    2350
aactggatgc atttcattta gccaatccag taatttattt atattaatct atacaatatg    2410
tttcctcagc ataggagcta tgattcatta attaaaagtg gagtcaaaac gctaaatgca    2470
atgtttgttg tgtattttca ttacacaaac ttaatttgtc ttgttaaata agtacagtgg    2530
atcttggagt gggatttctt ggtaaattat cttgcacttg aatgtctcat gattacatat    2590
gaaatcgctt tgacatatct ttagacagaa aaagtagct gagtgagggg gaaattatag     2650
agctgtgtga ctttagggag taggttgaac caggtgatta cctaaaattc cttccagttc    2710
aaaggcagat aaatctgtaa attattttat cctatctacc atttcttaag aagacattac    2770
tccaaaataa ttaaatttaa ggctttatca ggtctgcata tagaatctta aattctaata    2830
aagtttcatg ttaatgtcat aggattttta aaagagctat aggtaatttc tatataatat    2890
gtgtatatta aaatgtaatt gatttcagtt gaaagtattt taaagctgat aaatagcatt    2950
agggttcttt gcaatgtggt atctagctgt attattggtt ttatttactt taaacatttt    3010
gaaaagctta tactggcagc ctagaaaaac aaacaattaa tgtatcttta tgtccctggc    3070
acatgaataa actttgctgt ggtttact                                       3098
```

```
<210> SEQ ID NO 12
<211> LENGTH: 449
<212> TYPE: PRT
<213> ORGANISM: Homo sapiens

<400> SEQUENCE: 12
```

```
Met Ala Phe Ala Arg Arg Leu Leu Arg Gly Pro Leu Ser Gly Pro Leu
 1               5                  10                  15

Leu Gly Arg Arg Gly Val Cys Ala Gly Ala Met Ala Pro Pro Arg Arg
            20                  25                  30

Phe Val Leu Glu Leu Pro Asp Cys Thr Leu Ala His Phe Ala Leu Gly
        35                  40                  45

Ala Asp Ala Pro Gly Asp Ala Asp Ala Pro Asp Pro Arg Leu Ala Ala
    50                  55                  60

Leu Leu Gly Pro Pro Glu Arg Ser Tyr Ser Leu Cys Val Pro Val Thr
65                  70                  75                  80

Pro Asp Ala Gly Cys Gly Ala Arg Val Arg Ala Arg Leu His Gln
                85                  90                  95

Arg Leu Leu His Gln Leu Arg Arg Gly Pro Phe Gln Arg Cys Gln Leu
            100                 105                 110

Leu Arg Leu Leu Cys Tyr Cys Pro Gly Gly Gln Ala Gly Gly Ala Gln
        115                 120                 125

Gln Gly Phe Leu Leu Arg Asp Pro Leu Asp Asp Pro Asp Thr Arg Gln
    130                 135                 140

Ala Leu Leu Glu Leu Leu Gly Ala Cys Gln Glu Ala Pro Arg Pro His
145                 150                 155                 160

Leu Gly Glu Phe Glu Ala Asp Pro Arg Gly Gln Leu Trp Gln Arg Leu
                165                 170                 175

Trp Glu Val Gln Asp Gly Arg Arg Leu Gln Val Gly Cys Ala Gln Val
            180                 185                 190

Val Pro Val Pro Glu Pro Pro Leu His Pro Val Pro Asp Leu Pro
        195                 200                 205

Ser Ser Val Val Phe Pro Asp Arg Glu Ala Ala Arg Ala Val Leu Glu
    210                 215                 220
```

```
Glu Cys Thr Ser Phe Ile Pro Glu Ala Arg Ala Val Leu Asp Leu Val
225                 230                 235                 240

Asp Gln Cys Pro Lys Gln Ile Gln Lys Gly Lys Phe Gln Val Val Ala
            245                 250                 255

Ile Glu Gly Leu Asp Ala Thr Gly Lys Thr Val Thr Gln Ser Val
        260                 265                 270

Ala Asp Ser Leu Lys Ala Val Leu Leu Lys Ser Pro Ser Cys Ile
        275                 280                 285

Gly Gln Trp Arg Lys Ile Phe Asp Asp Glu Pro Thr Ile Ile Arg Arg
    290                 295                 300

Ala Phe Tyr Ser Leu Gly Asn Tyr Ile Val Ala Ser Glu Ile Ala Lys
305                 310                 315                 320

Glu Ser Ala Lys Ser Pro Val Ile Val Asp Arg Tyr Trp His Ser Thr
                325                 330                 335

Ala Thr Tyr Ala Ile Ala Thr Glu Val Ser Gly Gly Leu Gln His Leu
            340                 345                 350

Pro Pro Ala His His Pro Val Tyr Gln Trp Pro Glu Asp Leu Leu Lys
        355                 360                 365

Pro Asp Leu Ile Leu Leu Thr Val Ser Pro Glu Glu Arg Leu Gln
    370                 375                 380

Arg Leu Gln Gly Arg Gly Met Glu Lys Thr Arg Glu Glu Ala Glu Leu
385                 390                 395                 400

Glu Ala Asn Ser Val Phe Arg Gln Lys Val Glu Met Ser Tyr Gln Arg
                405                 410                 415

Met Glu Asn Pro Gly Cys His Val Val Asp Ala Ser Pro Ser Arg Glu
            420                 425                 430

Arg Val Leu Gln Thr Val Leu Ser Leu Ile Gln Asn Ser Phe Ser Glu
        435                 440                 445

Pro

<210> SEQ ID NO 13
<211> LENGTH: 1893
<212> TYPE: DNA
<213> ORGANISM: Homo sapiens
<220> FEATURE:
<221> NAME/KEY: CDS
<222> LOCATION: (418)..(1392)
<223> OTHER INFORMATION: LBFL167 Clone #20

<400> SEQUENCE: 13
agtccagctg ccgttaggcg ctgggatagt cgcacgctgg atgcatctac gtccgccgag    60
cccctggggc gaagaggccg cgtccgcctt catttgtggc cggtgcttcg cccccctgacc   120 cttcgccccc aaagaccagc tctaacgtga gcgcctcggc cgccctgccc cagcctcgta   180
cacgccgcca gcctcgccca gccggtgtcc ggagaccctc gggccgtgtc catttgtggg   240
caaagccagc ggggcaggct tggccagagt gcaccactcg gcgccgtccc aggcccgacg   300
ctctgggcgc gcccggaacc ccaggttcgc ggcccgtgtt ccgaccggc ggaggggggct   360 cagcggcccg atcccacgga agcgcgctcg gaggggtggg accggccgg accggag      417 atg gcc ccg cca gcg ggc ggg gcg gcg gcg gcg gcc tcg gac ttg ggc    465
Met Ala Pro Pro Ala Gly Gly Ala Ala Ala Ala Ala Ser Asp Leu Gly
1                   5                   10                  15 tcc gcc gca gtg ctc ttg gct gtg cac gcc gcg gtg agg ccg ctg ggc    513
Ser Ala Ala Val Leu Leu Ala Val His Ala Ala Val Arg Pro Leu Gly
                20                  25                  30
```

```
gcc ggg cca gac gcc gag gca cag ctg cgg agg ctg cag ctg agc gcg    561
Ala Gly Pro Asp Ala Glu Ala Gln Leu Arg Arg Leu Gln Leu Ser Ala
         35                  40                  45 gac cct gag cgg cct ggg cgc ttc cgg ctg gag ctg ctg ggc gcg gga    609
Asp Pro Glu Arg Pro Gly Arg Phe Arg Leu Glu Leu Leu Gly Ala Gly
 50                  55                  60 cct ggg gcg gtt aat ttg gag tgg ccc ctg gag tca gtt tcc tac acc    657
Pro Gly Ala Val Asn Leu Glu Trp Pro Leu Glu Ser Val Ser Tyr Thr
             65                  70                  75         80 atc cga ggc ccc acc cag cac gag cta cag cct cca cca gga ggg cct    705
Ile Arg Gly Pro Thr Gln His Glu Leu Gln Pro Pro Pro Gly Gly Pro
                 85                  90                  95 gga acc ctc agc ctg cac ttc ctc aac cct cag gaa gct cag cgg tgg    753
Gly Thr Leu Ser Leu His Phe Leu Asn Pro Gln Glu Ala Gln Arg Trp
            100                 105                 110 gca gtc cta gtc cga ggt gcc acc gtg gaa gga cag aat ggc agc aag    801
Ala Val Leu Val Arg Gly Ala Thr Val Glu Gly Gln Asn Gly Ser Lys
                115                 120                 125 agc aac tca cca cca gcc ttg ggc cca gaa gca tgc cct gtc tcc ctg    849
Ser Asn Ser Pro Pro Ala Leu Gly Pro Glu Ala Cys Pro Val Ser Leu
    130                 135                 140 ccc agt ccc ccg gaa gcc tcc aca ctc aag ggc cct cca cct gag gca    897
Pro Ser Pro Pro Glu Ala Ser Thr Leu Lys Gly Pro Pro Pro Glu Ala
145                 150                 155                 160 gat ctt cct agg agc cct gga aac ttg acg gag aga gaa gag ctg gca    945
Asp Leu Pro Arg Ser Pro Gly Asn Leu Thr Glu Arg Glu Glu Leu Ala
                165                 170                 175 ggg agc ctg gcc cgg gct att gca ggt gga gac gag aag ggg gca gcc    993
Gly Ser Leu Ala Arg Ala Ile Ala Gly Gly Asp Glu Lys Gly Ala Ala
            180                 185                 190 caa gtg gca gcc gtc ctg gcc cag cat cgt gtg gcc ctg agt gtt cag   1041
Gln Val Ala Ala Val Leu Ala Gln His Arg Val Ala Leu Ser Val Gln
                195                 200                 205 ctt cag gag gcc tgc ttc cca cct ggc ccc atc agg ctg cag gtc aca   1089
Leu Gln Glu Ala Cys Phe Pro Pro Gly Pro Ile Arg Leu Gln Val Thr
    210                 215                 220 ctt gaa gac gct gcc tct gcc gca tcc gcc gcg tcc tct gca cac gtt   1137
Leu Glu Asp Ala Ala Ser Ala Ala Ser Ala Ala Ser Ser Ala His Val
225                 230                 235                 240 gcc ctg cag gtc cac ccc cac tgc act gtt gca gct ctc cag gag cag   1185
Ala Leu Gln Val His Pro His Cys Thr Val Ala Ala Leu Gln Glu Gln
                245                 250                 255 gtg ttc tca gag ctc ggt ttc ccg cca gcc gtg caa cgc tgg gtc atc   1233
Val Phe Ser Glu Leu Gly Phe Pro Pro Ala Val Gln Arg Trp Val Ile
            260                 265                 270 gga cgg tgc ctg tgt gtg cct gag cgc agc ctt gcc tct tac ggg gtt   1281
Gly Arg Cys Leu Cys Val Pro Glu Arg Ser Leu Ala Ser Tyr Gly Val
        275                 280                 285 cgg cag gat ggg gac cct gct ttc ctc tac ttg ctg tca gct cct cga   1329
Arg Gln Asp Gly Asp Pro Ala Phe Leu Tyr Leu Leu Ser Ala Pro Arg
    290                 295                 300 gaa gcc cca ggt cag tcc tcg atg ggg gtg ggg tgt ggg agg tgg ggt   1377
Glu Ala Pro Gly Gln Ser Ser Met Gly Val Gly Cys Gly Arg Trp Gly
305                 310                 315                 320 gca gcc cca cag tcc    tgagctcc acccctcag ccacaggacc tagccctcag   1430
Ala Ala Pro Gln Ser
            325 caccccaga agatggacgg ggaacttgga cgcttgtttc cccatcatt ggggctaccc    1490 ccaggccccc agccagctgc ctccagcctg cccagtccac tccagcccag ctggtcctgt   1550
```

```
ccttcctgca ccttcatcaa tgccccagac cgccctggct gtgagatgtg tagcacccag    1610
aggccctgca cttgggaccc ccttgctgca gcttccacct agcagccacc agaggtacca    1670
gaggtggcac aggcagggga ggtgggggc cagggcagaa tccacaggaa tgacccagct     1730
cctcccccac aggttacaag gggagagtgg cccttccctc acaagtccga catctccagg    1790
cccccactga actccgggga cctctactga ctgcttgctg ggacagtcac cagggttggg    1850
gggaagggcc acaaaatgaa accattaaag acccttaaga gcc                      1893
```

<210> SEQ ID NO 14
<211> LENGTH: 325
<212> TYPE: PRT
<213> ORGANISM: Homo sapiens

<400> SEQUENCE: 14

```
Met Ala Pro Pro Ala Gly Gly Ala Ala Ala Ala Ser Asp Leu Gly
 1               5                  10                  15

Ser Ala Ala Val Leu Leu Ala Val His Ala Ala Val Arg Pro Leu Gly
                20                  25                  30

Ala Gly Pro Asp Ala Glu Ala Gln Leu Arg Arg Leu Gln Leu Ser Ala
            35                  40                  45

Asp Pro Glu Arg Pro Gly Arg Phe Arg Leu Glu Leu Gly Ala Gly
    50                  55                  60

Pro Gly Ala Val Asn Leu Glu Trp Pro Leu Glu Ser Val Ser Tyr Thr
65                  70                  75                  80

Ile Arg Gly Pro Thr Gln His Glu Leu Gln Pro Pro Gly Gly Pro
                85                  90                  95

Gly Thr Leu Ser Leu His Phe Leu Asn Pro Gln Glu Ala Gln Arg Trp
            100                 105                 110

Ala Val Leu Val Arg Gly Ala Thr Val Glu Gly Gln Asn Gly Ser Lys
        115                 120                 125

Ser Asn Ser Pro Pro Ala Leu Gly Pro Glu Ala Cys Pro Val Ser Leu
    130                 135                 140

Pro Ser Pro Pro Glu Ala Ser Thr Leu Lys Gly Pro Pro Glu Ala
145                 150                 155                 160

Asp Leu Pro Arg Ser Pro Gly Asn Leu Thr Glu Arg Glu Leu Ala
                165                 170                 175

Gly Ser Leu Ala Arg Ala Ile Ala Gly Gly Asp Glu Lys Gly Ala Ala
            180                 185                 190

Gln Val Ala Ala Val Leu Ala Gln His Arg Val Ala Leu Ser Val Gln
        195                 200                 205

Leu Gln Glu Ala Cys Phe Pro Pro Gly Pro Ile Arg Leu Gln Val Thr
    210                 215                 220

Leu Glu Asp Ala Ala Ser Ala Ala Ser Ala Ala Ser Ser Ala His Val
225                 230                 235                 240

Ala Leu Gln Val His Pro His Cys Thr Val Ala Ala Leu Gln Glu Gln
                245                 250                 255

Val Phe Ser Glu Leu Gly Phe Pro Pro Ala Val Gln Arg Trp Val Ile
            260                 265                 270

Gly Arg Cys Leu Cys Val Pro Glu Arg Ser Leu Ala Ser Tyr Gly Val
        275                 280                 285

Arg Gln Asp Gly Asp Pro Ala Phe Leu Tyr Leu Leu Ser Ala Pro Arg
    290                 295                 300

Glu Ala Pro Gly Gln Ser Ser Met Gly Val Gly Cys Gly Arg Trp Gly
```

```
                    305                 310                 315                 320

Ala Ala Pro Gln Ser
            325

<210> SEQ ID NO 15
<211> LENGTH: 1597
<212> TYPE: DNA
<213> ORGANISM: Homo sapiens
<220> FEATURE:
<221> NAME/KEY: CDS
<222> LOCATION: (271)..(1431)
<223> OTHER INFORMATION: LBFL167 Clone #46

<400> SEQUENCE: 15
gtgagcgcct cggccgccct gccccagcct cgtacacgcc gccagctcgc ccagccggtg      60
tccggagacc ctcgggccgt gtccatttgt gggcaaagcc agcggggcag gcttggccag     120
agtgcaccac tcggcgccgt cccaggcccg acgctctggg cgcgcccgga accccaggtt     180
cgcggcccgt gtttccgacc ggcggagggg gctcagcggc ccgatcccac ggaagcgcgc     240
tcggaggggt gggacccggc cggaccggag atg gcg ccg cca gcg ggc ggg gcg     294
                                   Met Ala Pro Pro Ala Gly Gly Ala
                                     1               5 gcg gcg gcg gcc tcg gac ttg ggc tcc gcc gca gtg ctc ttg gct gtg     342
Ala Ala Ala Ala Ser Asp Leu Gly Ser Ala Ala Val Leu Leu Ala Val
         10                  15                  20 cac gcc gcg gtg agg ccg ctg ggc gcc ggg cca gac gcc gag gca cag     390
His Ala Ala Val Arg Pro Leu Gly Ala Gly Pro Asp Ala Glu Ala Gln
 25                  30                  35                  40 ctg cgg agg ctg cag ctg agc gcg gac cct gag agg cct ggg cgc ttc     438
Leu Arg Arg Leu Gln Leu Ser Ala Asp Pro Glu Arg Pro Gly Arg Phe
                 45                  50                  55 cgg ctg gag ctg ctg ggc gcg gga cct ggg gcg gtt aat ttg gag tgg     486
Arg Leu Glu Leu Leu Gly Ala Gly Pro Gly Ala Val Asn Leu Glu Trp
             60                  65                  70 ccc ctg gag tca gtt tcc tac acc atc cga ggc ccc acc cag cac gag     534
Pro Leu Glu Ser Val Ser Tyr Thr Ile Arg Gly Pro Thr Gln His Glu
         75                  80                  85 cta cag cct cca cca gga ggg cct gga acc ctc agc ctg cac ttc ctc     582
Leu Gln Pro Pro Pro Gly Gly Pro Gly Thr Leu Ser Leu His Phe Leu
     90                  95                 100 aac cct cag gaa gct cag cgg tgg gca gtc cta gtc cga ggt gcc acc     630
Asn Pro Gln Glu Ala Gln Arg Trp Ala Val Leu Val Arg Gly Ala Thr
105                 110                 115                 120 gtg gaa gga cag aat ggc agc aag agc aac tca cca cca gcc ttg ggc     678
Val Glu Gly Gln Asn Gly Ser Lys Ser Asn Ser Pro Pro Ala Leu Gly
                125                 130                 135 cca gaa gca tgc cct gtc tcc ctg ccc agt ccc ccg gaa gcc tcc aca     726
Pro Glu Ala Cys Pro Val Ser Leu Pro Ser Pro Pro Glu Ala Ser Thr
            140                 145                 150 ctc aag ggc cct cca cct gag gca gat ctt cct agg agc cct gga aac     774
Leu Lys Gly Pro Pro Pro Glu Ala Asp Leu Pro Arg Ser Pro Gly Asn
        155                 160                 165 ttg acg gag aga gaa gag ctg gca ggg agc ctg gcc cgg gct att gca     822
Leu Thr Glu Arg Glu Glu Leu Ala Gly Ser Leu Ala Arg Ala Ile Ala
    170                 175                 180 ggt gga gac gag aag ggg gca gcc caa gtg gca gcc gtc ctg gcc cag     870
Gly Gly Asp Glu Lys Gly Ala Ala Gln Val Ala Ala Val Leu Ala Gln
185                 190                 195                 200 cat cgt gtg gcc ctg agt gtt cag ctt cag gag gcc tgc ttc cca cct     918
His Arg Val Ala Leu Ser Val Gln Leu Gln Glu Ala Cys Phe Pro Pro
```

-continued

```
                205                 210                 215
ggc ccc atc agg ctg cag gtc aca ctt gaa gac gct gcc tct gcc gca        966
Gly Pro Ile Arg Leu Gln Val Thr Leu Glu Asp Ala Ala Ser Ala Ala
            220                 225                 230 tcc gcc gcg tcc tct gca cac gtt gcc ctg cag gtc cac ccc cac tgc       1014
Ser Ala Ala Ser Ser Ala His Val Ala Leu Gln Val His Pro His Cys
        235                 240                 245 act gtt gca gct ctc cag gag cag gtg ttc tca gag ctc ggt ttc ccg       1062
Thr Val Ala Ala Leu Gln Glu Gln Val Phe Ser Glu Leu Gly Phe Pro
    250                 255                 260 cca gcc gtg caa cgc tgg gtc atc gga cgg tgc ctg tgt gtg cct gag       1110
Pro Ala Val Gln Arg Trp Val Ile Gly Arg Cys Leu Cys Val Pro Glu
265                 270                 275                 280 cgc agc ctt gcc tct tac ggg gtt cgg cag gat ggg gac cct gct ttc       1158
Arg Ser Leu Ala Ser Tyr Gly Val Arg Gln Asp Gly Asp Pro Ala Phe
                285                 290                 295 ctc tac ttg ctg tca gct cct cga gaa gcc cca gcc aca gga cct agc       1206
Leu Tyr Leu Leu Ser Ala Pro Arg Glu Ala Pro Ala Thr Gly Pro Ser
            300                 305                 310 cct cag cac ccc cag aag atg gac ggg gaa ctt gga cgc ttg ttt ccc       1254
Pro Gln His Pro Gln Lys Met Asp Gly Glu Leu Gly Arg Leu Phe Pro
        315                 320                 325 cca tca ttg ggg cta ccc cca ggc ccc cag cca gct gcc tcc agc ctg       1302
Pro Ser Leu Gly Leu Pro Pro Gly Pro Gln Pro Ala Ala Ser Ser Leu
    330                 335                 340 ccc agt cca ctc cag ccc agc tgg tcc tgt cct tcc tgc acc ttc atc       1350
Pro Ser Pro Leu Gln Pro Ser Trp Ser Cys Pro Ser Cys Thr Phe Ile
345                 350                 355                 360 aat gcc cca gac cgc cct ggc tgt gag atg tgt agc acc cag agg ccc       1398
Asn Ala Pro Asp Arg Pro Gly Cys Glu Met Cys Ser Thr Gln Arg Pro
                365                 370                 375 tgc act tgg gac ccc ctt gct gca gct tcc acc    tagcagcca ccagaggtta  1450
Cys Thr Trp Asp Pro Leu Ala Ala Ala Ser Thr
            380                 385 caaggggaga gtggcccttc cctcacaagt ccgacatctc caggccccca ctgaactccg    1510
gggacctcta ctgactgctt gctgggacag tcaccagggt tggggggaag ggccacaaaa    1570
tgaaaccatt aaagacccct aagagcc                                         1597
```

<210> SEQ ID NO 16
<211> LENGTH: 387
<212> TYPE: PRT
<213> ORGANISM: Homo sapiens

<400> SEQUENCE: 16

```
Met Ala Pro Pro Ala Gly Gly Ala Ala Ala Ala Ser Asp Leu Gly
 1               5                  10                  15

Ser Ala Ala Val Leu Leu Ala Val His Ala Ala Val Arg Pro Leu Gly
                20                  25                  30

Ala Gly Pro Asp Ala Glu Ala Gln Leu Arg Arg Leu Gln Leu Ser Ala
            35                  40                  45

Asp Pro Glu Arg Pro Gly Arg Phe Arg Leu Glu Leu Gly Ala Gly
        50                  55                  60

Pro Gly Ala Val Asn Leu Glu Trp Pro Leu Glu Ser Val Ser Tyr Thr
    65                  70                  75                  80

Ile Arg Gly Pro Thr Gln His Glu Leu Gln Pro Pro Gly Gly Pro
                85                  90                  95

Gly Thr Leu Ser Leu His Phe Leu Asn Pro Gln Glu Ala Gln Arg Trp
```

```
                      100                 105                 110
Ala Val Leu Val Arg Gly Ala Thr Val Glu Gly Gln Asn Gly Ser Lys
            115                 120                 125

Ser Asn Ser Pro Pro Ala Leu Gly Pro Glu Ala Cys Pro Val Ser Leu
    130                 135                 140

Pro Ser Pro Glu Ala Ser Thr Leu Lys Gly Pro Pro Glu Ala
145                 150                 155                 160

Asp Leu Pro Arg Ser Pro Gly Asn Leu Thr Glu Arg Glu Leu Ala
                165                 170                 175

Gly Ser Leu Ala Arg Ala Ile Ala Gly Gly Asp Glu Lys Gly Ala Ala
            180                 185                 190

Gln Val Ala Ala Val Leu Ala Gln His Arg Val Ala Leu Ser Val Gln
            195                 200                 205

Leu Gln Glu Ala Cys Phe Pro Pro Gly Pro Ile Arg Leu Gln Val Thr
            210                 215                 220

Leu Glu Asp Ala Ala Ser Ala Ala Ser Ala Ser Ser Ala His Val
225                 230                 235                 240

Ala Leu Gln Val His Pro His Cys Thr Val Ala Ala Leu Gln Glu Gln
                245                 250                 255

Val Phe Ser Glu Leu Gly Phe Pro Pro Ala Val Gln Arg Trp Val Ile
            260                 265                 270

Gly Arg Cys Leu Cys Val Pro Glu Arg Ser Leu Ala Ser Tyr Gly Val
            275                 280                 285

Arg Gln Asp Gly Asp Pro Ala Phe Leu Tyr Leu Leu Ser Ala Pro Arg
            290                 295                 300

Glu Ala Pro Ala Thr Gly Pro Ser Pro Gln His Pro Gln Lys Met Asp
305                 310                 315                 320

Gly Glu Leu Gly Arg Leu Phe Pro Pro Ser Leu Gly Leu Pro Pro Gly
                325                 330                 335

Pro Gln Pro Ala Ala Ser Ser Leu Pro Ser Pro Leu Gln Pro Ser Trp
            340                 345                 350

Ser Cys Pro Ser Cys Thr Phe Ile Asn Ala Pro Asp Arg Pro Gly Cys
            355                 360                 365

Glu Met Cys Ser Thr Gln Arg Pro Cys Thr Trp Asp Pro Leu Ala Ala
            370                 375                 380

Ala Ser Thr
385

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
gctgaagcag gaaaatcgct t                                            21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
tgagacggag tctcactcgg t                                            21
```

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
gtttttccta attttggcat gaac                                    24

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
cgcccaagct tttcctttt                                          19

<210> SEQ ID NO 21
<211> LENGTH: 26
<212> TYPE: DNA
<213> ORGANISM: Artificial Sequence
<220> FEATURE:
<223> OTHER INFORMATION: Primer

<400> SEQUENCE: 21
caccctttgc ctctgtcact tccgca                                  26

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
gctggagcac caggactgca ttg                                     23

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
ggagctgagc agcagtgtaa tgaa                                    24

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
gaggcctgcc tgaaggagga gcttc                                   25

<210> SEQ ID NO 25
<211> LENGTH: 26
<212> TYPE: DNA
<213> ORGANISM: Artificial Sequence
<220> FEATURE:

```
<223> OTHER INFORMATION: Primer

<400> SEQUENCE: 25
tctggaagta gtgcagacgc ctcagg                                    26

<210> SEQ ID NO 26
<211> LENGTH: 26
<212> TYPE: DNA
<213> ORGANISM: Artificial Sequence
<220> FEATURE:
<223> OTHER INFORMATION: Primer

<400> SEQUENCE: 26
agccaacgtc ggctttgtta tccagc                                    26

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
gctgtcagat atgatggttc tggac                                     25

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
ccagcctcac cactgttggg ttgc                                      24

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
cattctctga gctgtattag tgt                                       23

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
cctgagctgg aatgacctgc a                                         21

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
ctttgtgttg gctgcagcca ca                                        22
```

```
<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
tgaggagaga ctttgctgac tggt                                              24

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
gtcctgtctg gcggtgccga                                                   20

<210> SEQ ID NO 34
<211> LENGTH: 42
<212> TYPE: DNA
<213> ORGANISM: Artificial Sequence
<220> FEATURE:
<223> OTHER INFORMATION: Primer

<400> SEQUENCE: 34
gctccaggat ccctgtcac ctgggccttc tgccttttgg ct                           42

<210> SEQ ID NO 35
<211> LENGTH: 28
<212> TYPE: DNA
<213> ORGANISM: Artificial Sequence
<220> FEATURE:
<223> OTHER INFORMATION: Primer

<400> SEQUENCE: 35
ccatatggag aggagagcag cgggccca                                          28

<210> SEQ ID NO 36
<211> LENGTH: 23
<212> TYPE: DNA
<213> ORGANISM: Artificial Sequence
<220> FEATURE:
<223> OTHER INFORMATION: Primer

<400> SEQUENCE: 36
gaaggaggaa catggagagg aga                                               23

<210> SEQ ID NO 37
<211> LENGTH: 27
<212> TYPE: DNA
<213> ORGANISM: Artificial Sequence
<220> FEATURE:
<223> OTHER INFORMATION: Primer

<400> SEQUENCE: 37
ccatatgccc cgggtagtct actgcat                                           27

<210> SEQ ID NO 38
<211> LENGTH: 33
<212> TYPE: DNA
<213> ORGANISM: Artificial Sequence
<220> FEATURE:
<223> OTHER INFORMATION: Primer
```

```
<400> SEQUENCE: 38
gtcgactcga gtcacttccg caaaaacttc ttg                                    33

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
tccattccga aggctctcct cc                                                22

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
gtctgtgtga cggaaatgta agc                                               23

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
gaaggtcgaa ggcagaccga tgt                                               23

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
gaatgtgtca gagacaagtg cagc                                              24

<210> SEQ ID NO 43
<211> LENGTH: 26
<212> TYPE: DNA
<213> ORGANISM: Artificial Sequence
<220> FEATURE:
<223> OTHER INFORMATION: Primer

<400> SEQUENCE: 43
tgtagaaact cttggactaa tggagg                                            26

<210> SEQ ID NO 44
<211> LENGTH: 29
<212> TYPE: DNA
<213> ORGANISM: Artificial Sequence
<220> FEATURE:
<223> OTHER INFORMATION: Primer

<400> SEQUENCE: 44
gtatgcatca gaattcccta tagatcttt                                         29

<210> SEQ ID NO 45
<211> LENGTH: 21
```

```
<212> TYPE: DNA
<213> ORGANISM: Artificial Sequence
<220> FEATURE:
<223> OTHER INFORMATION: Primer

<400> SEQUENCE: 45
tagatgtttg ggcaacagcc t                                              21

<210> SEQ ID NO 46
<211> LENGTH: 32
<212> TYPE: DNA
<213> ORGANISM: Artificial Sequence
<220> FEATURE:
<223> OTHER INFORMATION: Primer

<400> SEQUENCE: 46
ttccttcacc aaaggcatcc agccattcta tg                                  32

<210> SEQ ID NO 47
<211> LENGTH: 28
<212> TYPE: DNA
<213> ORGANISM: Artificial Sequence
<220> FEATURE:
<223> OTHER INFORMATION: Primer

<400> SEQUENCE: 47
aaatgtctga ttaccccatt ttatcagt                                       28

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
taatcctgaa atgaacagct aaca                                           24

<210> SEQ ID NO 49
<211> LENGTH: 30
<212> TYPE: DNA
<213> ORGANISM: Artificial Sequence
<220> FEATURE:
<223> OTHER INFORMATION: Primer

<400> SEQUENCE: 49
taatgttaga gtaacagcat tttccttcaa                                     30

<210> SEQ ID NO 50
<211> LENGTH: 29
<212> TYPE: DNA
<213> ORGANISM: Artificial Sequence
<220> FEATURE:
<223> OTHER INFORMATION: Primer

<400> SEQUENCE: 50
tgccccacac taactcagtt cttgtgatg                                      29

<210> SEQ ID NO 51
<211> LENGTH: 29
<212> TYPE: DNA
<213> ORGANISM: Artificial Sequence
<220> FEATURE:
<223> OTHER INFORMATION: Primer

<400> SEQUENCE: 51
```

```
aaggctttat caggtctgca tatagaatc                              29

<210> SEQ ID NO 52
<211> LENGTH: 28
<212> TYPE: DNA
<213> ORGANISM: Artificial Sequence
<220> FEATURE:
<223> OTHER INFORMATION: Primer

<400> SEQUENCE: 52
gcaaagaacc ctaatgctat ttatcagc                               28

<210> SEQ ID NO 53
<211> LENGTH: 22
<212> TYPE: DNA
<213> ORGANISM: Artificial Sequence
<220> FEATURE:
<223> OTHER INFORMATION: Primer

<400> SEQUENCE: 53
gagaagacca gggaagaagc ag                                     22

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
ggacggggaa cttggacgc                                         19

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
aagtgcaggg cctctgggtg                                        20

<210> SEQ ID NO 56
<211> LENGTH: 19
<212> TYPE: DNA
<213> ORGANISM: Artificial Sequence
<220> FEATURE:
<223> OTHER INFORMATION: Primer

<400> SEQUENCE: 56
cgctgggtca tcggacggt                                         19
```

GENE FAMILIES ASSOCIATED WITH CANCERS

FIELD OF THE INVENTION

The present invention relates to the changes in gene expression in human tissues from cancer patients. The invention specifically relates to human genes which are differentially expressed in cancer tissues of breast, colon, esophagus, kidney, liver, lung, lymph node, ovary, pancreas, prostate, rectum, and/or stomach compared to corresponding normal tissues.

BACKGROUND OF THE INVENTION

In the United States, more than one million new cancer cases are diagnosed and about half million people die of cancer. The causes of cancer are many and varied, and include genetic predisposition, environmental influences, infectious agents and ageing. These transform normal cells into cancerous ones by derailing a wide spectrum of regulatory and downstream effector pathways. Several essential alterations in cell physiology collectively dictate malignant growth: self-sufficiency in growth signals, insensitivity to growth-inhibitory signals, evasion of programmed cell death, limitless replicative potential, sustained angiogenesis, and tissue invasion and metastasis (Hanahan and Weinberg (2000), *Cell* 100:57-70).

To date, researchers have been able to identify many genetic alterations believed to underlie tumor development. These genetic alterations include amplification of oncogenes and mutations that result in the loss of tumor suppressor genes. Oncogenes were initially identified as genes carried by viruses that cause transformation of their target cells. A major class of the viral oncogenes have cellular counterparts that are involved in normal cell functions. The cellular genes are called proto-oncogene, and in certain cases their mutation or aberrant in the cell is associated with tumor formation. The generation of a oncogene represents a gain-of-function in which a cellular proto-oncogene is inappropriately activated. This can involve a mutational change in the protein, or constitutive activation, over-expression, or failure to turn off expression at the appropriate time. About 100 oncogenes have been identified. Examples of oncogenes include, but are not limited to, ras, fos, myc, abl, and myb (Ponder (2001), *Nature* 411:336-341). Tumor suppressor genes, in their wild-type alleles, express proteins that suppress abnormal cellular proliferation. When the gene coding for a tumor suppressor protein is mutated or deleted, the resulting mutant protein or the complete lack of tumor suppressor protein expression may fail to correctly regulate cellular proliferation, and abnormal proliferation may take place, particularly if there is already existing damage to the cellular regulatory mechanism. A number of well-studied human tumors and tumor cell lines have missing or non-functional tumor suppressor genes. Examples of tumor suppressor genes include, but are not limited to, the retinoblastoma susceptibility gene or RB gene, the p53 gene, the deletion in colon carcinoma (DCC) gene and the neurofibromatosis type 1 (NF-1) tumor suppressor gene (Weinberg (1991), *Science* 254:1138-1146). Loss-of-function or inactivation of tumor suppressor genes may play a central role in the initiation and/or progression of a significant number of human cancers.

The utilization of genome-wide expression profiles to classify tumors, to identify drug targets, to identify diagnostic markers and/or to gain further insights into the consequences of chemotherapeutic treatments could facilitate the design of more efficacious stratagems for treating a variety of cancers. Initial studies utilizing gene expression patterns to identify subtypes of cancer produced rather intriguing results (see Perou et al. (1999), *Proc Natl Acad Sci USA* 96:9212-9217; Golub et al. (1999), *Science* 286:531-537; Alizadeh et al. (2000), *Nature* 403:503-511; Alon et al. (1999), *Proc Natl Acad Sci USA* 96:6745-6750; and Bittner et al. (2000), *Nature* 406:536-540; Perou et al. (2000), *Nature* 406:747-752). Molecular classification of B-cell lymphoma by gene expression profiling elucidated clinically distinct diffuse large-B-cell lymphoma subgroups (see Alizadeh et al., supra). In breast cancer, studies utilizing limited numbers of genes (8,102 genes) have classified tumors into subtypes based on gene expression profiles, and this study indicated a diversity of molecular phenotypes associated with breast tumors (see Perou et al., supra). In addition, the expression profiling has enabled researchers to map tissue-specific expression levels for thousands of genes (Alon et al. (1999), *Proc Natl Acad Sci USA* 96:6745-6750; Iyer et al. (1999), *Science* 283:83-87; Khan et al. (1998), *Cancer Res* 58:5009-5013; Lee et al. (1999), *Science* 285:1390-1393; Wang et al. (1999), *Gene* 229:101-108; Whitney et al. (1999), *Ann Neurol* 46:425-428). Although these studies have demonstrated that expression profiling may be used to produce improvements in diagnosis of human diseases such as cancer, as well as in the development of improved therapeutic strategies, further studies are needed.

Although cancers are diverse and heterogeneous as they are derived from numerous tissues and multiple etiologic factors, it has been suggested that underlying this variability lies a relatively small number of critical events whose convergence is required for the development of any and all cancers (Evan and Vousden (2001), *Nature* 411:342-348). Accordingly, there exists a need for the comprehensive investigation of the changes in global gene expression levels in many different types of cancers to identify critical molecular markers associated with the development and progression of cancer. There remains a need in the art for materials and methods that permit a more accurate diagnosis of cancer. In addition, there remains a need in the art for methods to treat and methods to identify agents that can effectively treat this disease. The present invention meets these and other needs.

SUMMARY OF THE INVENTION

The present invention is based on new genes that are differentially expressed in cancer tissues compared to normal tissues, hereinafter LFG1, LFG2, LFG3, LFG4, LFG5, LFG6, respectively. The invention includes isolated nucleic acid molecules comprising SEQ ID NO: 1, 3, 5, 7, 9, 11, 13 or 15 or the complement thereof.

The present invention further includes the nucleic acid molecules operably linked to one or more expression control elements, including vectors comprising the isolated nucleic acid molecules. The invention further includes host cells transformed to contain the nucleic acid molecules of the invention and methods for producing a protein comprising the step of culturing a host cell transformed with a nucleic acid molecule of the invention under conditions in which the protein is expressed.

The invention further provides an isolated polypeptide selected from the group consisting of an isolated polypeptide comprising the amino acid sequence of SEQ ID NO: 2, 4, 6, 8, 10, 12, 14 or 16, an isolated polypeptide comprising a fragment of at least 10 amino acids of SEQ ID NO: 2, 4, 6, 8, 10, 12, 14 or 16, an isolated polypeptide comprising conservative amino acid substitutions of SEQ ID NO: 2, 4, 6, 8, 10, 12, 14 or 16 and an isolated polypeptide comprising naturally occurring amino acid sequence variants of SEQ ID NO: 2, 4, 6, 8, 10, 12, 14 or 16. Polypeptides of the invention also include polypeptides with an amino acid sequence having at least about 50%, 60%, 70% or 75% amino acid sequence identity with the sequence set forth in SEQ ID NO: 2, 4, 6, 8, 10, 12, 14 or 16, preferably at least about 80%, more preferably at least about 90-95%, and most preferably at least about 95-98% sequence identity with the sequence set forth in SEQ ID NO: 2, 4, 6, 8, 10, 12, 14 or 16.

The present invention further provides methods of identifying other members of the polypeptide family of the invention. Specifically, the nucleic acid sequence of SEQ ID NO: 1, 3, 5, 7, 9, 11, 13 or 15 can be used as a probe, or to generate PCR primers, in methods to identify nucleic acid molecules that encode other members of the LFG1, LFG2, LFG3, LFG4, LFG5 or LFG6 family of proteins.

The invention further provides an isolated antibody or antigen-binding antibody fragment that specifically binds to a polypeptide of the invention, including monoclonal and polyclonal antibodies.

The invention further provides methods of identifying an agent which modulates the expression of a nucleic acid molecule encoding a protein of the invention, comprising: exposing cells which express the nucleic acid molecule to the agent; and determining whether the agent modulates expression of said nucleic acid molecule, thereby identifying an agent which modulates the expression of a nucleic acid molecule encoding the protein.

The invention further provides methods of identifying an agent which modulates the level of or at least one activity of a protein of the invention, comprising: exposing cells which express the protein to the agent; and determining whether the agent modulates the level of or at least one activity of said protein, thereby identifying an agent which modulates the level of or at least one activity of the protein.

The present invention further provides methods of modulating the expression of a nucleic acid molecule encoding a protein of the invention, comprising the step of administering an effective amount of an agent which modulates the expression of a nucleic acid molecule encoding the protein. The invention also provides methods of modulating at least one activity of a protein of the invention, comprising the step of administering an effective amount of an agent which modulates at least one activity of the protein of the invention.

The invention further provides methods of identifying binding partners for a protein of the invention, comprising the steps of exposing said protein to a potential binding partner; and determining if the potential binding partner binds to said protein, thereby identifying binding partners for the protein.

The present invention further provides methods to identify agents that can block or modulate the association of a protein of the invention with a binding partner. Specifically, an agent can be tested for the ability to block, reduce or otherwise modulate the association of a protein of invention with a binding partner by contacting said protein, or a fragment thereof, and a binding partner with a test agent and determining whether the test agent blocks or reduces the binding of the protein of invention to the binding partner.

The present invention further provides methods for reducing or blocking the association of a protein of invention with one or more of its binding partners, comprising the step of administrating an effective amount of an agent which reduces or blocks the binding of said protein to the binding partner. The method can utilize an agent that binds to the protein of invention or to the binding partner.

In accordance with another aspect of the invention, the proteins of the invention can be used as starting points for rational drug design to provide ligands, therapeutic drugs or other types of small chemical molecules. Alternatively, small molecules or other compounds identified by the above-described screening assays may serve as "lead compounds" in rational drug design.

The present invention further relates to a process for treating cancer comprising inserting into a cancerous cell a nucleic acid construct comprising the nucleic acid molecules of the invention operably linked to a promoter or enhancer element such that expression of said nucleic acid molecule causes suppression of said cancer.

The present invention further includes non-human transgenic animals modified to contain the nucleic acid molecules of the invention, or non-human transgenic animals modified to contain the mutated nucleic acid molecules such that expression of the encoded polypeptides of the invention is prevented.

The present invention also includes non-human transgenic animals in which all or a portion of a gene comprising all or a portion of SEQ ID NO: 1, 3, 5, 7, 9, 11, 13 or 15 has been knocked out or deleted from the genome of the animal.

The invention further provides methods of diagnosing cancers, comprising the steps of acquiring a tissue, blood, urine or other sample from a subject and determining the level of expression of a nucleic acid molecule of the invention or polypeptide of the invention.

The invention further includes compositions comprising a diluent and a polypeptide or protein selected from the group consisting of an isolated polypeptide comprising the amino acid sequence of SEQ ID NO: 2, 4, 6, 8, 10, 12, 14 or 16, an isolated polypeptide comprising a fragment of at least 10 amino acids of SEQ ID NO: 2, 4, 6, 8, 10, 12, 14 or 16, an isolated polypeptide comprising conservative amino acid substitutions of SEQ ID NO: 2, 4, 6, 8, 10, 12, 14 or 16, naturally occurring amino acid sequence variants of SEQ ID NO: 2, 4, 6, 8, 10, 12, 14 or 16 and an isolated polypeptide with an amino acid sequence having at least about 50%, 60%, 70% or 75% amino acid sequence identity with the sequence set forth in SEQ ID NO: 2, 4, 6, 8, 10, 12, 14 or 16, preferably at least about 80%, more preferably at least about 90-95%, and most preferably at least about 95-98% sequence identity with the sequence set forth in SEQ ID NO: 2, 4, 6, 8, 10, 12, 14 or 16.

DETAILED DESCRIPTION OF THE PREFERRED EMBODIMENT

I. General Description

Figure 1:
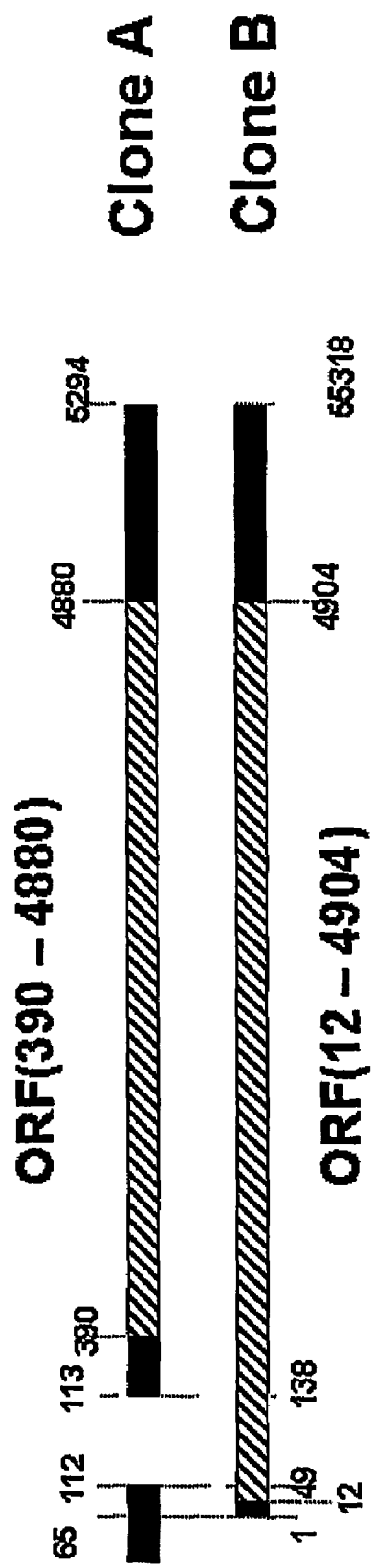
FIG. 1 shows the relative alignment positions of the two LFG1 clones.

The present invention is based in part on the identification of new gene families that are differentially expressed in cancerous human tissues compared to normal human tissues. These gene families correspond to the human cDNA of SEQ ID NOS: 1, 3, 5, 7, 9, 11, 13 and 15.

The genes and proteins of the invention may be used as diagnostic agents or markers to detect cancer or to differentiate carcinoma from normal tissue in a sample. They can also serve as a target for agents that modulate gene expression or activity. For example, agents may be identified that modulate biological processes associated with tumor growth, including the hyperplastic process of cancer.

II. Specific Embodiments

A. The Proteins Associated with Cancer

The present invention provides isolated proteins, allelic variants of the proteins, and conservative amino acid substitutions of the proteins. As used herein, the "protein" or "polypeptide" refers, in part, to a protein that has the human amino acid sequence depicted in SEQ ID NO: 2, 4, 6, 8, 10, 12, 14 or 16. The terms also refer to naturally occurring allelic variants and proteins that have a slightly different amino acid sequence than that specifically recited above. Allelic variants, though possessing a slightly different amino acid sequence than those recited above, will still have the same or similar biological functions associated with these proteins.

As used herein, the family of proteins related to the human amino acid sequence of SEQ ID NO: 2, 4, 6, 8, 10, 12, 14 or 16 refers to proteins that have been isolated from organisms in addition to humans. The methods used to identify and isolate other members of the family of proteins related to these proteins are described below.

The proteins of the present invention are preferably in isolated form. As used herein, a protein is said to be isolated when physical, mechanical or chemical methods are employed to remove the protein from cellular constituents that are normally associated with the protein. A skilled artisan can readily employ standard purification methods to obtain an isolated protein.

The proteins of the present invention further include insertion, deletion or conservative amino acid substitution variants of SEQ ID NO: 2, 4, 6, 8, 10, 12, 14 or 16. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein, in certain instances, may be altered without adversely affecting a biological activity. Accordingly, the amino acid sequence can be altered, for example to render the peptide more hydrophobic or hydrophilic, without adversely affecting the biological activities of the protein.

Ordinarily, the allelic variants, the conservative substitution variants, and the members of the protein family, will have an amino acid sequence having at least about 50%, 60%, 70% or 75% amino acid sequence identity with the sequence set forth in SEQ ID NO: 2, 4, 6, 8, 10, 12, 14 or 16, more preferably at least about 80%, even more preferably at least about 90-95%, and most preferably at least about 95-98% sequence identity. Identity or homology with respect to such sequences is defined herein as the percentage of amino acid residues in the candidate sequence that are identical with SEQ ID NO: 2, 4, 6, 8, 10, 12, 14 or 16, after aligning the sequences and introducing gaps, if necessary, to achieve the maximum percent homology, and not considering any conservative substitutions as part of the sequence identity (see section B for the relevant parameters). Fusion proteins, or N-terminal, C-terminal or internal extensions, deletions, or insertions into the peptide sequence shall not be construed as affecting homology.

Thus, the proteins of the present invention include molecules having the amino acid sequence disclosed in SEQ ID NO: 2, 4, 6, 8, 10, 12, 14 or 16; fragments thereof having a consecutive sequence of at least about 3, 4, 5, 6, 10, 15, 20, 25, 30, 35 or more amino acid residues of these proteins; amino acid sequence variants wherein one or more amino acid residues has been inserted N- or C-terminal to, or within, the disclosed coding sequence; and amino acid sequence variants of the disclosed sequence, or their fragments as defined above, that have been substituted by at least one residue. Such fragments, also referred to as peptides or polypeptides, may contain antigenic regions, functional regions of the protein identified as regions of the amino acid sequence which correspond to known protein domains, as well as regions of pronounced hydrophilicity. The regions are all easily identifiable by using commonly available protein sequence analysis software such as MacVector (Oxford Molecular).

Contemplated variants further include those containing predetermined mutations by, e.g., homologous recombination, site-directed or PCR mutagenesis, and the corresponding proteins of other animal species, including but not limited to rabbit, mouse, rat, porcine, bovine, ovine, equine and non-human primate species, and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope).

The present invention further provides compositions comprising a protein or polypeptide of the invention and a diluent. Suitable diluents can be aqueous or non-aqueous solvents or a combination thereof, and can comprise additional components, for example water-soluble salts or glycerol, that contribute to the stability, solubility, activity, and/or storage of the protein or polypeptide.

As described below, members of the families of proteins can be used: (1) to identify agents which modulate the level of or at least one activity of the protein, (2) to identify binding partners for the protein, (3) as an antigen to raise polyclonal or monoclonal antibodies, (4) as a therapeutic agent or target and (5) as a diagnostic agent or marker of cancer.

B. Nucleic Acid Molecules

The present invention further provides nucleic acid molecules that encode the protein having SEQ ID NO: 2, 4, 6, 8, 10, 12, 14 or 16 and the related proteins herein described, preferably in isolated form. As used herein, "nucleic acid" is defined as RNA or DNA that encodes a protein or peptide as defined above, is complementary to a nucleic acid sequence encoding such peptides, hybridizes to the nucleic acid of SEQ ID NO: 1, 3, 5, 7, 9, 11, 13 or 15 and remains stably bound to it under appropriate stringency conditions, encodes a polypeptide sharing at least about 50%, 60%, 70% or 75%, preferably at least about 80%, more preferably at least about 90-95%, and most preferably at least about 95-98% or more identity with the peptide sequence of SEQ ID NO: 2, 4, 6, 8, 10, 12, 14 or 16 or exhibits at least 50%, 60%, 70% or 75%, preferably at least about 80%, more preferably at least about 90-95%, and most preferably at least about 95-98% or more nucleotide sequence identity over the open reading frames of SEQ ID NO: 1, 3, 5, 7, 9, 11, 13 or 15.

The present invention further includes isolated nucleic acid molecules that specifically hybridize to the complement of SEQ ID NO: 1, 3, 5, 7, 9, 11, 13 or 15, particularly molecules that specifically hybridize over the open reading frames. Such molecules that specifically hybridize to the complement of SEQ ID NO: 1, 3, 5, 7, 9, 11, 13 or 15 typically do so under stringent hybridization conditions.

Specifically contemplated are genomic DNA, cDNA, mRNA and antisense molecules, as well as nucleic acids based on alternative backbones or including alternative bases, whether derived from natural sources or synthesized. Such hybridizing or complementary nucleic acids, however, are defined further as being novel and unobvious over any prior art nucleic acid including that which encodes, hybridizes under appropriate stringency conditions, or is complementary to nucleic acid encoding a protein according to the present invention.

Homology or identity at the nucleotide or amino acid sequence level is determined by BLAST (Basic Local Alignment Search Tool) analysis using the algorithm employed by the programs blastp, blastn, blastx, tblastn and tblastx (Altschul et al. (1997), *Nucleic Acids Res.* 25: 3389-3402, and Karlin et al. (1990), *Proc. Natl. Acad. Sci. USA* 87: 2264-2268, both fully incorporated by reference) which are tailored for sequence similarity searching. The approach used by the BLAST program is to first consider similar segments, with and without gaps, between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (1994), *Nat. Genet.* 6: 119-129 which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al. (1992), *Proc. Natl. Acad. Sci. USA* 89: 10915-10919, fully incorporated by reference), recommended for query sequences over 85 nucleotides or amino acids in length.

For blastn, the scoring matrix is set by the ratios of M (i.e., the reward score for a pair of matching residues) to N (i.e., the penalty score for mismatching residues), wherein the default values for M and N are 5 and -4, respectively. Four blastn parameters were adjusted as follows: Q=10 (gap creation penalty); R=10 (gap extension penalty); wink=1 (generates word hits at every $wink^{th}$ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

"Stringent conditions" are those that (1) employ low ionic strength and high temperature for washing, for example, 0.015 M NaCl/0.0015 M sodium citrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is hybridization in 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal. Preferred molecules are those that hybridize under the above conditions to the complement of SEQ ID NO: 1, 3, 5, 7, 9, 11, 13 or 15 and which encode a functional or full-length protein. Even more preferred hybridizing molecules are those that hybridize under the above conditions to the complement strand of the open reading frame of SEQ ID NO: 1, 3, 5, 7, 9, 11, 13 or 15.

As used herein, a nucleic acid molecule is said to be "isolated" when the nucleic acid molecule is substantially separated from contaminant nucleic acid molecules encoding other polypeptides.

The present invention further provides fragments of the disclosed nucleic acid molecules. As used herein, a fragment of a nucleic acid molecule refers to a small portion of the coding or non-coding sequence. The size of the fragment will be determined by the intended use. For example, if the fragment is chosen so as to encode an active portion of the protein, the fragment will need to be large enough to encode the functional region(s) of the protein. For instance, fragments which encode peptides corresponding to predicted antigenic regions may be prepared. If the fragment is to be used as a nucleic acid probe or PCR primer, then the fragment length is chosen so as to obtain a relatively small number of false positives during probing/priming (see the discussion in Section G).

Fragments of the nucleic acid molecules of the present invention (i.e., synthetic oligonucleotides) that are used as probes or specific primers for the polymerase chain reaction (PCR), or to synthesize gene sequences encoding proteins of the invention, can easily be synthesized by chemical techniques, for example, the phosphoramidite method of Matteucci et al., ((1981) *J. Am. Chem. Soc.* 103: 3185-3191) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled or fluorescently labeled nucleotides and the like. A skilled artisan can readily employ any such label to obtain labeled variants of the nucleic acid molecules of the invention.

C. Isolation of Other Related Nucleic Acid Molecules

As described above, the identification and characterization of the nucleic acid molecule having SEQ ID NO: 1, 3, 5, 7, 9, 11, 13 or 15 allows a skilled artisan to isolate nucleic acid molecules that encode other members of the protein family in addition to the sequences herein described. Further, the presently disclosed nucleic acid molecules allow a skilled artisan to isolate nucleic acid molecules that encode other members of the family of proteins in addition to the proteins having SEQ ID NO: 2, 4, 6, 8, 10, 12, 14 or 16.

For instance, a skilled artisan can readily use the amino acid sequence of SEQ ID NO: 2, 4, 6, 8, 10, 12, 14 or 16 to generate antibody probes to screen expression libraries prepared from appropriate cells. Typically, polyclonal antiserum from mammals such as rabbits immunized with the purified protein (as described below) or monoclonal antibodies can be used to probe a mammalian cDNA or genomic expression library, such as lambda gtll library, to obtain the appropriate coding sequence for other members of the protein family. The cloned cDNA sequence can be expressed as a fusion protein, expressed directly using its own control sequences, or expressed by constructions using control sequences appropriate to the particular host used for expression of the enzyme.

Alternatively, a portion of the coding sequence herein described can be synthesized and used as a probe to retrieve DNA encoding a member of the protein family from any mammalian organism. Oligomers containing approximately 18-20 nucleotides (encoding about a 6-7 amino acid stretch) are prepared and used to screen genomic DNA or cDNA libraries to obtain hybridization under stringent conditions or conditions of sufficient stringency to eliminate an undue level of false positives.

Additionally, pairs of oligonucleotide primers can be prepared for use in PCR to selectively clone an encoding nucleic acid molecule. A PCR denature/anneal/extend cycle for using such PCR primers is well known in the art and can readily be adapted for use in isolating other encoding nucleic acid molecules.

Nucleic acid molecules encoding other members of the protein family may also be identified in existing genomic or other sequence information using any available computational method, including but not limited to: PSI-BLAST (Altschul et al. (1997), *Nucl. Acids Res.* 25: 3389-3402); PHI-BLAST (Zhang et al. (1998), *Nucl. Acids Res.* 26: 3986-3990), 3D-PSSM (Kelly et al. (2000), *J. Mot. Biol.* 299: 499-520); and other computational analysis methods (Shi et al. (1999), *Biochem. Biophys. Res. Commun.* 262: 132-138 and Matsunami et. al. (2000), *Nature* 404: 601-604).

D. rDNA Molecules Containing a Nucleic Acid Molecule

The present invention further provides recombinant DNA molecules (rDNAs) that contain a coding sequence. As used herein, a rDNA molecule is a DNA molecule that has been subjected to molecular manipulation in situ. Methods for generating rDNA molecules are well known in the art, for example, see Sambrook et al., *Molecular Cloning—A Laboratory Manual. Third Ed.*, Cold Spring Harbor Laboratory Press, Cold Spring Harbor, N.Y., 2001. In the preferred rDNA molecules, a coding DNA sequence is operably linked to expression control sequences and/or vector sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin, kanamycin, chloramphenicol or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from BioRad Laboratories, (Richmond, Calif.), pPL and pKK223 available from Pharmacia (Piscataway, N.J.).

Expression vectors compatible with eukaryotic cells, preferably those compatible with vertebrate cells, can also be used to form rDNA molecules that contain a coding sequence. Eukaryotic cell expression vectors, including viral vectors, are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), the vector pCDM8 described herein, and the like eukaryotic expression vectors. Vectors may be modified to include tissue specific promoters if needed.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al. (1982), *J. Mol. Anal. Genet.* 1:327-341). Alternatively, the selectable marker can be present on a separate plasmid, and the two vectors are introduced by co-transfection of the host cell, and selected by culturing in the appropriate drug for the selectable marker.

E. Host Cells Containing an Exogenously Supplied Coding Nucleic Acid Molecule

The present invention further provides host cells transformed with a nucleic acid molecule that encodes a protein of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells available from the ATCC as CCL61, NIH Swiss mouse embryo cells (NIH/3T3) available from the ATCC as CRL 1658, baby hamster kidney cells (BHK), and the like eukaryotic tissue culture cell lines.

Any prokaryotic host can be used to express a rDNA molecule encoding a protein of the invention. The preferred prokaryotic host is *E. coli*.

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed (see, for example, Cohen et at. (1972), *Proc. Natl. Acad. Sci. USA* 69: 2110; and Sambrook et al., supra). With regard to transformation of vertebrate cells with vectors containing rDNAs, electroporation, cationic lipid or salt treatment methods are typically employed, see, for example, Graham et al (1973), *Virol.* 52: 456; Wigler et al. (1979), *Proc. Natl. Acad. Sci. USA* 76:1373-1376.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, (1975) *J. Mol. Biol.* 98: 503 or Berent et al., (1985) *Biotech.* 3: 208, or the proteins produced from the cell assayed via an immunological method.

F. Production of Recombinant Proteins Using a rDNA Molecule

The present invention further provides methods for producing a protein of the invention using nucleic acid molecules herein described. In general terms, the production of a recombinant form of a protein typically involves the following steps:

First, a nucleic acid molecule is obtained that encodes a protein of the invention, such as a nucleic acid molecule comprising, consisting essentially of or consisting of SEQ ID NO: 1, 3, 5, 7, 9, 11, 13 or 15, or nucleotides 390-4883 or 390-4880 of SEQ ID NO: 1, or nucleotides 124907 or 124904 of SEQ ID NO: 3, or nucleotides 424-1911 or 424-1908 of SEQ ID NO: 5, or nucleotides 405-1838 or 405-1835 of SEQ ID NO: 7, or nucleotides 89-1153 or 89-1150 of SEQ ID NO: 9, or nucleotides 223-1572 or 223-1569 of SEQ ID NO: 11, or 418-1395 or 418-1392 of SEQ ID NO: 13, or nucleotides 271-1434 or 271-1431 of SEQ ID NO: 15. If the encoding sequence is uninterrupted by introns, as are these open-reading-frames, it is directly suitable for expression in any host.

The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

G. Methods to Identify Agents that Modulate the Expression of a Nucleic Acid Encoding the Genes Associated with Cancer Another embodiment of the present invention provides methods for identifying agents that modulate the expression of a nucleic acid encoding a protein of the invention such as a protein having the amino acid sequence of SEQ ID NO: 2, 4, 6, 8, 10, 12, 14 or 16. Such assays may utilize any available means of monitoring for changes in the expression level of the nucleic acids of the invention. As used herein, an agent is said to modulate the expression of a nucleic acid of the invention if it is capable of up- or down-regulating expression of the nucleic acid in a cell.

In one assay format, cell lines that contain reporter gene fusions between nucleotides from within the open reading frame defined by nucleotides 390-4883 of SEQ ID NO: 1, nucleotides 12-4907 of SEQ ID NO: 3, nucleotides 424-1911 of SEQ ID NO: 5, nucleotides 405-1838 of SEQ ID NO: 7, nucleotides 89-1153 of SEQ ID NO: 9, nucleotides 223-1572 of SEQ ID NO: 11, nucleotides 418-1395 of SEQ ID NO: 13, nucleotides 271-1434 of SEQ ID NO: 15, and/or the 5' and/or 3' regulatory elements and any assayable fusion partner may be prepared. Numerous assayable fusion partners are known and readily available including the firefly luciferase gene and the gene encoding chloramphenicol acetyltransferase (Alam et al. (1990), *Anal. Biochem.* 188: 245-254). Cell lines containing the reporter gene fusions are then exposed to the agent to be tested under appropriate conditions and time. Differential expression of the reporter gene between samples exposed to the agent and control samples identifies agents which modulate the expression of a nucleic acid of the invention.

Additional assay formats may be used to monitor the ability of the agent to modulate the expression of a nucleic acid encoding a protein of the invention, such as the protein having SEQ ID NO: 2, 4, 6, 8, 10, 12, 14 or 16. For instance, mRNA expression may be monitored directly by hybridization to the nucleic acids of the invention. Cell lines are exposed to the agent to be tested under appropriate conditions and time and total RNA or mRNA is isolated by standard procedures such those disclosed in Sambrook et al., *Molecular Cloning—A Laboratory Manual. Third Ed.*, Cold Spring Harbor Laboratory Press, Cold Spring Harbor, N.Y., 2001.

The preferred cells will be those derived from human tissue, for instance, biopsy tissue or cultured cells from patients with cancer. Cell lines such as ATCC breast ductal carcinoma cell lines (Catalogue Nos. CRL-2320, CRL-2338, and CRL-7345), ATCC colorectal adenocarcinoma cell lines (Catalogue Nos. CCL-222, CCL-224, CCL-225, CCL-234, CRL- 7159, and CRL-7184), ATCC kidney clear cell carcinoma cell lines (Catalogue Nos. HTB-46 and HTB-47), ATCC renal cell adenocarcinoma cell lines (Catalogue Nos. CRL-1611, CRL-1932 and CRL-1933), ATCC liver hepatocellular carcinoma cell lines (Catalogue Nos. CRL-2233, CRL-2234, and HB-8065), ATCC lung adenocarcinoma cell lines (Catalogue Nos. CRL-5944, CRL-7380, and CRL-5907), ATCC lymphoma cell lines (Catalogue Nos. CRL-7936, CRL-7264, and CRL-7507), ATCC ovary adenocarcinoma cell lines (Catalogue Nos. HTB-161, HTB-75, and HTB-76), ATCC pancreas adenocarcinoma cell lines (Catalogue Nos. CRL-1687, CRL-2119, and HTP-79), prostate adenocarinoma cell lines (Catalogue Nos. CRL-1435, CRL-2422, and CRL-2220), and ATCC gastric adenocarcinoma cell lines (Catalogue Nos. CRL-1739, CRL-1863, and CRL-1864) may be used. Alternatively, other available cells or cell lines may be used.

Probes to detect differences in RNA expression levels between cells exposed to the agent and control cells may be prepared from the nucleic acids of the invention. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and probe:non-target hybrids.

Probes may be designed from the nucleic acids of the invention through methods known in the art. For instance, the G+C content of the probe and the probe length can affect probe binding to its target sequence. Methods to optimize probe specificity are commonly available in Sambrook et al., supra, or Ausubel et al., *Short Protocols in Molecular Biology, Fourth Ed.*, John Wiley & Sons, Inc., New York, 1999.

Hybridization conditions are modified using known methods, such as those described by Sambrook et al. and Ausubel et al. as required for each probe. Hybridization of total cellular RNA or RNA enriched for polyA RNA can be accomplished in any available format. For instance, total cellular RNA or RNA enriched for polyA RNA can be affixed to a solid support and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a silicon chip, porous glass wafer or membrane. The solid support can then be exposed to total cellular RNA or polyA RNA from a sample under conditions in which the affixed sequences will specifically hybridize. Such solid supports and hybridization methods are widely available, for example, those disclosed by Beattie, (1995) WO 95/11755. By examining for the ability of a given probe to specifically hybridize to an RNA sample from an untreated cell population and from a cell population exposed to the agent, agents which up- or down-regulate the expression of a nucleic acid encoding the protein having the sequence of SEQ ID NO: 2, 4, 6, 8, 10, 12, 14 or 16 are identified.

Hybridization for qualitative and quantitative analysis of mRNAs may also be carried out by using a RNase Protection Assay (i.e., RPA, see Ma et al. (1996), *Methods* 10: 273-238). Briefly, an expression vehicle comprising cDNA encoding the gene product and a phage specific DNA dependent RNA polymerase promoter (e.g., T7, T3 or SP6 RNA polymerase) is linearized at the 3' end of the cDNA molecule, downstream from the phage promoter, wherein such a linearized molecule is subsequently used as a template for synthesis of a labeled antisense transcript of the cDNA by in vitro transcription. The labeled transcript is then hybridized to a mixture of isolated RNA (i.e., total or fractionated mRNA) by incubation at 45° C. overnight in a buffer comprising 80% formamide, 40 mM Pipes, pH 6.4, 0.4 M NaCl and 1 mM EDTA. The resulting hybrids are then digested in a buffer comprising 40 µg/ml ribonuclease A and 2 µg/ml ribonuclease. After deactivation and extraction of extraneous proteins, the samples are loaded onto urea/polyacrylamide gels for analysis.

In another assay, to identify agents which affect the expression of the instant gene products, cells or cell lines are first identified which express the gene products of the invention physiologically. Cells and/or cell lines so identified would be expected to comprise the necessary cellular machinery such that the fidelity of modulation of the transcriptional apparatus is maintained with regard to exogenous contact of agent with appropriate surface transduction mechanisms and/or the cytosolic cascades. Further, such cells or cell lines would be transduced or transfected with an expression vehicle (e.g., a plasmid or viral vector) construct comprising an operable non-translated 5' promoter-containing end of the structural gene encoding the instant gene products fused to one or more antigenic fragments, which are peculiar to the instant gene products, wherein said fragments are under the transcriptional control of said promoter and are expressed as polypeptides whose molecular weight can be distinguished from the naturally occurring polypeptides or may further comprise an immunologically distinct tag or other detectable marker. Such a process is well known in the art (see Sambrook et al., supra).

Cells or cell lines transduced or transfected as outlined above are then contacted with agents under appropriate conditions. For example, the agent in a pharmaceutically acceptable excipient is contacted with cells in an aqueous physiological buffer such as phosphate buffered saline (PBS) at physiological pH, Eagles balanced salt solution (BSS) at physiological pH, PBS or BSS comprising serum or conditioned media comprising PBS or BSS and/or serum incubated at 37° C. Said conditions may be modulated as deemed necessary by one of skill in the art. Subsequent to contacting the cells with the agent, said cells will be disrupted and the polypeptides of the lysate are fractionated such that a polypeptide fraction is pooled and contacted with an antibody to be further processed by immunological assay (e.g., ELISA, immunoprecipitation or Western blot). The pool of proteins isolated from the "agent-contacted" sample will be compared with a control sample where only the excipient is contacted with the cells and an increase or decrease in the immunologically generated signal from the "agent-contacted" sample compared to the control will be used to distinguish the effectiveness of the agent.

H. Methods to Identify Agents that Modulate the Level or at Least One Activity of the Cancer Associated Proteins Another embodiment of the present invention provides methods for identifying agents that modulate the level or at least one activity of a protein of the invention such as the protein having the amino acid sequence of SEQ ID NO: 2, 4, 6, 8, 10, 12, 14 or 16. Such methods or assays may utilize any means of monitoring or detecting the desired activity and are particularly useful for identifying agents that treat cancer.

In one format, the relative amounts of a protein of the invention between a cell population that has been exposed to the agent to be tested compared to an un-exposed control cell population may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe.

Antibody probes are prepared by immunizing suitable mammalian hosts in appropriate immunization protocols using the peptides, polypeptides or proteins of the invention if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co. (Rockford, Ill.), may be desirable to provide accessibility to the hapten. The hapten peptides can be extended at either the amino or carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein ((1975) *Nature* 256: 495-497) or modifications which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonal antibodies or the polyclonal antisera which contain the immunologically significant (antigen-binding) portion can be used as antagonists, as well as the intact antibodies. Use of immunologically reactive (antigen-binding) antibody fragments, such as the Fab, Fab', or F(ab')$_2$ fragments is often preferable, especially in a therapeutic context, as these fragments are generally less immunogenic than the whole immunoglobulin.

The antibodies or antigen-binding fragments may also be produced, using current technology, by recombinant means. Antibody regions that bind specifically to the desired regions of the protein can also be produced in the context of chimeras with multiple species origin, such as humanized antibodies.

Agents that are assayed in the above method can be randomly selected or rationally selected or designed. As used herein, an agent is said to be randomly selected when the agent is chosen randomly without considering the specific sequences involved in the association of a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action.

Agents can be rationally selected or rationally designed by utilizing the peptide sequences that make up these sites. For example, a rationally selected peptide agent can be a peptide whose amino acid sequence is identical to or a derivative of any functional consensus site.

The agents of the present invention can be, as examples, peptides, small molecules, vitamin derivatives, as well as carbohydrates. Dominant negative proteins, DNAs encoding these proteins, antibodies to these proteins, peptide fragments of these proteins or mimics of these proteins may be introduced into cells to affect function. "Mimic" used herein refers to the modification of a region or several regions of a peptide molecule to provide a structure chemically different from the parent peptide but topographically and functionally similar to the parent peptide (see Grant in: *Molecular Biology and Biotechnology*, Meyers, ed., pp. 659-664, VCH Publishers, Inc., New York, 1995). A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of proteins of the invention, e.g., cytoplasmic domain, spacer domain, α-helical coiled-coil domain, or the receptor domain, as described herein. Antibody agents are obtained by immunization of suitable mammalian subjects with peptides, containing as antigenic regions, those portions of the protein intended to be targeted by the antibodies.

I. Uses for Agents that Modulate the Expression or at Least one Activity of the Proteins Associated with Cancer As provided in the Examples, the proteins and nucleic acids of the invention, such as the proteins having the amino acid sequence of SEQ ID NO: 2, 4, 6, 8, 10, 12, 14 or 16, are differentially expressed in cancerous tissue. Agents that up- or down-regulate or modulate the expression of the protein or at least one activity of the protein, such as agonists or antagonists, may be used to modulate biological and pathologic processes associated with the protein's function and activity. This includes agents identified employing homologues and analogues of the present invention.

As used herein, a subject can be any mammal, so long as the mammal is in need of modulation of a pathological or biological process mediated by a protein of the invention. The term "mammal" is defined as an individual belonging to the class Mammalia. The invention is particularly useful in the treatment of human subjects.

Pathological processes refer to a category of biological processes which produce a deleterious effect. For example, expression of a protein of the invention may be associated with cell growth or hyperplasia. As used herein, an agent is said to modulate a pathological process when the agent reduces the degree or severity of the process. For instance, cancer may be prevented or disease progression modulated by the administration of agents which up- or down-regulate or modulate in some way the expression or at least one activity of a protein of the invention.

The agents of the present invention can be provided alone, or in combination with other agents that modulate a particular pathological process. For example, an agent of the present invention can be administered in combination with other known drugs. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents which modulate expression or at least one activity of a protein of the invention. While individual needs vary, determination of optimal ranges of effective amounts of each component is within the skill of the art. Typical dosages comprise 0.1 to 100 µg/kg body wt. The preferred dosages comprise 0.1 to 10 µg/kg body wt. The most preferred dosages comprise 0.1 to 1 µg/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice. The compounds of this invention can be utilized in vivo, ordinarily in mammals, such as humans, sheep, horses, cattle, pigs, dogs, cats, rats and mice, or in vitro.

J. Methods to Identify Binding Partners

Another embodiment of the present invention provides methods for isolating and identifying binding partners of proteins of the invention. In general, a protein of the invention is mixed with a potential binding partner or an extract or fraction of a cell under conditions that allow the association of potential binding partners with the protein of the invention. After mixing, peptides, polypeptides, proteins or other molecules that have become associated with a protein of the invention are separated from the mixture. The binding partner that bound to the protein of the invention can then be removed and further analyzed. To identify and isolate a binding partner, the entire protein, for instance a protein comprising the entire amino acid sequence of SEQ ID NO: 2, 4, 6, 8, 10, 12, 14 or 16 can be used. Alternatively, a fragment of the protein can be used.

As used herein, a cellular extract refers to a preparation or fraction which is made from a lysed or disrupted cell. The preferred source of cellular extracts will be cells derived from human tumors or transformed cells, for instance, biopsy tissue or tissue culture cells from carcinomas. Alternatively, cellular extracts may be prepared from normal tissue or available cell lines.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the protein of the invention under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density/sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the protein of the invention can be immobilized on a solid support. For example, the protein can be attached to a nitrocellulose matrix or acrylic beads. Attachment of the protein to a solid support aids in separating peptide/binding partner pairs from other constituents found in the extract. The identified binding partners can be either a single protein or a complex made up of two or more proteins. Alternatively, binding partners may be identified using a Far-Western assay according to the procedures of Takayama et al. (1997), *Methods Mol. Biol.* 69: 171-184 or Sauder et al. (1996), *J. Gen. Virol.* 77: 991-996 or identified through the use of epitope tagged proteins or GST fusion proteins.

Alternatively, the nucleic acid molecules of the invention can be used in a yeast two-hybrid system or other in vivo protein-protein detection system. The yeast two-hybrid system has been used to identify other protein partner pairs and can readily be adapted to employ the nucleic acid molecules herein described.

K. Use of the Binding Partners of the Cancer Associated Proteins

Once isolated, the binding partners of the proteins of the invention, and homologues and analogues thereof, obtained using the above described methods can be used for a variety of purposes. The binding partners can be used to generate antibodies that bind to the binding partner using techniques known in the art. Antibodies that bind the binding partner can be used to assay the activity of the protein of the invention, as a therapeutic agent to modulate a biological or pathological process mediated by the protein of the invention, or to purify the binding partner. These uses are described in detail below.

L. Methods to Identify Agents that Block the Associations between the Binding Partners and the Cancer Associated Proteins Another embodiment of the present invention provides methods for identifying agents that reduce or block the association of a protein of the invention with a binding partner. Specifically, a protein of the invention is mixed with a binding partner in the presence and absence of an agent to be tested. After mixing under conditions that allow association of the proteins, the two mixtures are analyzed and compared to determine if the agent reduced or blocked the association of the protein of the invention with the binding partner. Agents that block or reduce the association of the protein of the invention with the binding partner will be identified as decreasing the amount of association present in the sample containing the tested agent.

As used herein, an agent is said to reduce or block the association between a protein of the invention and a binding partner when the presence of the agent decreases the extent to which or prevents the binding partner from becoming associated with the protein of the invention. One class of agents will reduce or block the association by binding to the binding partner while another class of agents will reduce or block the association by binding to the protein of the invention.

The binding partner used in the above assay can either be an isolated and fully characterized protein or can be a partially characterized protein that binds to the protein of the invention or a binding partner that has been identified as being present in a cellular extract. It will be apparent to one of ordinary skill in the art that so long as the binding partner has been characterized by an identifiable property, e.g., molecular weight, the present assay can be used.

Agents that are assayed in the above method can be randomly selected or rationally selected or designed. As used herein, an agent is said to be randomly selected when the agent is chosen randomly without considering the specific sequences involved in the association of the protein of the invention with the binding partner. An example of randomly selected agents is the use of a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. Agents can be rationally selected or rationally designed by utilizing the peptide sequences that make up the contact sites of the binding partner with the protein of the invention. For example, a rationally selected peptide agent can be a peptide whose amino acid sequence is identical to the contact site of the protein of the invention on the binding partner. Such an agent will reduce or block the association of the protein of the invention with the binding partner by binding to the binding partner.

The agents of the present invention can be, as examples, peptides, small molecules, vitamin derivatives, as well as carbohydrates. A skilled artisan can readily recognize that there is no limit as to the structural nature of the agents of the present invention.

One class of agents of the present invention are peptide agents whose amino acid sequences are chosen based on the amino acid sequence of the protein of the invention. The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene encoded amino acids are to be included.

Another class of agents of the present invention are antibodies immunoreactive with critical positions of the protein of the invention or the binding partner. As described above, antibodies are obtained by immunization of suitable mammalian subjects with peptides, containing as antigenic regions, those portions of the protein of the invention or the binding partner, intended to be targeted by the antibodies. Critical regions include the contact sites involved in the association of the protein of the invention with the binding partner.

As discussed below, the important minimal sequence of residues involved in activity of the protein of the invention define a functional linear domain that can be effectively used as a bait for two hybrid screening and identification of potential associated molecules. Use of such fragments will significantly increase the specificity of the screening as opposed to using the full-length molecule and is therefore preferred. Similarly, this linear sequence can be also used as an affinity matrix also to isolate binding proteins using a biochemical affinity purification strategy.

M. Uses for Agents that Block the Associations between the Binding Partners and the Cancer Associated Proteins As provided in the Examples, the proteins and nucleic acids of the invention, such as the proteins having the amino acid sequence of SEQ ID NO: 2, 4, 6, 8, 10, 12, 14 or 16, are differentially expressed in cancerous tissue. Agents that reduce or block the interactions of a protein of the invention, including those identified employing homologues and analogues of the protein, with a binding partner may be used to modulate biological and pathologic processes associated with the protein's function and activity.

As used herein, a subject can be any mammal, so long as the mammal is in need of modulation of a pathological or biological process mediated by a protein of the invention. The term "mammal" is meant an individual belonging to the class Mammalia. The invention is particularly useful in the treatment of human subjects.

Pathological processes refer to a category of biological processes which produce a deleterious effect. For example, expression of a protein of the invention may be associated with cell growth or hyperplasia. As used herein, an agent is said to modulate a pathological process when the agent reduces the degree or severity of the process. For instance, cancer may be prevented or disease progression modulated by the administration of agents that reduce or block the interactions of a protein of the invention with a binding partner.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents that block association of a protein of the invention with a binding partner. While individual needs vary, determination of optimal ranges of effective amounts of each component is within the skill of the art. Typical dosages comprise 0.1 to 100 µg/kg body wt. The preferred dosages comprise 0.1 to 10 µg/kg body wt. The most preferred dosages comprise 0.1 to 1 µg/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water soluble form, for example, water soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice. The compounds of this invention can be utilized in vivo, ordinarily in mammals, such as humans, sheep, horses, cattle, pigs, dogs, cats, rats and mice, or in vitro.

N. Rational Drug Design and Combinatorial Chemistry

The present invention further encompasses rational drug design and combinatorial chemistry. Those of skill will recognize appropriate methods to utilize and exploit aspects of the present invention in identifying compounds which can be developed for cancer treatment. Rational drug design involving polypeptides requires identifying and defining a first peptide with which the designed drug is to interact, and using the first target peptide to define the requirements for a second peptide. With such requirements defined, one can find or prepare an appropriate peptide or non-peptide that meets all or substantially all of the defined requirements. Thus, one goal of rational drug design is to produce structural or functional analogs of biologically active polypeptides of interest or of small molecules with which they interact (e.g., agonists, antagonists, null compounds) in order to fashion drugs that are, for example, more or less potent forms of the ligand. (See, e.g., Hodgson (1991), *Bio. Technology* 9:19-21). Combinatorial chemistry is the science of synthesizing and testing compounds for bioactivity en masse, instead of one by one, the aim being to discover drugs and materials more quickly and inexpensively than was formerly possible. Rational drug design and combinatorial chemistry have become more intimately related in recent years due to the development of approaches in computer-aided protein modeling and drug discovery. (See e.g., U.S. Pat. Nos. 4,908,773; 5,884,230; 5,873,052; 5,331,573; and 5,888,738).

The use of molecular modeling as a tool for rational drug design and combinatorial chemistry has dramatically increased due to the advent of computer graphics. Not only is it possible to view molecules on computer screens in three dimensions but it is also possible to examine the interactions of macromolecules such as enzymes and receptors and rationally designed derivative molecules to test. (See Boorman (1992), *Chem. Eng. News* 70:18-26). A vast amount of user-friendly software and hardware is now available and virtually all pharmaceutical companies have computer modeling groups devoted to rational drug design. Molecular Simulations Inc. (www.msi.com), for example, sells several sophisticated programs that allow a user to start from an amino acid sequence, build a two or three-dimensional model of the protein or polypeptide, compare it to other two and three-dimensional models, and analyze the interactions of compounds, drugs, and peptides with a three dimensional model in real time. Accordingly, in some embodiments of the invention, software is used to compare regions of the invention protein and molecules that interact therewith (collectively referred to as "binding partners"—e.g., anti-protein antibodies), and fragments or derivatives of these molecules with other molecules, such as peptides, peptidomimetics, and chemicals, so that therapeutic interactions can be predicted and designed. (See Schneider (1998), *Genetic Engineering News* December: page 20; Tempczyk et al. (1997), Molecular Simulations Inc. Solutions April; and Butenhof (1998), Molecular Simulations Inc. Case Notes (August 1998) for a discussion of molecular modeling).

O. Gene Therapy

In another embodiment, genetic therapy can be used as a means for modulating biological and pathologic processes associated with the protein's function and activity. This comprises inserting into a cancerous cell a gene construct encoding a protein comprising all or at least a portion of the sequences of SEQ ID NO: 2, 4, 6, 8, 10, 12, 14 or 16, or alternatively a gene construct comprising all or a portion of the non-coding region of SEQ ID NO: 1, 3, 5, 7, 9, 11, 13 or 15, operably linked to a promoter or enhancer element such that expression of said protein causes suppression of said cancer and wherein said promoter or enhancer element is a promoter or enhancer element modulating said gene construct.

In the constructs described, expression of said protein can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in neural cells, T cells, or B cells may be used to direct the expression. The enhancers used could include, without limitation, those that are characterized as tissue or cell specific in their expression. Alternatively, if a genomic clone of LFG1, LFG2, LFG3, LFG4, LFG5 or LFG6 is used as a therapeutic construct (for example, following its isolation by hybridization with the nucleic acid molecule of the invention described above), regulation may be mediated by the cognate regulatory sequences or, if desired, by regulatory sequences derived from a heterologous source, including any of the promoters or regulatory elements described above.

Insertion of the construct into a cancerous cell is accomplished in vivo, for example using a viral or plasmid vector. Such methods can also be applied to in vitro uses. Thus, the methods of the present invention are readily applicable to different forms of gene therapy, either where cells are genetically modified ex vivo and then administered to a host or where the gene modification is conducted in vivo using any of a number of suitable methods involving vectors especially suitable to such therapies.

Retroviral vectors, adenoviral vectors, adeno-associated viral vectors, or other viral vectors with the appropriate tropism for cells likely to be involved in cancer (for example, epithelial cells) may be used as a gene transfer delivery system for a therapeutic gene construct. Numerous vectors useful for this purpose are generally known (Cozzi P J, et al., (2002) *Prostate*, 53(2):95-100; Bitzer M, Lauer U., (2002) *Dtsch Med Wochenschr.* 127(31-32):1623-1624; Mezzina and Danos (2002), *Trends Genet.* 8:241-256; Loser et al. (2002) *Curr. Gene Ther.* 2:161-171; Pfeifer and Verma (2001), *Annu. Rev. Genomics Hum. Genet.* 2:177-211). Retroviral vectors are particularly well developed and have been used in clinical settings (Anderson et al. (1995), U.S. Pat. No. 5,399,346). Non-viral approaches may also be employed for the introduction of therapeutic DNA into cells otherwise predicted to undergo cancer (Jeschke et al. (20002) *Curr. Gene Ther.* 1:267-278; Wu et al. (1988), *J. Biol. Chem.* 263:14621-14624; Wu et al. (1989), *J. Biol. Chem.* 264:16985-16987). For example, a gene may be introduced into a neuron or a T cell by lipofection, asialorosonucoid polylysine conjugation, or, less preferably, microinjection under surgical conditions.

For any of the methods of application described above, the therapeutic nucleic acid construct is preferably applied to the site of the cancer event (for example, by injection). However, it may also be applied to tissue in the vicinity of the cancer event or to a blood vessel supplying the cells predicted to undergo cancer.

P. Transgenic Animals

Transgenic animals containing mutant, knock-out or modified genes corresponding to the cDNA sequence of SEQ ID NO: 1, 3, 5, 7, 9, 11, 13 or 15, or the open reading frame encoding the polypeptide sequence of SEQ ID NO: 2, 4, 6, 8, 10, 12, 14 or 16, or fragments thereof having a consecutive sequence of at least about 3, 4, 5, 6, 10, 15, 20, 25, 30, 35 or more amino acid residues, are also included in the invention. Transgenic animals are genetically modified animals into which recombinant, exogenous or cloned genetic material has been experimentally transferred. Such genetic material is often referred to as a "transgene." The nucleic acid sequence of the transgene, in this case a form of SEQ ID NO: 1, 3, 5, 7, 9, 11, 13 or 15, may be integrated either at a locus of a genome where that particular nucleic acid sequence is not otherwise normally found or at the normal locus for the transgene. The transgene may consist of nucleic acid sequences derived from the genome of the same species or of a different species than the species of the target animal.

In some embodiments, transgenic animals in which all or a portion of a gene comprising SEQ ID NO: 1, 3, 5, 7, 9, 11, 13 or 15 is deleted may be constructed. In those cases where the gene corresponding to SEQ ID NO: 1, 3, 5, 7, 9, 11, 13 or 15 contains one or more introns, the entire gene—all exons, introns and the regulatory sequences—may be deleted. Alternatively, less than the entire gene may be deleted. For example, a single exon and/or intron may be deleted, so as to create an animal expressing a modified version of a protein of the invention.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they too are transgenic animals.

The alteration or genetic information may be foreign to the species of animal to which the recipient belongs, foreign only to the particular individual recipient, or may be genetic information already possessed by the recipient. In the last case, the altered or introduced gene may be expressed differently than the native gene.

Transgenic animals can be produced by a variety of different methods including transfection, electroporation, microinjection, gene targeting in embryonic stem cells and recombinant viral and retroviral infection (see, e.g., U.S. Pat. No. 4,736,866; U.S. Pat. No. 5,602,307; Mullins et al. (1993), *Hypertension* 22: 630-633; Brenin et al. (1997), *Surg. Oncol.* 6: 99-110; *Recombinant Gene Expression Protocols (Methods in Molecular Biology. Vol. 62)*. Tuan, ed., Humana Press, Totowa, N.J., 1997).

A number of recombinant or transgenic mice have been produced, including those which express an activated oncogene sequence (U.S. Pat. No. 4,736,866); express simian SV40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720, 936); have a reduced capacity to mediate cellular adhesion (U.S. Pat. No. 5,602,307); possess a bovine growth hormone gene (Clutter et al. (1996), *Genetics* 143: 1753-1760); or, are capable of generating a fully human antibody response (McCarthy (1997), *Lancet* 349: 405).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al. (1997), *Mol. Reprod. Dev.* 46: 515-526; Houdebine (1995), *Reprod. Nutr. Dev.* 35: 609-617; Petters (1994), *Reprod. Fertil. Dev.* 6: 643-645; Schnieke et al. (1997), *Science* 278: 2130-2133; and Amoah (1997), *J Animal Sci.* 75: 578-585).

The method of introduction of nucleic acid fragments into recombination competent mammalian cells can be by any method which favors co-transformation of multiple nucleic acid molecules. Detailed procedures for producing transgenic animals are readily available to one skilled in the art, including the disclosures in U.S. Pat. No. 5,489,743 and U.S. Pat. No. 5,602,307.

Q. Diagnostic Methods

As the genes and proteins of the invention are differentially expressed in cancerous tissues compared to non-cancerous tissues, the genes and proteins of the invention may be used to diagnose or monitor cancer, to track disease progression, or to differentiate cancerous tissue from non-cancerous tissue samples. One means of diagnosing cancer using the nucleic acid molecules or proteins of the invention involves obtaining tissue from living subjects.

Assays to detect nucleic acid or protein molecules of the invention may be in any available format. Typical assays for nucleic acid molecules include hybridization or PCR based formats. Typical assays for the detection of proteins, polypeptides or peptides of the invention include the use of antibody probes in any available format such as in situ binding assays, etc. (see Harlow & Lane, *Antibodies—A Laboratory Manual*, Cold Spring Harbor Laboratory Press, Cold Spring Harbor, N.Y., 1988). In preferred embodiments, assays are carried-out with appropriate controls.

Generally, the diagnostics of the invention can be classified according to whether the embodiment is a nucleic acid or protein-based assay. Some diagnostic assays detect mutations or polymorphisms in the invention nucleic acids or proteins, which contribute to cancerous aberrations. Other diagnostic assays identify and distinguish defects in protein activity by detecting a level of invention RNA or protein in a tested organism that resembles the level of invention RNA or protein in a organism suffering from a disease, such as cancer, or by detecting a level of RNA or protein in a tested organism that is different than an organism not suffering from a disease.

Additionally, the manufacture of kits that incorporate the reagents and methods described in the following embodiments so as to allow for the rapid detection and identification of aberrations in protein activity or level are contemplated. The diagnostic kits can include a nucleic acid probe or an antibody or combinations thereof, which specifically detect a mutant form of the invention protein or a nucleic acid probe or an antibody or combinations thereof, which can be used to determine the level of RNA or protein expression of one or more invention protein. The detection component of these kits will typically be supplied in combination with one or more of the following reagents. A support capable of absorbing or otherwise binding DNA, RNA, or protein will often be supplied. Available supports include membranes of nitrocellulose, nylon or derivatized nylon that can be characterized by bearing an array of positively charged substituents. One or more restriction enzymes, control reagents, buffers, amplification enzymes, and non-human polynucleotides like calf-thymus or salmon-sperm DNA can be supplied in these kits.

Useful nucleic acid-based diagnostic techniques include, but are not limited to, direct DNA sequencing, gradient gel electrophoresis, Southern Blot analysis, single-stranded confirmation analysis (SSCA), RNAse protection assay, dot blot analysis, nucleic acid amplification, allele-specific PCR and combinations of these approaches. The starting point for these analyses is isolated or purified nucleic acid from a biological sample. It is contemplated that tissue biopsies would provide a good sample source. The nucleic acid is extracted from the sample and can be amplified by a DNA amplification technique such as the Polymerase Chain Reaction (PCR) using primers. Those of skill in the art will readily recognize methods available for confirming the presence of polymorphisms. In addition, any addressable array technology known in the art can be employed with this aspect of the invention. One particular embodiment of polynucleotide arrays is known as Genechips™, and has been generally described in U.S. Pat. No. 5,143,854; PCT publications WO 90/15070 and 92/10092.

A wide variety of labels and conjugation techniques are known by those skilled in the art and can be used in various nucleic acid assays. There are several ways to produce labeled nucleic acids for hybridization or PCR including, but not limited to, oligolabeling, nick translation, end-labeling, or PCR amplification using a labeled nucleotide. Alternatively, a nucleic acid encoding an invention protein can be cloned into a vector for the production of an mRNA probe. Such vectors are known in the art, are commercially available, and can be used to synthesize RNA probes in vitro by addition of an appropriate RNA polymerase such as T7, T3 or SP6 and labeled nucleotides. A number of companies such as Pharmacia Biotech (Piscataway, N.J.), Promega (Madison, Wis.), and U.S. Biochemical Corp (Cleveland, Ohio) supply commercial kits and protocols for these procedures. Suitable reporter molecules or labels include those radionuclides, enzymes, fluorescent, chemiluminescent, or chromogenic agents, as well as, substrates, cofactors, inhibitors, magnetic particles and the like.

In preferred protein-based diagnostic, antibodies of the invention are attached to a support in an ordered array wherein a plurality of antibodies are attached to distinct regions of the support that do not overlap with each other. Those of skill in the art will readily recognize available assays that are protein-based diagnostics. Proteins are obtained from biological samples and are labeled by conventional approaches (e.g., radioactivity, colorimetrically, or fluorescently). Employing labeled standards of a known concentration of mutant and/or wild-type invention protein, an investigator can accurately determine the concentration of the invention protein in a sample and from this information can assess the expression level of the particular form of the protein. Conventional methods in densitometry can also be used to more accurately determine the concentration or expression level of such protein. These approaches are also easily automated using technology known to those of skill in the art of high throughput diagnostic analysis. As detailed above, any addressable array technology known in the art can be employed with this aspect of the invention and display the protein arrays on the chips in an attempt to maximize antibody binding patterns and diagnostic information.

As discussed above, the presence or detection of a polymorphism in an invention gene or protein can provide a diagnosis of a cancer or similar malady in an organism. Additional embodiments include the preparation of diagnostic kits comprising detection components, such as antibodies, specific for a particular polymorphic variant of invention gene or protein. The detection component will typically be supplied in combination with one or more of the following reagents. A support capable of absorbing or otherwise binding RNA or protein will often be supplied. Available supports for this purpose include, but are not limited to, membranes of nitrocellulose, nylon or derivatized nylon that can be characterized by bearing an array of positively charged substituents, and Genechips™ or their equivalents. One or more enzymes, such as Reverse Transcriptase and/or Taq polymerase, can be furnished in the kit, as can dNTPs, buffers, or non-human polynucleotides like calf-thymus or salmon-sperm DNA. Results from the kit assays can be interpreted by a healthcare provider or a diagnostic laboratory. Alternatively, diagnostic kits are manufactured and sold to private individuals for self-diagnosis.

In addition to diagnosing disease according to the presence or absence of a polymorphism, some diseases involving cancer result from skewed levels of invention protein or gene in particular tissues or aberrant patterns of invention protein expression. By monitoring the level of expression in various tissues, for example, a diagnosis can be made or a disease state can be identified. Similarly, by determining ratios of the level of expression of various invention proteins in specific tissues (e.g., patterns of expression) a prognosis of health or disease can be made. The levels of invention protein expression in various tissues from healthy individuals, as well as, individuals suffering from cancers is determined. These values can be recorded in a database and can be compared to values obtained from tested individuals. Additionally, the ratios or patterns of expression in various tissues from both healthy and diseased individuals is recorded in a database. These analyses are referred to as "disease state profiles" and by comparing one disease state profile (e.g. from a healthy or diseased individual) to a disease state profile from a tested individual, a clinician can rapidly diagnose the presence or absence of disease.

The nucleic acid and protein-based diagnostic techniques described above can be used to detect the level or amount or ratio of expression of invention genes or proteins in a tissue. Through quantitative Northern hybridizations, in situ analysis, immunohistochemistry, ELISA, genechip array technology, PCR, and Western blots, for example, the amount or level of expression of RNA or protein for a particular invention protein (wild-type or mutant) can be rapidly determined and from this information ratios of expression can be ascertained. Alternatively, the invention proteins to be analyzed can be family members that are currently unknown but which are identified based on their possession of one or more of the homology regions described above.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Identification of Differentially Expressed mRNA in Cancers-1

Global changes in gene expression between tumor biopsies and normal tissues have been examined using the GeneExpress Oncology Datasuite™ of Gene Logic, Inc. (Gaithersburg, Md.). The database includes the gene expression profiles, generated by using the Affymetrix Human Genome U95 array, derived from normal and cancer tissue samples from many different organs. Among the tissue samples in the database, applicants analyzed the expression profiles of normal and cancer tissue sets from breast, colon, esophagus, kidney, liver, lung, lymph node, ovary, pancreas, prostate, rectum, and stomach.

The Affymetrix Human Genome U95 array contains 63,175 probe sets. A probe set is a set of probes to detect one transcript (a gene or a cDNA clone), and usually consists of 16-20 oligonucleotide probe pairs. These probe pairs include perfectly matched sets and mismatched sets, both of which are necessary for the calculation of average difference. Average difference serves as a relative indicator of the level of expression of a transcript and is a measure of the intensity difference for each probe pair, calculated by subtracting the intensity of the mismatch from the intensity of the perfect match. This takes into consideration variability in hybridization among probe pairs and other hybridization artifacts that could affect the fluorescence intensities. Using the average difference value that has been calculated, an absolute call for each gene is made; "Absent" (=not detected), "Present" (=detected) or "Marginal" (=not clearly Absent or Present).

Differential expression of genes between cancerous and normal tissue samples was determined with the following statistical methods. (1) For each probe set, average difference values and absolute calls were determined by Affymetrix Microarray Suite (v4.0). (2) In a given sample set, outliers among the tissue samples were detected by Principal Component Analysis (PCA) using MatLab program (The MathWorks, Inc., Natick, Mass.). The data points used in the PCA were the average differences of randomly selected probe sets (5,000~6,000 probe sets). Outliers were excluded from further analysis. (3) Variations of gene expression were analyzed by using the Fold Change Analysis tool of GeneExpress program. The fold change (cancerous/normal) was calculated by comparing the mean average difference for each gene in a cancerous sample set against the mean average difference of that gene in the normal tissue sample set. Genes showing at least 3-fold increases or decreases in expression level were obtained. Genes were included in the analysis if they had a p-value of less than or equal to 0.05 as determined by an Analysis of Variance Test (Steel et al., *Principles and Procedures of Statistics: A Biometrical Approach*, Third Ed., McGraw-Hill, 1997). (4) Genes showing differential expression in at least 5 different cancer types were selected.

Analysis of the chip data showed that the expression of the marker LFG1 was significantly up-regulated in cancer tissue samples compared to samples from normal tissue. The expression level of LFG1 (SEQ ID NO: 1 or 3) can be measured by chip sequence fragment no. 91875_s_at on Affymetrix GeneChips™ U95. The 91875_s_at sequence is derived from the EST A1053741. The expression levels of 91875_s_at in various malignant neoplasms, compared to normal control tissues, are shown in Table 1, where the fold-change, the direction of the change (up- or down-regulation), p-value are also indicated. The fold change (cancerous/normal) was calculated by comparing the geometric mean of average difference in a cancerous sample set against the geometric mean of average difference in the normal tissue sample set. A fold change greater than 1.5 was considered to be significant (Wodicka et al. (1997), *Nature Biotech.* 15:1359-1367). Also indicated in the Table 1 are, for each tissue type, the numbers of samples that are called present, absent, or marginal together with the total number of samples in that sample set. These data indicate that up-regulation of LFG1 may be diagnostic for cancer.

TABLE 1

| Tissue | Pathology/Morphology | Geometric Mean | Number of Samples | | | Fold | | |
| --- | --- | --- | --- | --- | --- | --- | --- | --- |
| | | | Total | Present | Marginal | Absent | Change | Direction | p-value |
| BREAST | NORMAL TISSUE, NOS | 22.71 | 34 | 8 | 4 | 22 | | | |
| | INFILTRATING DUCT CARCINOMA | 184.04 | 61 | 61 | 0 | 0 | 8.11 | up | 0 |
| | INFILTRATING LOBULAR CARCINOMA | 104.36 | 10 | 9 | 0 | 1 | 4.60 | up | 0.00456 |

TABLE 1-continued

| Tissue | Pathology/Morphology | Geometric Mean | Number of Samples | | | Fold Change | Direction | p-value |
|---|---|---|---|---|---|---|---|---|
| | | | Total | Present | Marginal | Absent | | | |
| COLON | NORMAL TISSUE, NOS | 76.46 | 24 | 23 | 0 | 1 | | | |
| | ADENOCARCINOMA, NOS | 244.76 | 36 | 35 | 0 | 1 | 3.20 | up | 0.00001 |
| ESOPHAGUS | NORMAL TISSUE, NOS | 50.47 | 18 | 16 | 1 | 1 | | | |
| | ADENOCARCINOMA, NOS | 297.56 | 8 | 8 | 0 | 0 | 5.90 | up | 0.00367 |
| KIDNEY | NORMAL TISSUE, NOS | 20.00 | 25 | 1 | 0 | 24 | | | |
| | CLEAR CELL CARCINOMA | 60.48 | 11 | 10 | 1 | 0 | 3.02 | up | 0.00082 |
| | RENAL CELL CARCINMA | 65.01 | 16 | 13 | 0 | 3 | 3.25 | up | 0.00011 |
| LIVER | NORMAL TISSUE, NOS | 22.06 | 19 | 3 | 0 | 16 | | | |
| | HEPATOCELLULAR CARCINOMA, NOS | 86.74 | 23 | 21 | 0 | 2 | 3.93 | up | 0 |
| LUNG | NORMAL TISSUE, NOS | 21.27 | 32 | 6 | 0 | 26 | | | |
| | ADENOCARCINOMA, NOS | 122.81 | 39 | 38 | 0 | 1 | 5.77 | up | 0 |
| OVARY | NORMAL TISSUE, NOS | 20.21 | 23 | 0 | 0 | 23 | | | |
| | PAPILLARYSEROUSADENOCARCINOMA | 112.80 | 23 | 21 | 0 | 2 | 5.58 | up | 0 |
| PANCREAS | NORMAL TISSUE, NOS | 20.02 | 20 | 1 | 0 | 19 | | | |
| | ADENOCARCINOMA, NOS | 72.55 | 25 | 22 | 0 | 3 | 3.62 | up | 0 |
| RECTUM | NORMAL TISSUE, NOS | 78.86 | 20 | 20 | 0 | 0 | | | |
| | ADENOCARCINOMA, NOS | 259.95 | 22 | 22 | 0 | 0 | 3.30 | up | 0.00008 |
| STOMACH | NORMAL TISSUE, NOS | 36.06 | 18 | 7 | 0 | 11 | | | |
| | ADENOCARCINOMA, NOS | 218.74 | 38 | 36 | 0 | 2 | 6.07 | up | 0 |

The GeneChip expression results, determined by sample binding to chip sequence fragment no. 91875_s_at, were validated by quantitative RT-PCR (Q-RT-PCR) using the Taqman® assay (Perkin-Elmer). PCR primers (5'-GCTGAAG-CAGGAAAATCGCTT-3' (SEQ ID NO: 17) and 5'-TGAGACGGAGTCTCACTCGGT-3' (SEQ ID NO: 18)) designed based on the sequence information file of the specific Affymetrix fragment (91875_s_at) were used in the assay. The target gene in each RNA sample (10 ng of total RNA) was assayed relative to a reference gene. For this purpose, primers (5'-GTTTTTCCTAATTGGCATGAAC-3' (SEQ ID NO: 19) and 5'-CGCCCAAGCTTCCTTTT-3' (SEQ ID NO: 20)) specific to the CTBP1 gene (C-terminal binding protein 1) were used to serve as control primers. This approach provides the relative expression as measured by cycle threshold (Ct) value of the target mRNA relative to an amount of CTBP1 Ct value. The sample panel included total RNA pairs of normal and tumor tissues from colon, kidney, liver, lung, ovary, stomach and pancreas (Ambion, Inc., Austin, Tex.). The Q-RT-PCR data confirms the up-regulation of LFG1 in cancer compared to normal samples.

Example 2

Cloning of Full-Length Human cDNA (LFG1) Corresponding to Differentially Expressed mRNA Species The full-length cDNA having SEQ ID NO: 1 or 3 was obtained by polymerase chain reaction (PCR) and rapid amplification of cDNA ends (RACE) using cDNA library from human heart (ResGen, Huntsville, Ala.). Gene-specific oligos for PCR (5'-CACCCTTTGCCTCTGTCACTTC-CGCA-3' (SEQ ID NO: 21), 5'-GCTGGAGCACCAGGACT-GCATTG-3' (SEQ ID NO: 22), 5'-GGAGCTGAGCAG-CAGTGTAATGAA-3' (SEQ ID NO: 23), 5'-GAGGCCTGCCTGAAGGAGGAGCTTC-3' (SEQ ID NO: 24), 5'-TCTGGAAGTAGTGCAGACGCCTCAGG-3' (SEQ ID NO: 25), 5'-AGCCAACGTCGGCTTTGTTATC-CAGC-3' (SEQ ID NO: 26), 5'-GCTGTCAGATATGATG-GTTCTGGAC-3' (SEQ ID NO: 27), 5'-CCAGCCTCAC-CACTGTTGGGTTGC-3' (SEQ ID NO: 28), 5'-CATTCTCTGAGCTGTATTAGTGT-3' (SEQ ID NO: 29), 5'-CCTGAGCTGGAATGACCTGCA-3' (SEQ ID NO: 30), 5'-CTTTGTGTTGGCTGCAGCCACA-3' (SEQ ID NO: 31), 5'-TGAGGAGAGACTTTGCTGACTGGT-3' (SEQ ID NO: 32), 5'-GTCCTGTCTGGCGGTGCCGA-3' (SEQ ID NO: 33), 5'-GCTCCAGGATCCCCTGTCACCTGGGCCT-TCTGC CT=GGCT-3' (SEQ ID NO: 34), 5'-CCATATG-GAGAGGAGAGCAGCGGGCCCA-3' (SEQ ID NO: 35), 5'-GAAGGAGGAACATGGAGAGGAGA-3' (SEQ ID NO: 36), 5'-CCATATGCCCCGGGTAGTCTACTGCAT-3' (SEQ ID NO: 37), and 5'-GTCGACTCGAGTCACTTCCG-CAAAAACTTCTTG-3' (SEQ ID NO: 38)) and RACE (5'-TCCATTCCGAAGGCTCTCCTCC-3' (SEQ ID NO: 39), 5'-GTCTGTGTGACGGAAATGTAAGC-3' (SEQ ID NO: 40), and 5'-GAAGGTCGAAGGCAGACCGATGT-3' (SEQ ID NO: 41)) were designed based on predicted genes containing the 91875_s_at sequence using Human Genome Browser (University of California, Santa Cruz). The amplified products with the primers were incorporated into PCR4-Topo vector using Topo Cloning System (Invitrogen, Carlsbad, Calif.), and followed by sequencing.

The nucleotide sequence of the full-length human cDNAs corresponding to the differentially regulated mRNA detected above is set forth in SEQ ID NOS: 1 and 3. In the former, the cDNA comprises 5293 base pairs. In the latter, the cDNA comprises 5317 base pairs.

Figure 2:
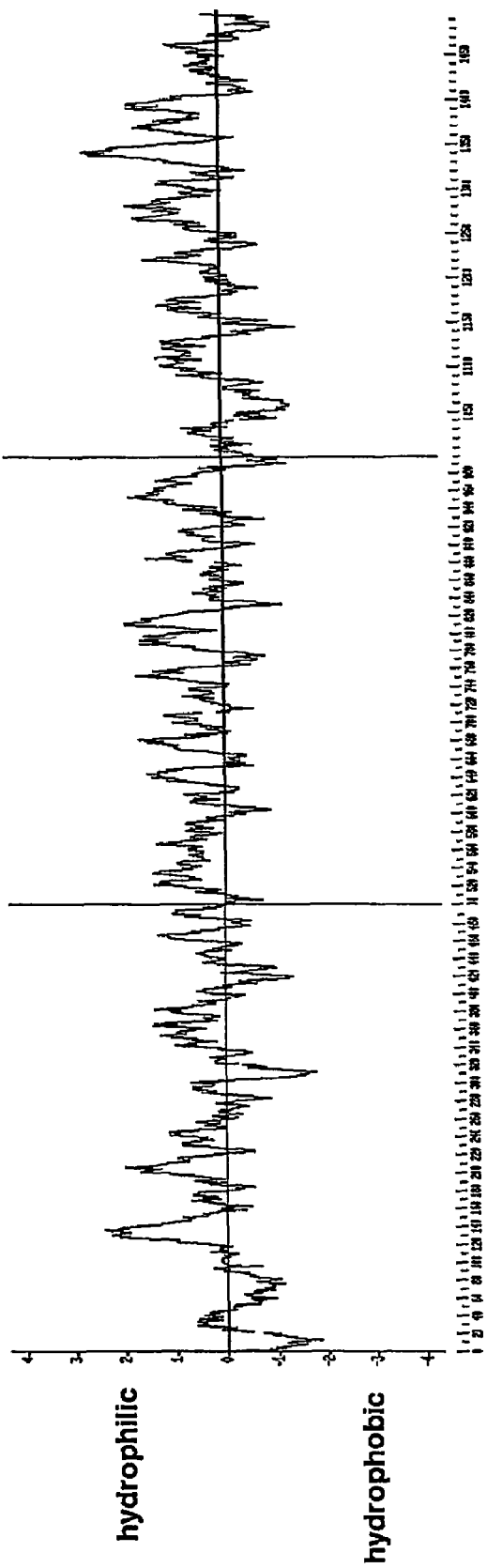
FIG. 2 is a hydrophobicity plot of the protein encoded by the open reading frame of LFG1-Clone A (SEQ ID NO: 2). Analysis was performed according to the method of Kyte-Doolittle.

An open reading frame within the cDNA nucleotide sequence of SEQ ID NO: 1, at nucleotides 390-4880 (390-4883 including the stop codon), encodes a protein of 1497 amino acids. The amino acid sequence corresponding to a predicted protein encoded by SEQ ID NO: 1 is set forth in SEQ ID NO: 2. FIG. 2 shows the results of a hydrophobicity analysis of the amino acid sequence of SEQ ID NO: 2 using Kyte-Doolittle values byte and Doolittle (1982), *J. Mol. Biol.* 157:105-142). Hydrophilic regions may be used to produce antigenic peptides, as described above.

Figure 3:
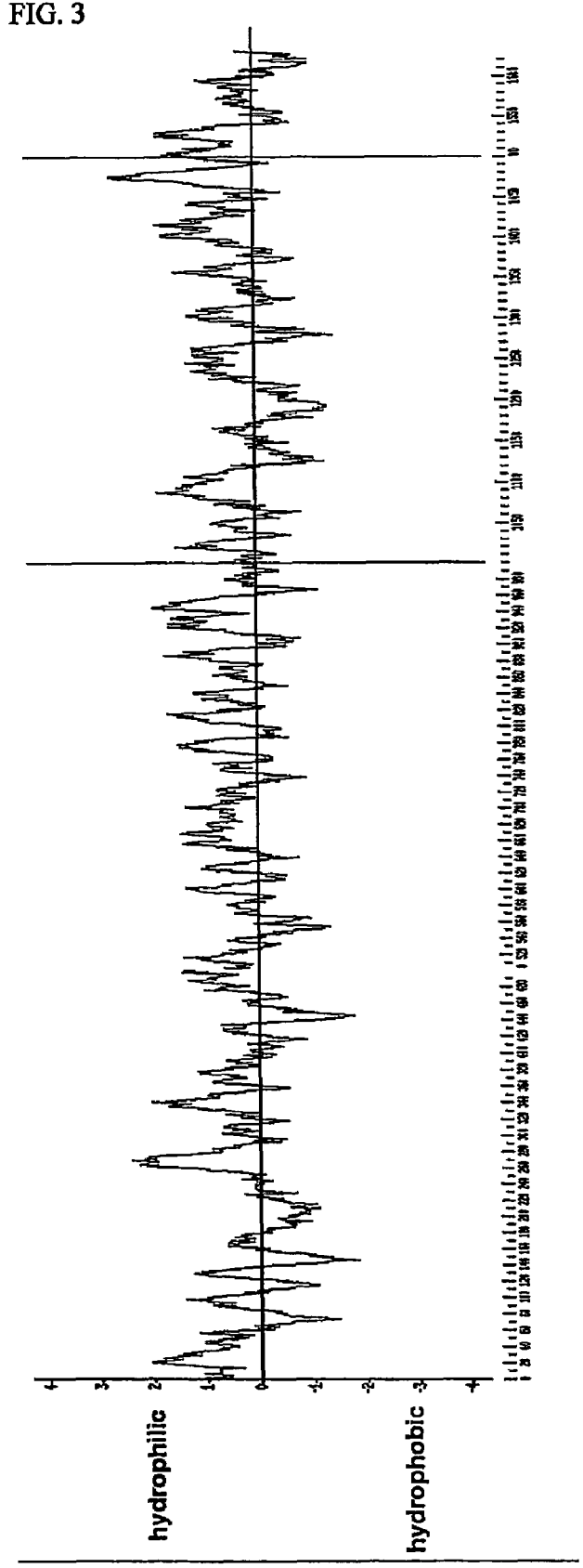
FIG. 3 is a hydrophobicity plot of the protein encoded by the open reading frame of LFG1-Clone B (SEQ ID NO: 4). Analysis was performed according to the method of Kyte-Doolittle.

An open reading frame within the cDNA nucleotide sequence of SEQ ID NO: 3, at nucleotides 124904 (12-4907 including the stop codon), encodes a protein of 1631 amino acids. The amino acid sequence corresponding to a predicted protein encoded by SEQ ID NO: 3 is set forth in SEQ ID NO: 4. FIG. 3 shows the results of a hydrophobicity analysis of the amino acid sequence of SEQ ID NO: 4 using Kyte-Doolittle values (Kyte and Doolittle (1982), *J. Mol. Biol.* 157:105-142). Hydrophilic regions may be used to produce antigenic peptides, as described above.

The protein sequence of SEQ ID NO: 2 is identical to that of SEQ ID NO: 4, except that SEQ ID NO: 2 lacks the first 134 amino acids at the N-terminus of SEQ ID NO: 4.

SEQ ID NOS: 2 and 4 contain Calponin homology domain (amino acid positions 38-145 of SEQ ID NO: 4), IQ domain for calmodulin-binding (amino acid positions 629-646 of SEQ ID NO: 2 and amino acid positions 763-780 of SEQ ID NO: 4), RasGAP domain (amino acid positions 858-1195 of SEQ ID NO: 2 and amino acid positions 992-1329 of SEQ ID NO: 4), and RasGAP C-terminal domain (amino acid positions 1298-1421 of SEQ ID NO: 2 and amino acid positions 1432-1555 of SEQ ID NO: 4). SEQ ID NOS: 2 and 4 are similar to IQGAP proteins (Weissbach et al. (1994), *J Biol Chem* 269:20517-20521; Brill et al. (1996), *Mol Cell Biol* 16:4869-4878). IQGAP binds to and modulate the function of proteins involved in cytoskeletal structure, cell-cell adhesion, and proliferation signaling (Fukada et al. (2002), *Cell* 109: 1-20; Briggs et al. (2002), *J Biol Chem* 277: 7453-7465; McCallum et al. (1998), *J Biol Chem* 273: 22537-22544). IQGAP1-deficient mice exhibited a significant increase in late-onset gastric hyperplasia relative to wild-type (Li et al. (2000), *Mol Cell Biol* 20: 697-701).

Analysis by Northern blot was performed to determine the size of the mRNA transcripts that correspond to LFG1. A Northern blot containing total RNAs from various human tissues was used (Human 12-Lane MTN Blot, Clontech, Palo Alto, Calif.), and an EST containing 91875_s_at sequence was radioactively labeled by the random primer method and used to probe the blot. The blot was hybridized in 50% formamide, 5×SSPE, 0.1% SDS, 5× Denhart's solution, and 0.2 mg/ml herring sperm DNA at 42° C. and washed with 0.2× SSC containing 0.1% SDS at room temperature. The Northern blot showed three transcripts for this gene, which are approximately 7.2 kb, and 6.3 kb in size. This corresponds to the sizes of the LFG1 clones (SEQ ID NO: 1 and 3).

Example 3

Identification of Differentially Expressed mRNA in Cancers-2

The process in EXAMPLE 1 was repeated except that the marker LFG2 was used instead of the marker LFG1.

Analysis of the chip data showed that the expression of the marker LFG2 was significantly down-regulated in cancer tissue samples compared to samples from normal tissue. The expression level of LFG2 (SEQ ID NO: 5) can be measured by chip sequence fragment no. 82941_at on Affymetrix GeneChips® U95. The 82941_at sequence is derived from the EST AI277612. The expression levels of 82941_at in various malignant neoplasms, compared to normal control tissues, are shown in Table 2, where the fold-change, the direction of the change (up- or down-regulation), p-value are also indicated. The fold change (cancerous/normal) was calculated by comparing the geometric mean of average difference in a cancerous sample set against the geometric mean of average difference in the normal tissue sample set. A fold-change greater than 1.5 was considered to be significant (Wodicka et al. (1997), *Nature Biotech.* 15:1359-1367). Also indicated in the Table 2 are, for each tissue type, the numbers of samples that are called present, absent, or marginal together with the total number of samples in that sample set. These data indicate that down-regulation of LFG2 may be diagnostic for cancer.

TABLE 2

| Tissue | Pathology/Morphology | Geometric Mean | Number of Samples | | | Fold | | |
|---|---|---|---|---|---|---|---|---|
| | | | Total | Present | Marginal | Absent | Change | Direction | p-value |
| BREAST | NORMAL TISSUE, NOS | 1147.66 | 34 | 34 | 0 | 0 | | | |
| | INFILTRATING DUCT CARCINOMA | 129.77 | 61 | 26 | 3 | 32 | 8.71 | down | 0 |
| | INFILTRATING LOBULAR CARCINOMA | 183.37 | 10 | 6 | 1 | 3 | 5.48 | down | 0.00002 |
| COLON | NORMAL TISSUE, NOS | 890.06 | 24 | 23 | 1 | 0 | | | |
| | ADENOCARCINOMA, NOS | 163.35 | 36 | 17 | 1 | 18 | 5.39 | down | 0 |
| ESOPHAGUS | NORMAL TISSUE, NOS | 612.34 | 18 | 18 | 0 | 0 | | | |
| | ADENOCARCINOMA, NOS | 265.11 | 8 | 7 | 1 | 0 | 2.31 | down | 0.02218 |
| LIVER | NORMAL TISSUE, NOS | 182.73 | 19 | 11 | 1 | 7 | | | |
| | HEPATOCELLULAR CARCINOMA, NOS | 114.69 | 23 | 7 | 1 | 15 | 1.51 | down | 0.01211 |
| LUNG | NORMAL TISSUE, NOS | 535.64 | 32 | 30 | 2 | 0 | | | |
| | ADENOCARCINOMA, NOS | 119.36 | 39 | 17 | 3 | 19 | 4.27 | down | 0 |
| LYMPH NODE | NORMAL TISSUE, NOS | 454.08 | 9 | 7 | 0 | 2 | | | |
| | MALIGNANT LYMPHOMA, NOS | 123.13 | 12 | 5 | 0 | 7 | 3.24 | down | 0.02245 |
| OVARY | NORMAL TISSUE, NOS | 279.99 | 23 | 21 | 0 | 2 | | | |
| | PAPILLARY SEROUS ADENOCARCINOMA | 85.45 | 23 | 7 | 1 | 15 | 3.5 | down | 0 |
| PROSTATE | NORMAL TISSUE, NOS | 195.77 | 19 | 13 | 1 | 5 | | | |
| | ADENOCARCINOMA, NOS | 80.06 | 19 | 2 | 2 | 15 | 2.57 | down | 0.00011 |
| RECTUM | NORMAL TISSUE, NOS | 943.86 | 20 | 19 | 0 | 1 | | | |
| | ADENOCARCINOMA, NOS | 176.45 | 22 | 13 | 2 | 7 | 5.2 | down | 0 |
| STOMACH | NORMAL TISSUE, NOS | 414.40 | 18 | 16 | 0 | 2 | | | |
| | ADENOCARCINOMA, NOS | 125.39 | 38 | 17 | 2 | 19 | 3.21 | down | 0 |

The GeneChip expression results, determined by sample binding to chip sequence fragment no. 82941_at, were validated by quantitative RT-PCR (Q-RT-PCR) using the Taqman® assay (Perkin-Elmer). PCR primers (5'-GAATGTGT-CAGAGACAAGTGCAGC-3' (SEQ ID NO: 42) and 5'-TGTAGAAACTCTTGGACTAATGGAGG-3' (SEQ ID NO: 43)) designed based on the sequence information file of the EST containing the Affymetrix fragment (82941_at) were used in the assay. The target gene in each RNA sample (10 ng of total RNA) was assayed relative to a reference gene. For this purpose, primers (5'-GTTTTTCCTAATTTTGGCAT-GAAC-3' (SEQ ID NO: 19) and 5'-CGCCCAAGCTTTTC-CTTTT-3' (SEQ ID NO: 20)) specific to the CTBP1 gene (C-terminal binding protein 1) were used to serve as control primers. This approach provides the relative expression as measured by cycle threshold (Ct) value of the target mRNA relative to an amount of CTBP1 Ct value. The sample panel included total RNA pairs of normal and tumor tissues from colon, liver, lung, ovary, and stomach (Ambion, Inc., Austin, Tex.). The Q-RT-PCR data confirms the down-regulation of LFG2 in cancer compared to normal samples.

Example 4

Cloning of Full-Length Human cDNA (LFG2) Corresponding to Differentially Expressed mRNA Species The full-length cDNA having SEQ ID NO: 5 was obtained by the oligo-pulling method using the GeneTrapper assay (Life Technologies, Rockville, Md.). Briefly, a gene-specific oligo (5'-GAATGTGTCAGAGACAAGTGCAGC-3' (SEQ ID NO: 42)) was designed based on the sequence of the EST containing 82941_at sequence. The oligo was labeled with biotin and used to hybridize with 5 μg of single strand plasmid DNA (cDNA recombinants) from a poorly differentiated stomach adenocarcinoma library (NCI CGAP Gas4) (Res-Gen, Huntsville, Ala.) following the procedures of Sambrook et al. The hybridized cDNAs were separated by streptavidin-conjugated beads and eluted by heating. The eluted cDNA was converted to double strand plasmid DNA and used to transform *E. coli* cells (DH10B) and the longest cDNA was screened. After positive selection was confirmed by PCR using gene-specific primers, the cDNA clone was subjected to DNA sequencing.

The nucleotide sequence of the full-length human cDNAs corresponding to the differentially regulated mRNA detected above is set forth in SEQ ID NO: 5. The cDNA comprises 3608 base pairs.

An open reading frame within the cDNA nucleotide sequence of SEQ ID NO: 5, at nucleotides 424-1908 (424-1911 including the stop codon), encodes a protein of 495 amino acids. The amino acid sequence corresponding to a predicted protein encoded by SEQ ID NO: 5 is set forth in SEQ ID NO: 6.

SEQ ID NO: 6 has homology to scavenger receptors, which are involved in endocytosis of selected polyanionic ligands, phagocytosis of apoptotic cells and bacteria, cell adhesion, and development of atherosclerosis (Peiser et al. (2002), *Curr. Opin. Immunol.* 14:123-128; Resnick et al. (1994), *Trends Biol. Sci.* 19:5-8). Based on published studies of scavenger receptors, SEQ ID NO: 6 contains a cytoplasmic domain (amino acid positions 1-35), a transmembrane domain (amino acid positions 36-58), an α-helical coiled-coil domain (amino acid positions 90-301), a collagen-like domain (amino acid positions 305-380), and a scavenger receptor cystein-rich (SRCR) domain (amino acid positions 393-493). The SRCR domain contains six cysteine residues (amino acid positions 418, 431, 462, 472, 482, and 492), which may participate in intradomain disulfide bonds. SEQ ID NO: 6 also exhibits homology to a mouse homologue (GenBank Accession No. BC016096). It shows 70% identity over the entire contiguous sequence.

Figure 4:
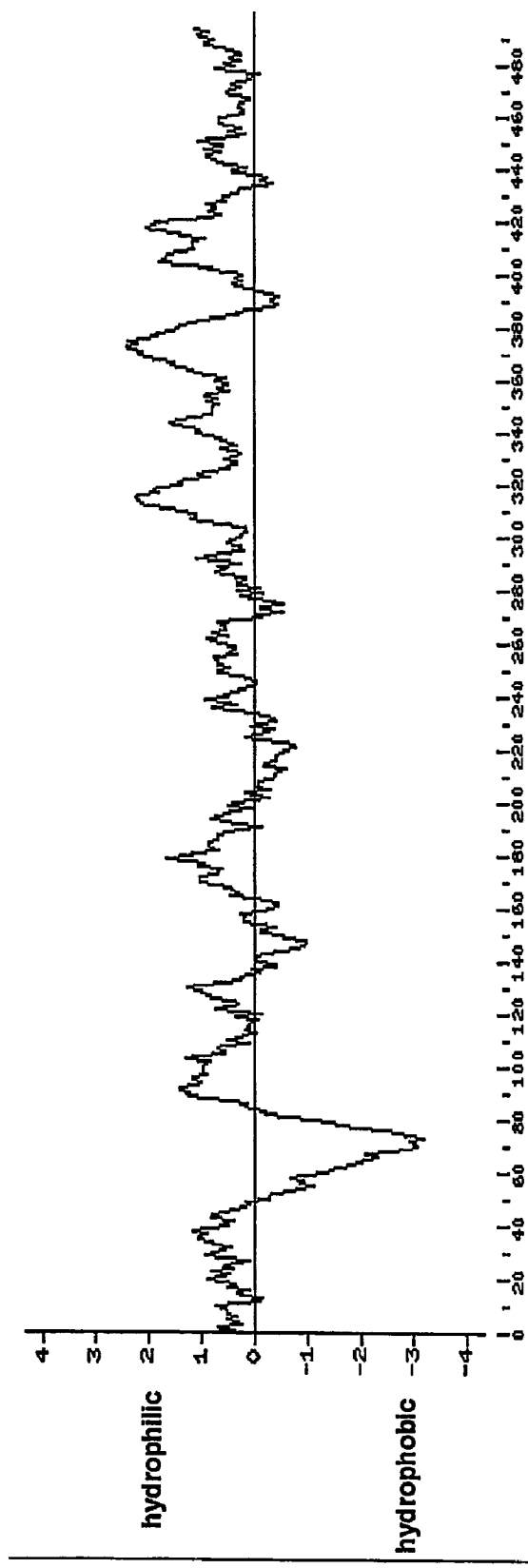
FIG. 4 is a hydrophobicity plot of the protein encoded by the open reading frame of LFG2 (SEQ ID NO: 6). Analysis was performed according to the method of Kyte-Doolittle.

FIG. 4 shows the results of a hydrophobicity analysis of the amino acid sequence of SEQ ID NO: 6 using Kyte-Doolittle values (Kyte and Doolittle (1982), *J. Mol. Biol.* 157:105-142). Hydrophilic regions may be used to produce antigenic peptides, as described above.

Analysis by Northern blot was performed to determine the size of the mRNA transcripts that correspond to LFG2. A Northern blot containing total RNAs from various human tissues was used (Human MTN Blot, Clontech, Palo Alto, Calif.), and the EST containing 82941_at sequence was radioactively labeled by the random primer method and used to probe the blot. The blot was hybridized in 50% formamide, 5×SSPE, 0.1% SDS, 5× Denhart's solution, and 0.2 mg/ml herring sperm DNA at 42° C. and washed with 0.2×SSC containing 0.1% SDS at room temperature. The Northern blot showed a single transcript for this gene, which is approximately 3.7 kb in size. This corresponds to the size of the LFG2 clone (SEQ ID NO: 5).

Example 5

Identification of Differentially Expressed mRNA in Cancers-3

The process in EXAMPLE 1 was repeated except that the marker LFG3 was used instead of the marker LFG1.

Analysis of the chip data showed that the expression of the marker LFG3 was significantly down-regulated in cancer tissue samples compared to samples from normal tissue. The expression level of LFG3 (SEQ ID NO: 7) can be measured by chip sequence fragment no. 46104_at on Affymetrix GeneChips® U95. The 46104_at sequence is derived from the EST AA772055. The expression levels of 46104_at in various malignant neoplasms, compared to normal control tissues, are shown in Table 3, where the fold-change, the direction of the change (up- or down-regulation), p-value are also indicated. The fold change (cancerous/normal) was calculated by comparing the geometric mean of average difference in a cancerous sample set against the geometric mean of average difference in the normal tissue sample set. A fold-change greater than 1.5 was considered to be significant (Wodicka et al. (1997), Nature Biotech. 15:1359-1367). Also indicated in the Table 3 are, for each tissue type, the numbers of samples that are called present, absent, or marginal together with the total number of samples in that sample set. These data indicate that down-regulation of LFG3 may be diagnostic for cancer.

TABLE 3

| Tissue | Pathology/Morphology | Geometric Mean | Number of Samples | | | | Fold Change | Direction | p-value |
|---|---|---|---|---|---|---|---|---|---|
| | | | Total | Present | Marginal | Absent | | | |
| BREAST | NORMAL TISSUE, NOS | 64.52 | 34 | 31 | 0 | 3 | | | |
| | INFILTRATING DUCT | 27.24 | 61 | 18 | 1 | 42 | 2.25 | down | 0 |

TABLE 3-continued

| Tissue | Pathology/Morphology | Geometric Mean | Number of Samples | | | Fold Change | Direction | p-value |
|---|---|---|---|---|---|---|---|---|
| | | | Total | Present | Marginal | Absent | | | |
| | CARCINOMA INFILTRATING LOBULAR CARCINOMA | 29.52 | 10 | 4 | 0 | 6 | 2.21 | down | 0.00004 |
| COLON | NORMAL TISSUE, NOS | 315.46 | 24 | 24 | 0 | 0 | | | |
| | ADENOCARCINOMA, NOS | 102.99 | 36 | 31 | 0 | 5 | 3.02 | down | 0.00016 |
| ESOPHAGUS | NORMAL TISSUE, NOS | 272.48 | 18 | 17 | 0 | 1 | | | |
| | ADENOCARCINOMA, NOS | 41.25 | 8 | 6 | 0 | 2 | 6.60 | down | 0.00001 |
| KIDNEY | NORMAL TISSUE, NOS | 2626.88 | 25 | 25 | 0 | 0 | | | |
| | CLEAR CELL ADENOCARCINOMA, NOS | 344.66 | 11 | 11 | 0 | 0 | 7.62 | down | 0.00003 |
| | RENAL CELL CARCINOMA | 355.71 | 16 | 14 | 0 | 2 | 7.38 | down | 0.00005 |
| OVARY | NORMAL TISSUE, NOS | 1098.41 | 23 | 23 | 0 | 0 | | | |
| | PAPILLARY SEROUS ADENOCARCINOMA | 178.15 | 23 | 22 | 0 | 1 | 6.17 | down | 0 |
| PROSTATE | NORMAL TISSUE, NOS | 274.49 | 19 | 19 | 0 | 0 | | | |
| | ADENOCARCINOMA, NOS | 117.26 | 19 | 18 | 0 | 1 | 2.34 | down | 0.00016 |
| RECTUM | NORMAL TISSUE, NOS | 410.22 | 20 | 20 | 0 | 0 | | | |
| | ADENOCARCINOMA, NOS | 72.98 | 22 | 16 | 0 | 6 | 5.38 | down | 0 |
| STOMACH | NORMAL TISSUE, NOS | 71.10 | 18 | 10 | 0 | 8 | | | |
| | ADENOCARCINOMA, NOS | 35.49 | 38 | 15 | 1 | 22 | 1.96 | down | 0.00459 |

The GeneChip expression results, determined by sample binding to chip sequence fragment no. 46104_at, were validated by quantitative RT-PCR (Q-RT-PCR) using the Taqman® assay (Perkin-Elmer). PCR primers (5'-GTATGCAT-CAGAATTCCCTATAGATCTTT-3' (SEQ ID NO: 44) and 5'-TAGATGTTTGGGCAACAGCCT-3' (SEQ ID NO: 45)) designed based on the sequence information file of the EST containing the Affymetrix fragment (46104_at) were used in the assay. The target gene in each RNA sample (10 ng of total RNA) was assayed relative to a reference gene. For this purpose, primers (5'-GTTTTTCCTAATTTGGCATGAAC-3' (SEQ ID NO: 19) and 5'-CGCCCAAGCTTTTCCTTTT-3' (SEQ ID NO: 20)) specific to the CTBP1 gene (C-terminal binding protein 1) were used to serve as control primers. This approach provides the relative expression as measured by cycle threshold (Ct) value of the target mRNA relative to an amount of CTBP1 Ct value. The sample panel included total RNA pairs of normal and tumor tissues from colon, kidney, ovary, pancreas, and stomach (Ambion, Inc., Austin, Tex.). The Q-RT-PCR data confirms the down-regulation of LFG3 in cancer compared to normal samples.

Example 6

Cloning of Full-Length Human cDNA (LFG3) Corresponding to Differentially Expressed mRNA Species The full-length cDNA having SEQ ID NO: 7 was obtained by the oligo-pulling method using the GeneTrapper assay (Life Technologies, Rockville, Md.). Briefly, a gene-specific oligo (5'-GTATGCATCAGAATTCCCTATAGATCTTT-3' (SEQ ID NO: 44)) was designed based on the sequence of the EST containing 46104_at sequence. The oligo was labeled with biotin and used to hybridize with 5 μg of single strand plasmid DNA (cDNA recombinants) from human fetal kidney (ResGen, Huntsville, Ala.) following the procedures of Sambrook et al. The hybridized cDNAs were separated by streptavidin-conjugated beads and eluted by heating. The eluted cDNA was converted to double strand plasmid DNA and used to transform E. coli cells (DH10B) and the longest cDNA was screened. After positive selection was confirmed by PCR using gene-specific primers, the cDNA clone was subjected to DNA sequencing. The 5'-end of LFG3 was identified by rapid amplification of cDNA ends (RACE) using the cDNA prepared from human fetal kidney (Clontech, Palo Alto, Calif.) and a gene specific primer (5'-TTCCTTCAC-CAAAGGCATCCAGCCATTCTATG-3' (SEQ ID NO: 46)).

The nucleotide sequence of the full-length human cDNAs corresponding to the differentially regulated mRNA detected above is set forth in SEQ ID NO: 7. The cDNA comprises 3162 base pairs.

An open reading frame within the cDNA nucleotide sequence of SEQ ID NO: 7, at nucleotides 405-1835 (405-1838 including the stop codon), encodes a protein of 477 amino acids. The amino acid sequence corresponding to a predicted protein encoded by SEQ ID NO: 7 is set forth in SEQ ID NO: 8.

SEQ ID NO: 8 is similar to monocarboxylate transporters (MCTs) and contains ten predicted transmembrane domains (amino acids positions 10-29, 80-99, 107-128, 140-160, 274-295, 312-332, 339-360, 363-384, 396416, and 433-451). MCT proteins catalyze the facilitated transport of monocarboxylates such as lactate, pyruvate, branched-chain oxo acids, ketone bodies, beta-hydroxy-butylate, and acetate (Halestrap and Price (1999), *Biochem. J.* 343:281-299). Table 4 summarizes the similarity ratios of SEQ ID NO: 4 with the eight known monocarboxylate transporters.

TABLE 4

Homology of LFG3 with MCT proteins

| Protein | Size (amino acids) | Identity (%) | Positives (%) |
|---|---|---|---|
| MCT1 | 500 | 17.5 | 34.3 |
| MCT2 | 478 | 19.5 | 35.5 |
| MCT3 | 504 | 19.5 | 34.1 |
| MCT4 | 465 | 19.0 | 33.2 |
| MCT5 | 487 | 22.1 | 36.9 |
| MCT6 | 505 | 16.4 | 31.5 |
| MCT7 | 523 | 20.1 | 35.2 |
| MCT8 | 613 | 15.9 | 27.9 |

Figure 5:
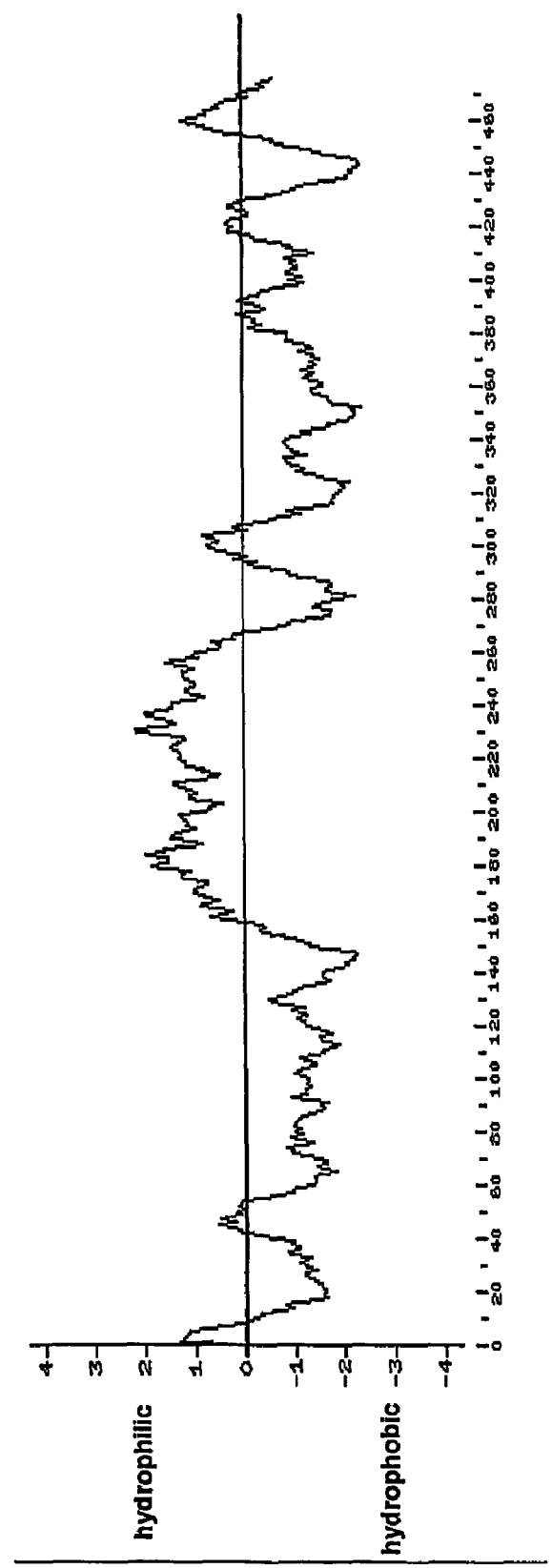
FIG. 5 is a hydrophobicity plot of the protein encoded by the open reading frame of LFG3 (SEQ ID NO: 8). Analysis was performed according to the method of Kyte-Doolittle.

FIG. 5 shows the results of a hydrophobicity analysis of the amino acid sequence of SEQ ID NO: 8 using Kyte-Doolittle values (Kyte and Doolittle (1982), *J. Mol. Biol.* 157:105-142). Hydrophilic regions may be used to produce antigenic peptides, as described above.

Analysis by Northern blot was performed to determine the size of the mRNA transcripts that correspond to LFG3. A Northern blot containing total RNAs from various human tissues was used (Human 12-Lane MTN Blot, Clontech, Palo Alto, Calif.), and the EST containing 46104_at sequence was radioactively labeled by the random primer method and used to probe the blot. The blot was hybridized in 50% formamide, 5×SSPE, 0.1% SDS, 5× Denhart's solution, and 0.2 mg/ml herring sperm DNA at 42° C. and washed with 0.2×SSC containing 0.1% SDS at room temperature. The Northern blot showed a single transcript for this gene, which is approximately 4.2 kb in size. This corresponds to the size of the LFG3 clone (SEQ ID NO: 7).

Example 7

Identification of Differentially Expressed mRNA in Cancers-4

The process in EXAMPLE 1 was repeated except that the marker LFG4 was used instead of the marker LFG1.

Analysis of the chip data showed that the expression of the marker LFG4 was significantly down-regulated in cancer tissue samples compared to samples from normal tissue. The expression level of LFG4 (SEQ ID NO: 9) can be measured by chip sequence fragment no. 62158_at on Affymetrix GeneChips® U95. The 622158_at sequence is derived from the EST AI123532. The expression levels of 62158_at in various malignant neoplasms, compared to normal control tissues, are shown in Table 5, where the fold-change, the direction of the change (up- or down-regulation), p-value are also indicated. The fold change (cancerous/normal) was calculated by comparing the geometric mean of average difference in a cancerous sample set against the geometric mean of average difference in the normal tissue sample set. A fold-change greater than 1.5 was considered to be significant (Wodicka et al. (1997), Nature Biotech. 15:1359-1367). Also indicated in the Table 5 are, for each tissue type, the numbers of samples that are called present, absent, or marginal together with the total number of samples in that sample set. These data indicate that down-regulation of LFG4 may be diagnostic for cancer.

TABLE 5

| Tissue | Pathology/Morphology | Geometric Mean | Total | Present | Marginal | Absent | Fold Change | Direction | p-value |
|---|---|---|---|---|---|---|---|---|---|
| BREAST | NORMAL TISSUE, NOS | 156.75 | 34 | 33 | 0 | 1 | | | |
|  | INFILTRATING DUCT CARCINOMA | 90.09 | 61 | 51 | 0 | 10 | 1.74 | down | 0.00001 |
| COLON | NORMAL TISSUE, NOS | 234.06 | 24 | 22 | 2 | 0 | | | |
|  | ADENOCARCINOMA, NOS | 64.02 | 36 | 24 | 0 | 12 | 3.66 | down | 0 |
| KIDNEY | NORMAL TISSUE, NOS | 134.17 | 25 | 23 | 0 | 2 | | | |
|  | CLEAR CELL ADENOCARCINOMA, NOS | 78.59 | 11 | 7 | 1 | 3 | 1.71 | down | 0.08272 |
|  | RENAL CELL CARCINOMA | 55.31 | 16 | 9 | 0 | 7 | 2.43 | down | 0.0021 |
| LUNG | NORMAL TISSUE, NOS | 179.71 | 32 | 32 | 0 | 0 | | | |
|  | ADENOCARCINOMA, NOS | 47.39 | 39 | 17 | 3 | 19 | 3.79 | down | 0 |
| LYMPH NODE | NORMAL TISSUE, NOS | 140.51 | 9 | 7 | 1 | 1 | | | |
|  | MALIGNANT LYMPHOMA, NOS | 41.43 | 12 | 5 | 1 | 6 | 3.39 | down | 0.00207 |
| OVARY | NORMAL TISSUE, NOS | 125.19 | 23 | 21 | 0 | 2 | | | |
|  | PAPILLARY SEROUS ADENOCARCINOMA | 37.23 | 23 | 4 | 0 | 19 | 3.36 | down | 0 |
| PROSTATE | NORMAL TISSUE, NOS | 191.94 | 19 | 18 | 0 | 1 | | | |
|  | ADENOCARCINOMA, NOS | 103.47 | 19 | 16 | 0 | 3 | 1.86 | down | 0.00185 |
| RECTUM | NORMAL TISSUE, NOS | 317.95 | 20 | 20 | 0 | 0 | | | |
|  | ADENOCARCINOMA, NOS | 74.28 | 22 | 16 | 1 | 5 | 4.28 | down | 0 |
| STOMACH | NORMAL TISSUE, NOS | 161.77 | 18 | 17 | 0 | 1 | | | |
|  | ADENOCARCINOMA, NOS | 84.55 | 38 | 27 | 2 | 9 | 1.91 | down | 0.0062 |

The GeneChip expression results, determined by sample binding to chip sequence fragment no. 62158_at, were validated by quantitative RT-PCR (Q-RT-PCR) using the Taqman® assay (Perkin-Elmer). PCR primers (5'-AAATGTCT-GATTACCCCATTTTATCAGT-3' (SEQ ID NO: 47) and 5'-TAATCCTGAAATGAACAGCTAACA-3') (SEQ ID NO: 48) designed based on the sequence information file of the EST containing the Affymetrix fragment (62158_at) were used in the assay. The target gene in each RNA sample (10 ng of total RNA) was assayed relative to a reference gene. For this purpose, primers (5'-GTTTTTCCTAATFTTGGCAT-GAAC-3' (SEQ ID NO: 19) and 5'-CGCCCAAGCTTTTC-CTTTT-3' (SEQ ID NO: 20)) specific to the CTBP1 gene (C-terminal binding protein 1) were used to serve as control primers. This approach provides the relative expression as measured by cycle threshold (Ct) value of the target mRNA relative to an amount of CTBP1 Ct value. The sample panel included total RNA pairs of normal and tumor tissues from colon, liver, lung, ovary, pancreas, and stomach (Ambion, Inc., Austin, Tex.). The Q-RT-PCR data confirms the down-regulation of LFG4 in cancer compared to normal samples.

Example 8

Cloning of Full-Length Human cDNA (LFG4) Corresponding to Differentially Expressed mRNA Species The full-length cDNA having SEQ ID NO: 9 was obtained by rapid amplification of cDNA ends (RACE). Briefly, gene-specific oligos (5'-TAATGTTAGAGTAACAGCATTTTC-CTTCAA-3' (SEQ ID NO: 49) and 5'-TGCCCCACAC-TAACTCAGTTCTTGTGATG-3' (SEQ ID NO: 50)) were designed based on the sequence of the EST containing 62158_at sequence. The oligos was used for PCR amplification of the cDNAs prepared from human brain (Clontech, Palo Alto, Calif.). The amplified products with the primers were incorporated into PCR4-Topo vector using Topo Cloning System (Invitrogen, Carlsbad, Calif.), and followed by sequencing.

The nucleotide sequence of the full-length human cDNAs corresponding to the differentially regulated mRNA detected above is set forth in SEQ ID NO: 9. The cDNA comprises 4891 base pairs.

An open reading frame within the cDNA nucleotide sequence of SEQ ID NO: 9, at nucleotides 89-1150 (89-1153 including the stop codon), encodes a protein of 354 amino acids. The amino acid sequence corresponding to a predicted protein encoded by SEQ ID NO: 9 is set forth in SEQ ID NO: 10.

SEQ ID NO: 10 is similar to rat Kilon and chicken Neurotractin (Funatsu et al. (1999), *J Biol Chem* 274:8224-8230; Marg et al. (1999), *J Cell Biol* 145:865-876). Protein sequence analysis reveals a secretory signal peptide (amino acid positions 1-33), three immunoglobulin domains (amino acid positions 47-136, 145-208, and 231-312), and six putative N-linked glycosylation sites (amino acid positions 73, 155, 275, 286, 294, and 307).

Kilon/Neurotractin is a member of IgLON subfamily of the immunoglobulin superfamily.

IgLONs are a family of glycosylphosphatidylinositol (GPI)-linked cell adhesion molecules which are thought to modify neurite outgrowth and might play a role in cell-cell adhesion and recognition (Miyate et al. (2000), *J Comparative Neurol* 424:74-85).

Figure 6:
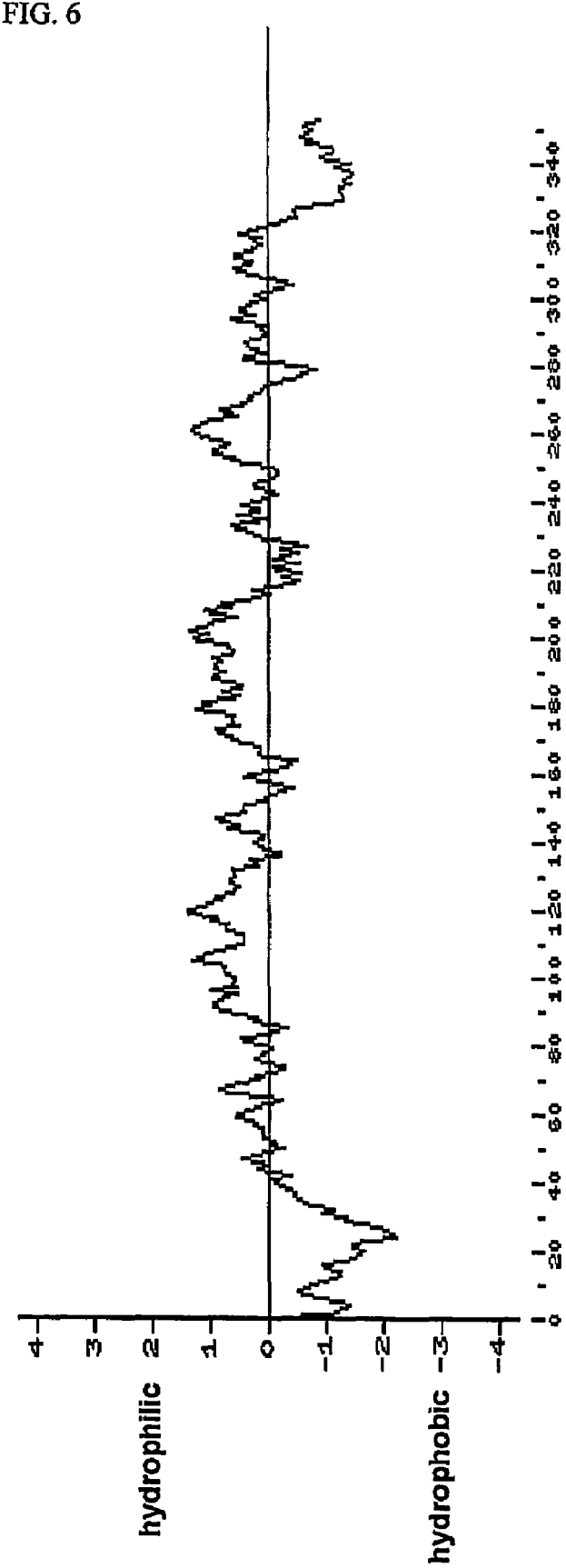
FIG. 6 is a hydrophobicity plot of the protein encoded by the open reading frame of LFG4 (SEQ ID NO: 10). Analysis was performed according to the method of Kyte-Doolittle.

FIG. 6 shows the results of a hydrophobicity analysis of the amino acid sequence of SEQ ID NO: 10 using Kyte-Doolittle values (Kyte and Doolittle (1982), *J Mol. Biol.* 157:105-142). Hydrophilic regions may be used to produce antigenic peptides, as described above. This hydropathy plot shows the presence of hydrophobic region at the C-terminus. In case of GPI-anchored proteins, the addition of the GPI anchor is known to occur after the cleavage of the C-terminal hydrophobic region. A putative GPI anchor attachment site was found (Gly at the amino acid position 324).

Analysis by Northern blot was performed to determine the size of the mRNA transcripts that correspond to LFG4. A Northern blot containing total RNAs from various human tissues was used (Human 12-Lane MTN Blot, Clontech, Palo Alto, Calif.), and the EST containing 62158_at sequence was radioactively labeled by the random primer method and used to probe the blot. The blot was hybridized in 50% formamide, 5×SSPE, 0.1% SDS, 5× Denhart's solution, and 0.2 mg/ml herring sperm DNA at 42° C. and washed with 0.2×SSC containing 0.1% SDS at room temperature. The Northern blot showed a single transcript for this gene, which is approximately 5.4 kb in size. This corresponds to the size of the LFG4 clone (SEQ ID NO: 9).

Example 9

Identification of Differentially Expressed mRNA in Cancers-5

The process in EXAMPLE 1 was repeated except that the marker LFG5 was used instead of the marker LFG1.

Analysis of the chip data showed that the expression of the marker LFG5 was significantly down-regulated in cancer tissue samples compared to samples from normal tissue. The expression level of LFG5 (SEQ ID NO: 11) can be measured by chip sequence fragment no. 46659_at on Affymetrix GeneChips® U95. The expression levels of 46659_at in various malignant neoplasms, compared to normal control tissues, are shown in Table 6, where the fold-change, the direction of the change (up- or down-regulation), p-value are also indicated. The fold change (cancerous/normal) was calculated by comparing the geometric mean of average difference in a cancerous sample set against the geometric mean of average difference in the normal tissue sample set. Also indicated in the Table 6 are, for each tissue type, the numbers of samples that are called present, absent, or marginal together with the total number of samples in that sample set. These data indicate that differential regulation of LFG5 may be diagnostic for cancer.

TABLE 6

| Tissue | Pathology/Morphology | Geometric Mean | Number of Samples | | | Fold | | |
|---|---|---|---|---|---|---|---|---|
| | | | Total | Present | Marginal | Absent | Change | Direction | p-value |
| BREAST | NORMAL TISSUE, NOS | 152.75 | 34 | 31 | 0 | 3 | | | |
| | INFILTRATING DUCT CARCINOMA | 404.58 | 61 | 60 | 0 | 1 | 2.65 | up | 0 |
| | INFILTRATING LOBULAR CARCINOMA | 277.71 | 10 | 10 | 0 | 0 | 1.82 | up | 0.07445 |
| ESOPHAGUS | NORMAL TISSUE, NOS | 85.47 | 18 | 15 | 0 | 2 | | | |
| | ADENOCARCINOMA, NOS | 373.97 | 8 | 8 | 0 | 0 | 4.38 | up | 0.0009 |
| KIDNEY | NORMAL TISSUE, NOS | 53.58 | 25 | 17 | 0 | 8 | | | |
| | CLEAR CELL CARCINOMA | 161.36 | 11 | 11 | 0 | 0 | 3.01 | up | 0.00011 |
| | RENAL CELL CARCINMA | 249.37 | 16 | 16 | 0 | 0 | 4.65 | up | 0 |
| LUNG | NORMAL TISSUE, NOS | 330.65 | 32 | 31 | 0 | 1 | | | |
| | ADENOCARCINOMA, NOS | 195.43 | 39 | 35 | 0 | 4 | 1.69 | down | 0.00538 |
| LYMPH NODE | NORMAL TISSUE, NOS | 219.77 | 9 | 9 | 0 | 0 | | | |
| | MALIGNANT LYMPHOMA, NOS | 142.09 | 12 | 11 | 0 | 1 | 1.55 | down | 0.25114 |
| OVARY | NORMAL TISSUE, NOS | 90.40 | 23 | 19 | 0 | 4 | | | |
| | PAPILLARY SEROUS ADENOCARCINOMA | 418.81 | 23 | 23 | 0 | 0 | 4.63 | up | 0 |
| PANCREAS | NORMAL TISSUE, NOS | 38.53 | 20 | 12 | 0 | 8 | | | |
| | ADENOCARCINOMA, NOS | 344.37 | 25 | 25 | 0 | 0 | 8.94 | up | 0 |
| STOMACH | NORMAL TISSUE, NOS | 185.50 | 18 | 17 | 0 | 1 | | | |
| | ADENOCARCINOMA, NOS | 279.62 | 38 | 35 | 0 | 3 | 1.51 | up | 0.12664 |

The GeneChip expression results, determined by sample binding to chip sequence fragment no. 46659_at, were validated by quantitative RT-PCR (Q-RT-PCR) using the Taqman® assay (Perkin-Elmer). PCR primers (5'-AAGGCTT-TATCAGGTCTGCATATAGAATC-3' (SEQ ID NO: 51) and 5'-GCAAAGAACCCTAATGCTATTTATCAGC-3' (SEQ ID NO: 52)) designed based on the sequence information file of the specific Affymetrix fragment (46659_at) were used in the assay. The target gene in each RNA sample (10 ng of total RNA) was assayed relative to a reference gene. For this purpose, primers (5'-GTTTTTCCTAATTTTGGCATGAAC-3' (SEQ ID NO: 19) and 5'-CGCCCAAGCTTTTCCTTTT-3' (SEQ ID NO: 20)) specific to the CTBP1 gene (C-terminal binding protein 1) were used to serve as control primers. This approach provides the relative expression as measured by cycle threshold (Ct) value of the target mRNA relative to an amount of CTBP1 Ct value. The sample panel included total RNA pairs of normal and tumor tissues from kidney, lung, ovary, and pancreas (Ambion, Inc., Austin, Tex.). The Q-RT-PCR data confirms the differential regulation of LFG5 in cancer compared to normal samples.

Example 10

Cloning of Full-Length Human cDNA (LFG5) Corresponding to Differentially Expressed mRNA Species The full-length cDNA having SEQ ID NO: 11 was obtained by the oligo-pulling method using the GeneTrapper assay (Life Technologies, Rockville, Md.). Briefly, a gene-specific oligo (5'-GAGAAGACCAGGGAAGAAGCAG-3' (SEQ ID NO: 53)) was designed based on the sequence of an EST containing 46659_at sequence. The oligo was labeled with biotin and used to hybridize with 5 μg of single strand plasmid DNA (cDNA recombinants) from a human heart library (ResGen, Huntsville, Ala.) following the procedures of Sambrook et al. The hybridized cDNAs were separated by streptavidin-conjugated beads and eluted by heating. The eluted cDNA was converted to double strand plasmid DNA and used to transform $E.\ coli$ cells (DH10B) and the longest cDNA was screened. After positive selection was confirmed by PCR using gene-specific primers, the cDNA clone was subjected to DNA sequencing.

The nucleotide sequence of the full-length human cDNAs corresponding to the differentially regulated mRNA detected above is set forth in SEQ ID NO: 11. The cDNA comprises 3098 base pairs.

An open reading frame within the cDNA nucleotide sequence of SEQ ID NO: 11, at nucleotides 223-1569 (223-1572 including the stop codon), encodes a protein of 449 amino acids. The amino acid sequence corresponding to a predicted protein encoded by SEQ ID NO: 11 is set forth in SEQ ID NO: 12.

SEQ ID NO: 12 contains a thymidylate kinase domain (amino acid positions 257-438). Thymidylate kinase is a member of nucleotide monophosphate kinases (NMPKs) which play roles in the nucleotide synthesis for RNA and DNA synthesis and are required for the pharmacological activation of therapeutic nucleoside and nucleotide analogs (Van Rompay et al. (2000), *Pharmacology & Therapeutics* 87:189-198). SEQ ID NO: 12 exhibits homology to a mouse thymidylate kinase (GenBank Accession No. NM_020557) which is induced during macrophage activation (Lee and O'Brien (1995), *J. Immunol.* 154:6094-6102). It shows 63% identity over the entire contiguous sequence.

Figure 7:
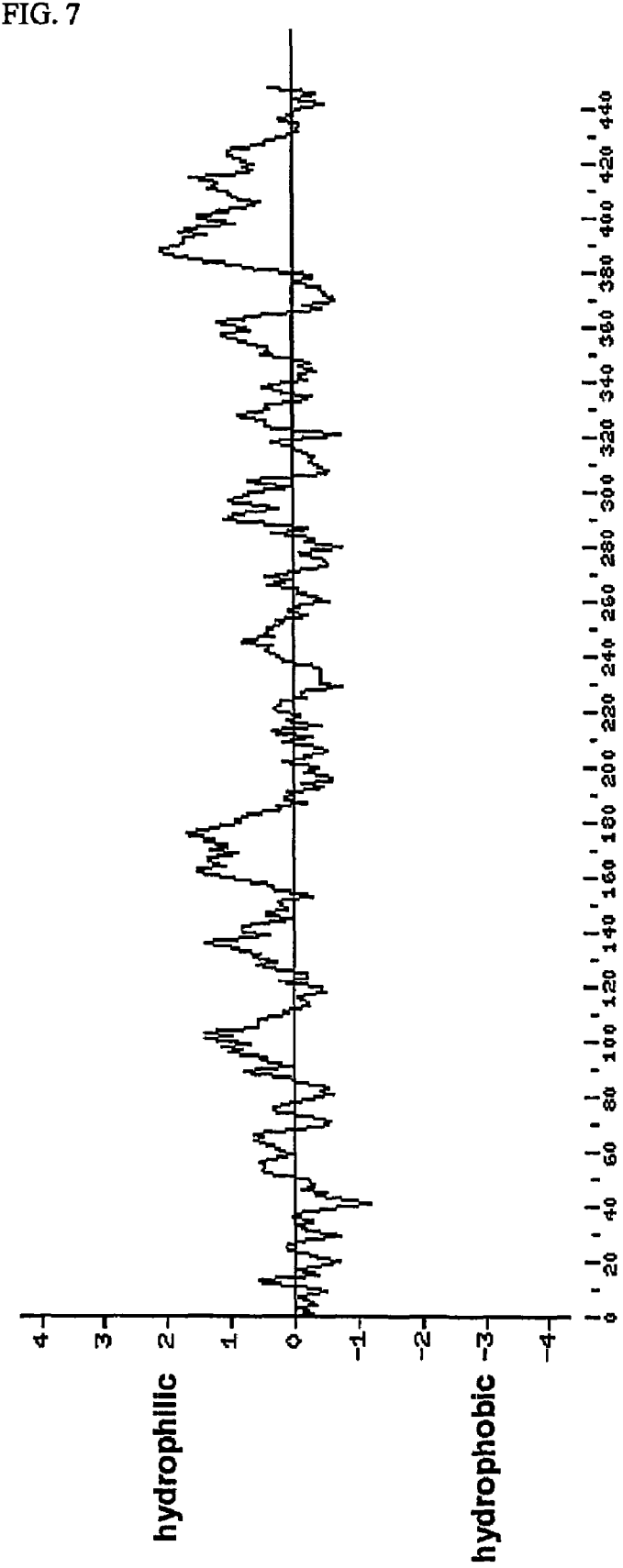
FIG. 7 is a hydrophobicity plot of the protein encoded by the open reading frame of ALFG5 (SEQ ID NO: 12). Analysis was performed according to the method of Kyte-Doolittle.
Figure 8:
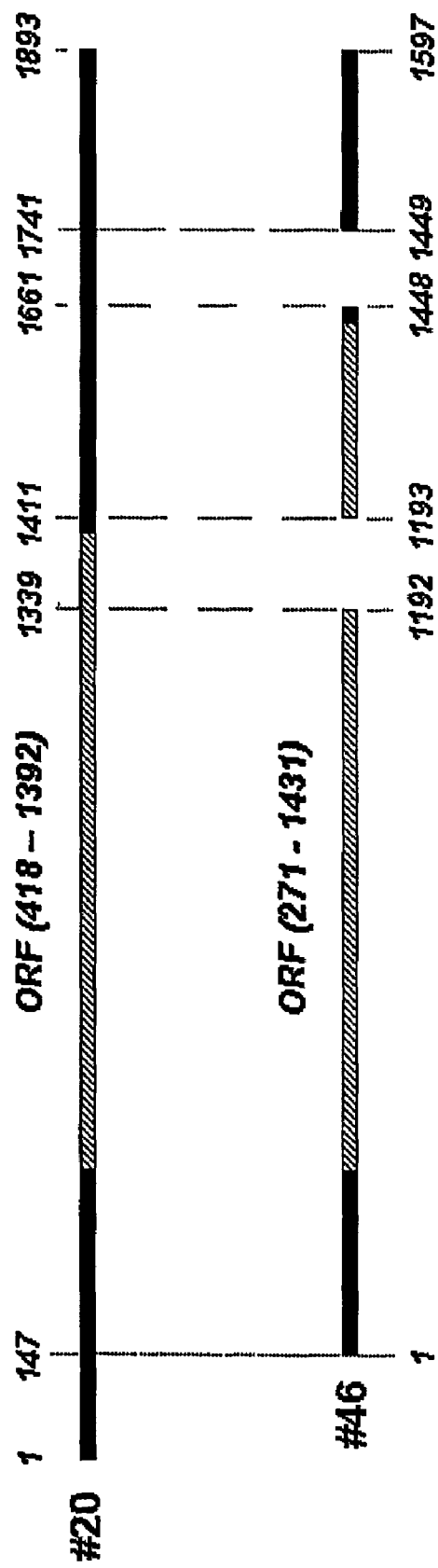
FIG. 8 shows the relative alignment positions of the two LFG6 clones.

FIG. 7 shows the results of a hydrophobicity analysis of the amino acid sequence of SEQ ID NO: 12 using Kyte-Doolittle values (Kyte and Doolittle (1982), *J. Mol. Biol.* 157:105-142). Hydrophilic regions may be used to produce antigenic peptides, as described above.

Analysis by Northern blot was performed to determine the size of the mRNA transcripts that correspond to LFG5. A Northern blot containing total RNAs from various human tissues was used (Human MYN Blot, Clontech, Palo Alto, Calif.), and an EST containing 82941_at sequence was radioactively labeled by the random primer method and used to probe the blot. The blot was hybridized in 50% formamide, 5×SSPE, 0.1% SDS, 5× Denhart's solution, and 0.2 mg/ml herring sperm DNA at 42° C. and washed with 0.2×SSC containing 0.1% SDS at room temperature. The Northern blot showed a single transcript for this gene, which is approximately 3.0 kb in size. This corresponds to the size of the LFG5 clone (SEQ ID NO: 11).

Example 11

Identification of Differentially Expressed mRNA in Cancers-6

The process in EXAMPLE 1 was repeated except that the marker LFG6 was used instead of the marker LFG1.

Analysis of the chip data showed that the expression of the marker LFG6 was significantly up-regulated in cancer tissue samples compared to samples from normal tissue. The expression level of LFG6 (SEQ ID NO: 13 or 15) can be measured by chip sequence fragment no. 44103_at on Affymetrix GeneChips® U95. The 44103_at sequence is derived from the EST AA865614. The expression levels of 44103_at in various malignant neoplasms, compared to normal control tissues, are shown in Table 7, where the fold-change, the direction of the change (up- or down-regulation), p-value are also indicated. The fold change (cancerous/normal) was calculated by comparing the geometric mean of average difference in a cancerous sample set against the geometric mean of average difference in the normal tissue sample set. A fold change greater than 1.5 was considered to be significant (Wodicka et al. (1997), *Nature Biotech.* 15:1359-1367). Also indicated in the Table 7 are, for each tissue type, the numbers of samples that are called present, absent, or marginal together with the total number of samples in that sample set. These data indicate that up-regulation of LFG6 may be diagnostic for cancer.

TABLE 7

| Tissue | Pathology/Morphology | Geometric Mean | Number of Samples | | | | Fold Change | Direction | p-value |
| --- | --- | --- | --- | --- | --- | --- | --- | --- | --- |
| | | | Total | Present | Marginal | Absent | | | |
| KIDNEY | NORMAL TISSUE, NOS | 337.71 | 25 | 25 | 0 | 0 | | | |
| | CLEAR CELL ADENOCARCINOMA, NOS | 556.82 | 11 | 11 | 0 | 0 | 1.65 | up | 0.00314 |

TABLE 7-continued

| Tissue | Pathology/Morphology | Geometric Mean | Total | Present | Marginal | Absent | Fold Change | Direction | p-value |
|---|---|---|---|---|---|---|---|---|---|
| LIVER | NORMAL TISSUE, NOS | 406.93 | 19 | 18 | 0 | 1 | | | |
| | HEPATOCELLULAR CARCINOMA, NOS | 619.40 | 23 | 22 | 0 | 1 | 1.52 | up | 0.00303 |
| OVARY | NORMAL TISSUE, NOS | 380.10 | 23 | 23 | 0 | 0 | | | |
| | PAPILLARY SEROUS ADENOCARCINOMA | 578.60 | 23 | 23 | 0 | 0 | 1.52 | up | 0.00013 |
| PANCREAS | NORMAL TISSUE, NOS | 138.75 | 20 | 11 | 1 | 8 | | | |
| | ADENOCARCINOMA, NOS | 453.01 | 25 | 25 | 0 | 0 | 3.26 | up | 0.00002 |

The GeneChip expression results, determined by sample binding to chip sequence fragment no. 44103_at, were validated by quantitative RT-PCR (Q-RT-PCR) using the Taqman® assay (Perkin-Elmer). PCR primers (5'-GGACGGG-GAACTTGGACGC-3' (SEQ ID NO: 54) and 5'-AAGTGCAGGGCCTCTGGGTG-3' (SEQ ID NO: 55)) designed based on the sequence information file of the specific Affymetrix fragment (44103_at) were used in the assay. The target gene in each RNA sample (10 ng of total RNA) was assayed relative to a reference gene. For this purpose, primers (5'-GTTTTTCCTAATTTTGGCATGAAC-3' (SEQ ID NO: 19) and 5'-CGCCCAAGCTTTTCCTTTT-3' (SEQ ID NO: 20)) specific to the CTBP1 gene (C-terminal binding protein 1) were used to serve as control primers. This approach provides the relative expression as measured by cycle threshold (Ct) value of the target mRNA relative to an amount of CTBP1 Ct value. The sample panel included total RNA pairs of normal and tumor tissues from liver and ovary (Ambion, Inc., Austin, Tex.). The Q-RT-PCR data confirms the up-regulation of LFG6 in cancer compared to normal samples.

Example 12

Cloning of Full-Length Human cDNA (LFG6) Corresponding to Differentially Expressed mRNA Species The full-length cDNA having SEQ ID NO: 13 or 15 was obtained by the oligo-pulling method using the GeneTrapper assay (Life Technologies, Rockville, Md.). Briefly, a gene-specific oligo (5'-CGCTGGGTCATCGGACGGT-3' (SEQ ID NO: 56)) was designed based on the sequence of an EST containing 44103_at sequence. The oligo was labeled with biotin and used to hybridize with 5 µg of single strand plasmid DNA (cDNA recombinants) from a fully differentiated human stomach adenocarcinoma library (ResGen, Huntsville, Ala.) following the procedures of Sambrook et al. The hybridized cDNAs were separated by streptavidin-conjugated beads and eluted by heating. The eluted cDNA was converted to double strand plasmid DNA and used to transform E. coli cells (DH10B) and the longest cDNA was screened. After positive selection was confirmed by PCR using gene-specific primers, the cDNA clone was subjected to DNA sequencing.

The nucleotide sequence of the full-length human cDNAs corresponding to the differentially regulated mRNA detected above is set forth in SEQ ID NOS: 13 and 15. In the former, the cDNA comprises 1893 base pairs. In the latter, the cDNA comprises 1597 base pairs.

Figure 9:
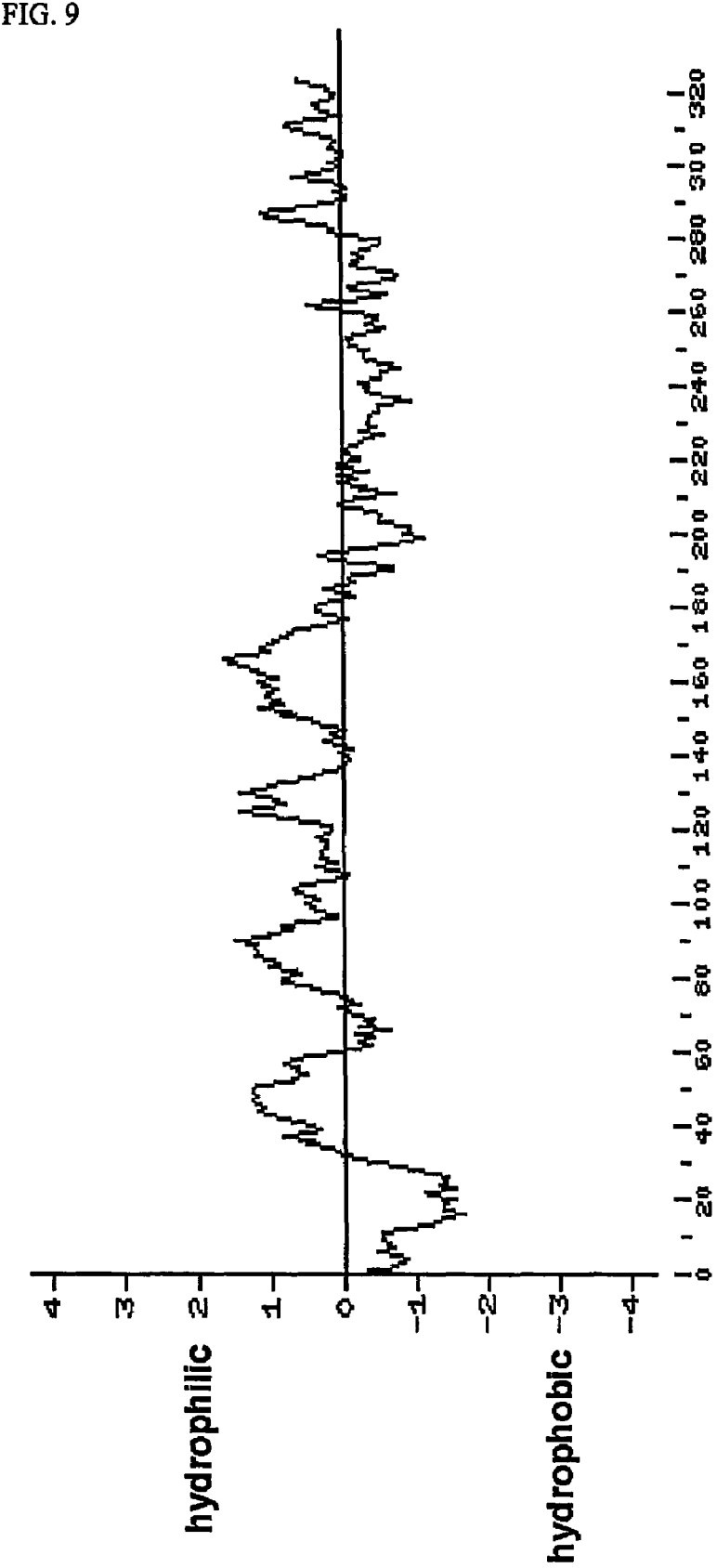
FIG. 9 is a hydrophobicity plot of the protein encoded by the open reading frame of LFG6-#20 (SEQ ID NO: 14). Analysis was performed according to the method of Kyte-Doolittle.

An open reading frame within the cDNA nucleotide sequence of SEQ ID NO: 13, at nucleotides 418-1392 (418-1395 including the stop codon), encodes a protein of 325 amino acids. The amino acid sequence corresponding to a predicted protein encoded by SEQ ID NO: 13 is set forth in SEQ ID NO: 14. FIG. 9 shows the results of a hydrophobicity analysis of the amino acid sequence of SEQ ID NO: 14 using Kyte-Doolittle values (Kyte and Doolittle (1982), *J. Mol. Biol.* 157:105-142). Hydrophilic regions may be used to produce antigenic peptides, as described above.

Figure 10:
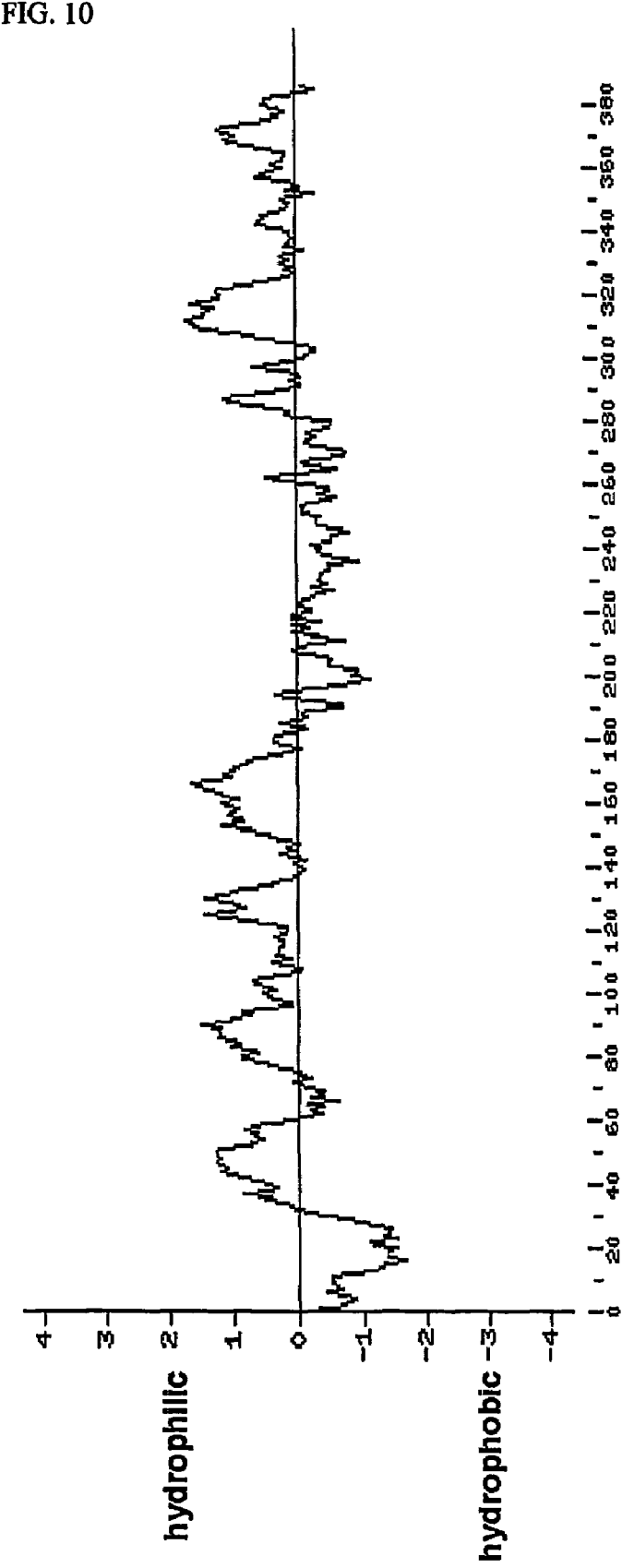
FIG. 10 is a hydrophobicity plot of the protein encoded by the open reading frame of LFG6-46 (SEQ ID NO: 16). Analysis was performed according to the method of Kyte-Doolittle.

An open reading frame within the cDNA nucleotide sequence of SEQ ID NO: 15, at nucleotides 271-1431 (271-1434 including the stop codon), encodes a protein of 387 amino acids. The amino acid sequence corresponding to a predicted protein encoded by SEQ ID NO: 15 is set forth in SEQ ID NO: 16. FIG. 10 shows the results of a hydrophobicity analysis of the amino acid sequence of SEQ ID NO: 16 using Kyte-Doolittle values byte and Doolittle (1982), *J. Mol. Biol.* 157:105-142). Hydrophilic regions may be used to produce antigenic peptides, as described above.

SEQ ID NOS: 14 and 16 contain ubiquitin homologues (UBQ) domain (amino acid positions 239-300). SEQ ID NOS: 14 and 16 are similar to rat Sharpin protein (Lim et al. (2001), *Mol Cell Neurosci* 17:385-397). Sharpin directly interacts with the ankyrin repeats of Shank protein which functions in the organization of cytoskeletal complexes and intracellular signaling at specialized cell junctions (Sheng and Kim (2000), *J Cell Sci* 113:1851-1856).

Analysis by Northern blot was performed to determine the size of the mRNA transcripts that correspond to LFG6. A Northern blot containing total RNAs from various human tissues was used (Human 12-Lane MTN Blot, Clontech, Palo Alto, Calif.), and an EST containing 44103_at sequence was radioactively labeled by the random primer method and used to probe the blot. The blot was hybridized in 50% formamide, 5×SSPE, 0.1% SDS, 5× Denhart's solution, and 0.2 mg/ml herring sperm DNA at 42° C. and washed with 0.2×SSC containing 0.1% SDS at room temperature. The Northern blot showed three transcripts for this gene, which are approximately 2.2 kb, 1.5 kb, and 1.2 kb in size. This corresponds to the sizes of the LFG6 clones (SEQ ID NO: 13 and 15).

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

What is claimed is:

1. An isolated nucleic acid molecule consisting of:
   (a) nucleotides 390-4880 of SEQ ID NO: 1;
   (b) nucleotides 39-4883 of SEQ ID NO: 1;
   (c) nucleotides 12-4904 of SEQ ID NO: 3;
   (d) nucleotides 12-4907 of SEQ ID NO: 3;
   (e) the full complement of nucleotides 390-4880 of SEQ ID NO: 1;
   (f) the full complement of nucleotides 390-4883 of SEQ ID NO: 1;
   (g) the full complement of nucleotides 12-4904 of SEQ ID NO: 3; or
   (h) the full complement of nucleotides 12-4907 of SEQ ID NO: 3.

2. An isolated nucleic acid molecule comprising one or more heterologous expression control elements operably linked to the nucleic acid molecule of claim 1.

3. A vector comprising the isolated nucleic acid molecule of claim 2.

4. An isolated host cell transformed with the isolated nucleic acid molecule of claim 1.

5. An isolated host cell comprising the vector of claim 3.

6. The isolated host cell of claim 5, wherein said isolated host cell is selected from the group consisting of a prokaryotic host cell and an eukaryotic host cell.

7. A method for producing a polypeptide comprising:
 (i) transforming a host cell with an isolated nucleic acid molecule comprising one or more heterologous expression control elements operably linked to a nucleic acid molecule comprising:
  (a) nucleotides 390-4880 of SEQ ID NO: 1,
  (b) nucleotides 390-4883 of SEQ ID NO: 1,
  (c) nucleotides 12-4904 of SEQ ID NO: 3, or
  (d) nucleotides 12-4907 of SEQ ID NO: 3; and
 (ii) culturing the transformed host cell of step (i) under suitable conditions to produce said polypeptide.

8. The method of claim 7, wherein said host cell is selected from the group consisting of a prokaryotic host cell and an eukaryotic host cell.

* * * * *